(12) United States Patent
Takaki et al.

(10) Patent No.: US 6,593,408 B1
(45) Date of Patent: Jul. 15, 2003

(54) ORGANIC POLYMER/INORGANIC FINE PARTICLE-DISPERSED AQUEOUS SOLUTION HAVING EXCELLENT STABILITY AND USES THEREOF

(75) Inventors: Toshihiko Takaki, Sodegaura (JP); Masaru Tanabe, Sodegaura (JP); Hiroshi Itoh, Sodegaura (JP); Toshiki Oyanagi, Tokyo (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 09/831,641
(22) PCT Filed: Nov. 12, 1999
(86) PCT No.: PCT/JP99/06341
§ 371 (c)(1), (2), (4) Date: May 11, 2001
(87) PCT Pub. No.: WO00/29485
PCT Pub. Date: May 25, 2000

(30) Foreign Application Priority Data

| Nov. 13, 1998 | (JP) | ............................................. 10-323827 |
| Mar. 12, 1999 | (JP) | ............................................. 11-065758 |
| Mar. 12, 1999 | (JP) | ............................................. 11-065761 |
| Mar. 30, 1999 | (JP) | ............................................. 11-087813 |
| May 20, 1999 | (JP) | ............................................. 11-139932 |
| May 20, 1999 | (JP) | ............................................. 11-139933 |

(51) Int. Cl.$^7$ ................................................. C08K 3/32
(52) U.S. Cl. ........................ 524/414; 524/417; 524/556; 524/557; 524/564

(58) Field of Search .................................. 524/414, 417, 524/556, 557, 564

(56) References Cited

FOREIGN PATENT DOCUMENTS

| EP | 939431 | | 9/1999 |
| JP | 05-17133 | | 1/1993 |
| JP | 05222693 | * | 8/1993 |
| JP | 7-101708 | | 4/1995 |
| JP | 10-000229 | | 1/1998 |
| JP | 10-36458 | | 2/1998 |
| JP | 10-152673 | | 6/1998 |
| JP | 10-245450 | | 9/1998 |
| WO | WO98/14987 | | 4/1998 |

* cited by examiner

*Primary Examiner*—Bernard Lipman
(74) *Attorney, Agent, or Firm*—Burns, Doane, Swecker & Mathis, LLP

(57) ABSTRACT

An organic polymer/inorganic fine particle-dispersed aqueous solution having excellent dispersion stability comprising a water-slightly soluble inorganic fine particle (B) having a particle diameter of 500 nm or less obtained by reacting (a) a compound of a second group element in the periodic table with (b) at least one compound selected from organic acids, inorganic acids and salts thereof in the presence of a water-soluble or water-dispersible synthetic high molecular compound (A) having a carboxyl group in a proportion of (A):(B)=10:90 to 99.99:0.01 (weight ratio). The above dispersed aqueous solution can be used as a paper-making chemical, an ink jet recording chemical, medical materials and cosmetic raw materials.

48 Claims, 12 Drawing Sheets

(a)

500nm
×20,000

(b)

500nm
×20,000

(c)

(a)

50nm
×200,000

(b)

50nm
×200,000

ORGANIC POLYMER/INORGANIC FINE PARTICLE-DISPERSED AQUEOUS SOLUTION HAVING EXCELLENT STABILITY AND USES THEREOF

TECHNICAL FIELD

The present invention relates to an organic polymer/inorganic fine particle-dispersed aqueous solution having excellent dispersion stability, a composite, production processes therefor and uses thereof.

BACKGROUND ART

In organic, inorganic and metallic base materials, materials having characteristics which can not be achieved by a single material can be produced by compounding thereof, and it is just an ordinary method in development of materials in these days. For example, a fiber-reinforced plastic material (FRP) obtained by compounding a glass fiber with a polymer has a strength which can not be achieved only by the polymer alone. On the other hand, observing this material from a glass fiber side, we can take a viewpoint that a glass fiber which is fragile and has poor processability in itself is turned into a material having moldability by compounding with a polymer. Thus, compounding makes it possible to allow functions and performances which can not be achieved by a single material to be revealed by making the best use of the characteristics of the respective base materials or making up the defects thereof. In conventional compounded materials, a size of a disparate material (dispersed phase) in a matrix (dispersion medium) is of an order of micrometer or larger, and effects expected from compounding in such a size have been brought.

It has come to be reported in many cases that microminiaturization of a dispersed phase of a compounded material into a nanometer order in combination with an advance in a technique to analyze a micro area represented by a scanning probe microscope (SPM) makes it possible to prepare materials having a high function and multifunctions or materials having a new function which have not been able to be achieved by conventional compounded materials, and attentions are paid thereto.

Known as examples of materials (hereinafter referred to as a nano-composite) obtained by compounding organic materials with inorganic materials in a nanometer order are nano-composites obtained by compounding stratified clay minerals such as clay and synthetic stratified silicates with polymers such as nylon and nano-composites of silica with polymers making use of a sol-gel method. In the former nano-composites, investigates are (1) a method of inserting an organic monomer between layers of a stratified compound to carry out polymerization, (2) an in-situ polymerization method of carrying out polymerization of a polymer and production and dispersion of a filler at the same time and (3) a method of carrying out mixing and dispersing a stratified compound and a polymer in the presence of an organic cation. These methods make use basically of a cleavage phenomenon of a filler following intercalation of an organic substance, so that an inorganic substance is restricted to a stratified clay mineral which can be dispersed as a structure of a nanometer order. In the latter nano-composites, nano-compounding an inorganic substance with an organic substance has become possible by synthesizing the inorganic substance at a low temperature by a sol-gel method. They have the merit that refined inorganic raw materials can be used but have the defects that the raw materials are expensive and the volume shrinks as the reaction goes on.

In a nano-composite of an organic polymer with an inorganic substance, worked out as well in addition to an intercalation method and a sol-gel method is a method in which an inorganic substance is mechanically pulverized into a nanometer order and then mixed with an organic polymer to obtain an organic-inorganic nano-composite. In general, however, it is recognized that it is difficult to mechanically pulverize an inorganic substance into a nanometer order, and even though can be pulverized, it is not easy to mix homogeneously with an organic polymer which is a disparate material in a nanometer order while inhibiting recoagulation.

The present inventors have paid attentions to that if used as a component for an organic-inorganic nano-composite are calcium phosphates such as hydroxyapatite (hereinafter abbreviated as HAp) and tricalcium phosphate (hereinafter abbreviated as TCP), which are not biologically toxic and have high affinity with an organic substance, there is a possibility they may be turned into very useful materials. HAp is an inorganic component constituting a hard tissue of a vertebrate, and researched is practical use thereof as a hard tissue-substituting material for an artificial bone, an artificial root of tooth and an artificial joint. An HAp sintered substance is a brittle material which is strong against compression but weak against tension if it is used alone, and it has the defect that the moldability is poor. Disclosed as a method for improving this defect in Japanese Patent Application Laid-Open No. Hei 10-229 is a technique for obtaining an organic-inorganic composite which is improved in stability in molding processing and well balanced in flexibility, strength, an elastic modulus, reproducibility and molding processability by mixing HAp with lactic acid base polyesters. This technique has been developed based on an idea to provide a material closer to an organism considering that HAp is present in an organism in the form of a compounded product with collagen which is a biopolymer. In this method, a composite is obtained by synthesizing a calcium phosphate compound such as HAp or TCP by a wet process, baking and pulverizing the resulting precipitate and then mixing it with a polymer by means of a mixer. Calcium phosphate particles used in this case have a size of 5 mm or less, and the organic polymer is restricted to a lactic acid base polyester. This material has achieved osteoconductivity and biocompatibility making the best use of the characteristics of the respective base materials, and it is not a material which is homogeneously dispersed in a nanometer order.

On the other hand, according to Japanese Patent Application Laid-Open No. Hei 7-101708, disclosed is a composite which comprises HAp powder having a crystal particle diameter of 0.5 $\mu$m (500 nm) or less and an organic substance such as collagen and which is close to a tooth and a bone of an organism. In this technique, obtained is a composite having a high Young's modulus by adding a mixed solution of collagen and phosphoric acid to a suspension of calcium hydroxide while vigorously stirring, filtering and drying the resulting precipitate to obtain a hydrate and applying a pressure of 200 MPa to the hydrate at 40° C. It is confirmed by Tanaka et al. [BIO INDUSATRY, Vol. 13 (No. 8), 28 (1996)] that this HAp-collagen composite is a nano-composite in which C axis of HAp nanocrystals (some nm) is orientated along collagen fibers (30 nm). However, included in producing materials close to a vital bone are the problems that a synthetic method in which strength close to that of a vital bone can freely be controlled has to be established and that a method of reducing antigenicity of collagen has to be established. Further, this material is not a material having a high transparency which is characteristic to a nano-composite since it has an oriented structure.

Inorganic substances such as calcium phosphate and calcium carbonate which can be synthesized by a liquid phase process are liable to be turned into a low crystalline substance or a fine crystal in many cases, and they are usually turned into a gelatinous precipitate. Usually, used is a material obtained by filtering, drying, baking and then pulverizing this precipitate, but it is difficult to pulverize them to a primary particle, and it is not easy as well to disperse and mix nano-order particles in a polymer. Thus, a practical method of producing a composite in which an inorganic substance including calcium phosphate synthesized by a liquid phase process is homogeneously dispersed in a nano order has not been available in conventional techniques.

The paper-making industry is an industry in which a large quantity of forest resources is consumed as raw materials and a great amount of energy is required for producting pulp and in a paper-making step, and in the state that environment problems become more serious on a global level in recent years, an effort toward reducing a load onto the environment as much as possible is energetically made. In particular, recycling of waste paper as resources increases the importance further more, and it is said that recycling goes on up to a level close to a limit excluding unrecoverable paper such as sanitary paper and paper for books. However, waste paper is a raw material in which fibers are shortened by cutting and abrasion, and therefore an elevated use ratio thereof results in bringing about a reduction in strength of the paper. Such reduction in paper strength has been made up by adding or coating a water-soluble high molecular compound represented by starches such as starch oxide and cationized starch, polyvinyl alcohol (PVA) and (meth)acrylamide base polymers. On the other hand, paper-strengthening agents comprising the water-soluble high molecular compounds described above are used in order to make up a reduction in paper strength also when adding various additives which are mainly inorganic pigments for the purpose of reducing a use amount of pulp from a viewpoint of resource saving.

Among those paper-strengthening agents, the (meth)acrylamide base polymers are known as a high performance chemical which brings about a large effect by a trace amount. However, environmental problems are important subjects which have to be now considered in a global scale, and chemicals having higher performances than ever have increasingly been desired to cope with the problems of deteriorating in the quality of raw materials and reducing the amount of pulp.

There have so far been investigated as a method of providing a (meth)acrylamide base polymer with a high paper-strengthening ability, a method in which it is copolymerized with a functional monomer, a method in which a functional group is introduced thereinto by after-modification and a method in which a cross-linking structure is introduced thereinto. However, in the state that the further higher performances are required in the future, the performances which can be achieved only by conventional methods of modifying polymers are limited, and therefore chemicals for paper making based on a new concept are desired to be provided.

Printing by an ink jet recording system has the advantages that it has less noise and is silent; high-speed printing is possible; a printing cost is low; coloring is easy; printed record is clear; and printing in a large size is possible. Accordingly, it prevails widely. The ink jet recording system is a recording system in which ink droplets are jetted from fine nozzles by various operating methods and adhered on a recording sheet such as paper to obtain information in the form of a letter or an image. Required to the sheet used for the ink jet recording system are such characteristics that the droplets adhered on the sheet surface according to the principle of the above system are quickly absorbed into the sheet and that spreading and feathering on the surface are controlled and the ink stays in the vicinity of the sheet surface as much as possible in order to elevate the color-developing intensity.

It has so far been proposed as a method of endowing an ink jet recording sheet with these characteristics to provide an ink absorptive coating layer on a sheet surface. Proposed is, for example, a coating layer comprising silica powder or alumina powder having high absorptivity and a binder of a water-soluble polymer such as polyvinyl alcohol as principal components and further comprising various additives mixed in order to improve an ink-fixing property and water resistance.

Thus, an ink jet recording sheet having a coating layer using silica powder or alumina powder as an inorganic filler is improved in ink absorptivity to a large extent and makes it possible to obtain an image having high image quality. However, brought about is the defect regarding the light fastness that the above coating layer is discolored to a yellow color with storing over a long period of time. In recent years, an outstanding progress in an ink jet printer has made it possible to readily obtain an image having high image quality in full colors. A recording sheet therefor has to have high whiteness, and therefore the preceding defect regarding light fastness such as yellowing with the passage of time is a large problem. Further, a recording sheet having the above coating layer has the problem that a part on which an adhesive tape is stuck causes marked yellowing when the adhesive tape is stuck on it. Thus, there has been involved the defect that when an adhesive tape is stuck on the above recording sheet for fastening, the appearance is notably damaged by yellowing.

The present inventors considered that if developed is a material which does not produce precipitates in the course of compounding calcium phosphate including the HAp described above and other inorganic substances with a polymer and which can be turned into a molded article without applying high pressure, it will be a material which is useful in many fields such as paper-making chemicals as well as vital materials. However, in nano-compounding with a polymer, there are inorganic substances to which a compounding method by the intercalation method and the sol-gel method each described above can not be applied. Accordingly, the present inventors have paid attentions to that some of inorganic substances can be synthesized in an aqueous medium by a liquid phase process other than the sol-gel method, and they have come to consider that those inorganic substances may be able to be nano-compounded with water-soluble or water-dispersible polymers.

An object of the present invention is to provide an organic polymer/inorganic fine particle-dispersed aqueous solution which has excellent molding processability and forms a transparent film and which can be used for various uses by stably dispersing inorganic nanometer-order fine particles without causing coagulation with and separation from water-soluble or water-dispersible polymers, which has so far been difficult in conventional methods, and uses thereof.

DISCLOSURE OF THE INVENTION

The present inventors have found that a composite obtained by combining a water-soluble or water-dispersible synthetic high molecular compound having a carboxyl group with a water slightly soluble inorganic particle having a particle diameter of 500 nm or less, particularly a water slightly soluble inorganic particle having a particle diameter of 500 nm or less obtained by reacting a compound of a second group element in the periodic table with at least one compound selected from organic acids, inorganic acids and salts thereof is a material which meets the object described above, and the present invention has come to be achieved.

That is, the present invention comprises:

(1) an organic polymer/inorganic fine particle-dispersed aqueous solution having excellent dispersion stability comprising a water-soluble or water-dispersible synthetic high molecular compound (A) having a carboxyl group and a water slightly soluble inorganic fine particle (B) having a particle diameter of 500 nm or less in a proportion of (A):(B)=10:90 to 99.99:0.01 (weight ratio), (2) the organic polymer/inorganic fine particle-dispersed aqueous solution having excellent dispersion stability as described in the above item (1), wherein the water slightly soluble inorganic fine particle (B) having a particle diameter of 500 nm or less is a fine particle of a compound of a second group element in the periodic table, (3) the organic polymer/inorganic fine particle-dispersed aqueous solution having excellent dispersion stability as described in the above item (1), wherein the water slightly soluble inorganic fine particle (B) having a particle diameter of 500 nm or less is synthesized by reacting (a) a compound of a second group element in the periodic table with (b) at least one compound selected from organic acids, inorganic acids and salts thereof in the presence of the water-soluble or water-dispersible synthetic high molecular compound (A) having a carboxyl group, (4) the organic polymer/inorganic fine particle-dispersed aqueous solution having excellent dispersion stability as described in the above item (3), wherein (b) the organic acid or inorganic acid is at least one acid selected from oxo-acids and hydrohalogenic acids, (5) the organic polymer/inorganic fine particle-dispersed aqueous solution having excellent dispersion stability as described in the above item (3), wherein (a) the compound of a second group element in the periodic table is a calcium compound, (6) the organic polymer/inorganic fine particle-dispersed aqueous solution having excellent dispersion stability as described in the above item (3), wherein the water-soluble or water-dispersible synthetic high molecular compound (A) having a carboxyl group is a polymer of an ethylenically unsaturated compound, (7) the organic polymer/inorganic fine particle-dispersed aqueous solution having excellent dispersion stability as described in the above item (6), wherein the polymer of the ethylenically unsaturated compound is any of a (meth)acrylamide base polymer, a carboxyl group-modified polyvinyl alcohol and a vinylpyrrolidone base polymer, (8) the organic polymer/inorganic fine particle-dispersed aqueous solution having excellent dispersion stability as described in the above item (6), wherein the the polymer of the ethylenically unsaturated compound is any of:

① (meth)acrylamide base polymer which is a polymer of 1 to 100% by weight of an ethylenically unsaturated carboxylic acid amide compound and 0 to 99% by weight of a copolymerizable, ethylenically unsaturated compound, ② a carboxyl group-modified polyvinyl alcohol which is produced by saponifying a polymer of an ethylenically unsaturated carboxylic acid and vinyl acetate, and ③ a vinylpyrrolidone base polymer which is a polymer of 1 to 99.9% by weight of N-vinyl-2-pyrrolidone and 0.1 to 99% by weight of a copolymerizable, ethylenically unsaturated compound, (9) the organic polymer/inorganic fine particle-dispersed aqueous solution having excellent dispersion stability as described in any of the above items (6) to (8), wherein the water slightly soluble inorganic fine particle (B) is calcium phosphate,

(10) a production process for an organic polymer/inorganic fine particle-dispersed aqueous solution having excellent dispersion stability, characterized by producing a water slightly soluble inorganic fine particle (B) having a particle diameter of 500 nm or less by reacting (a) a compound of a second group element in the periodic table with (b) at least one compound selected from organic acids, inorganic acids and salts thereof in the presence of a water-soluble or water-dispersible synthetic high molecular compound (A) having a carboxyl group,

(11) an organic polymer/inorganic fine particle-composite having excellent transparency comprising a water-soluble or water-dispersible synthetic high molecular compound (A) having a carboxyl group and a water slightly soluble inorganic fine particle (B) having a particle diameter of 500 nm or less obtained by reacting (a) a compound of a second group element in the periodic table with (b) at least one compound selected from organic acids, inorganic acids and salts thereof in a proportion of (A):(B)=10:90 to 99.99:0.01 (weight ratio),

(12) an organic polymer/inorganic fine particle-composite having excellent transparency obtained from the organic polymer/inorganic fine particle-dispersed aqueous solution having excellent dispersion stability as described in any of the above items (1) to (9), comprising a water-soluble or water-dispersible synthetic high molecular compound (A) having a carboxyl group and a water slightly soluble inorganic fine particle (B) having a particle diameter of 500 nm or less in a proportion of (A):(B)=10:90 to 99.99:0.01 (weight ratio),

(13) the organic polymer/inorganic fine particle-composite having excellent transparency as described in the above item (11) or (12), wherein the composite is a film having excellent transparency,

(14) the organic polymer/inorganic fine particle-composite having excellent transparency as described in the above item (11), wherein the water-soluble or water-dispersible synthetic high molecular compound (A) having a carboxyl group is any of a (meth)acrylamide base polymer, a carboxyl group-modified polyvinyl alcohol and a vinylpyrrolidone base polymer.

(15) The organic polymer/inorganic fine particle-composite having excellent transparency as described in the above item (11) or (14), wherein the water slightly soluble inorganic fine particle (B) is calcium phosphate,

(16) a paper-making chemical comprising a water-soluble or water-dispersible synthetic high molecular compound (A) having a carboxyl group and a water slightly soluble inorganic fine particle (B) having a particle diameter of 500 nm or less obtained by reacting (a) a compound of a second group element in the periodic table with (b) at least one compound selected from organic acids, inorganic acids and salts thereof in a proportion of (A):(B)=10:90 to 99.99:0.01 (weight ratio),

(17) a paper-making chemical obtained from the organic polymer/inorganic fine particle-dispersed aqueous solution having excellent dispersion stability as described in any of the above items (1) to (9),

(18) a chemical for an ink-jet recording sheet comprising a water-soluble or water-dispersible synthetic high molecular compound (A) having a carboxyl group and a water slightly soluble inorganic fine particle (B) having a particle diameter of 500 nm or less obtained by reacting (a) a compound of a second group element in the periodic table with (b) at least one compound selected from organic acids, inorganic acids and salts thereof in a proportion of (A):(B)=10:90 to 99.99:0.01 (weight ratio),

(19) a chemical for an ink-jet recording sheet obtained from the organic polymer/inorganic fine particle-dispersed aqueous solution having excellent dispersion stability as described in any of the above items (1) to (9),

(20) the chemical as described in the above item (16) or (18), wherein the water-soluble or water-dispersible synthetic high molecular compound (A) having a carboxyl group is any of a (meth)acrylamide base polymer, a carboxyl group-modified polyvinyl alcohol and a vinylpyrrolidone base polymer,

(21) the chemical as described in the above item (16) or (18), wherein the water slightly soluble inorganic fine particle (B) is calcium phosphate,

(22) paper obtained by using the chemical as described in any of the above items (16) to (21),

(23) a cosmetic comprising the organic polymer/inorganic fine particle-dispersed aqueous solution having excellent dispersion stability as described in any of the above items (1) to (9), and

(24) a cosmetic comprising the organic polymer/inorganic fine particle-composite having excellent transparency as described in any of the above items (11) to (15).

BRIEF DESCRIPTION OF THE DRAWINGS

FIG. 1(*b*) is a transmission electron microscopic photograph obtained by photographing the dried carboxyl group-modified polyvinyl alcohol/calcium phosphate fine particle-dispersed aqueous solution (z1-8) which was prepared in Compounding Example 50 and diluted and then dried on a collodion film-coated copper mesh.

FIG. 1(*c*) is a transmission electron microscopic photograph obtained by photographing the dried calcium phosphate fine particle dispersion which was prepared in Compounding Comparative Example 1 and diluted and then dried on a collodion film-coated copper mesh.

FIG. 3(*b*) is a diagram showing an FT-IR spectra of a white solid obtained by subjecting the above film to heat treatment at 800° C. for 3 hours in an electric furnace based on a KBr tablet method.

FIG. 4(*b*) is a diagram showing FT-IR spectra of a white solid obtained by subjecting the above film to heat treatment at 800° C. for 9 hours in an electric furnace based on the KBr tablet method.

FIG. 6(*b*) is a diagram showing XRD spectra of a sample prepared by casting the PAM base-dispersed aqueous solution prepared in Compounding Example 12 on a glass substrate to form a film [peaks corresponding to the (h, k, 0) face were marked with *].

FIG. 7(*b*) is a diagram showing XRD spectra of a sample prepared by casting the carboxyl group-modified PAM base-dispersed aqueous solution prepared in Compounding Example 49 on a glass substrate to form a film.

BEST MODE-FOR CARRYING OUT THE INVENTION

Figure 1:
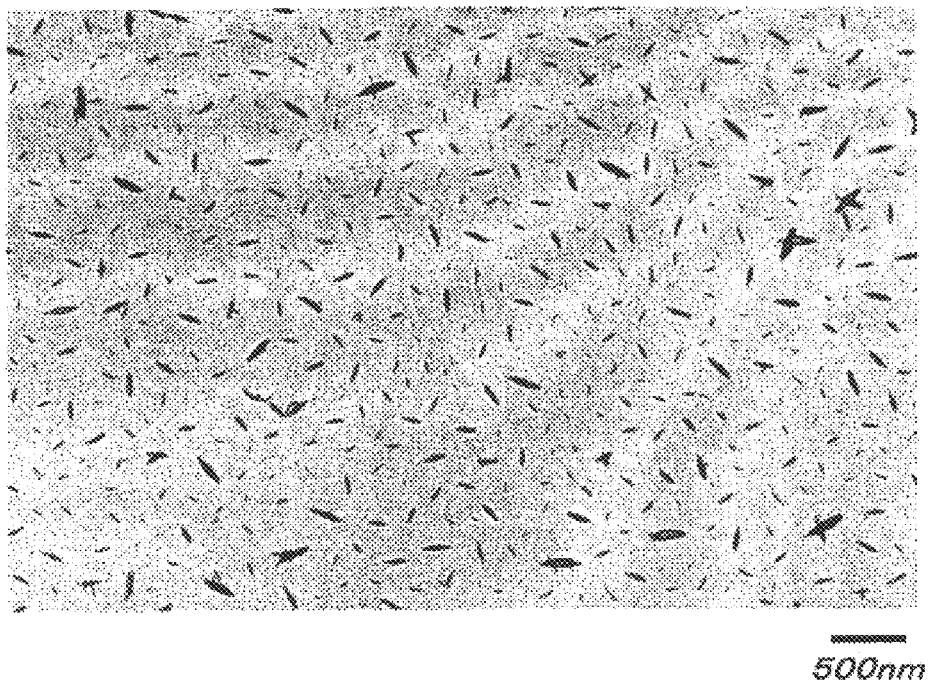
FIG. 1(*a*) is a transmission electron microscopic photograph obtained by photographing the dried (meth)acrylamide base polymer/calcium phosphate fine particle-dispersed aqueous solution (h-2) which was prepared in Compounding Example 9 and diluted and then dried on a collodion film-coated copper mesh.
Figure 1:
Figure 1:
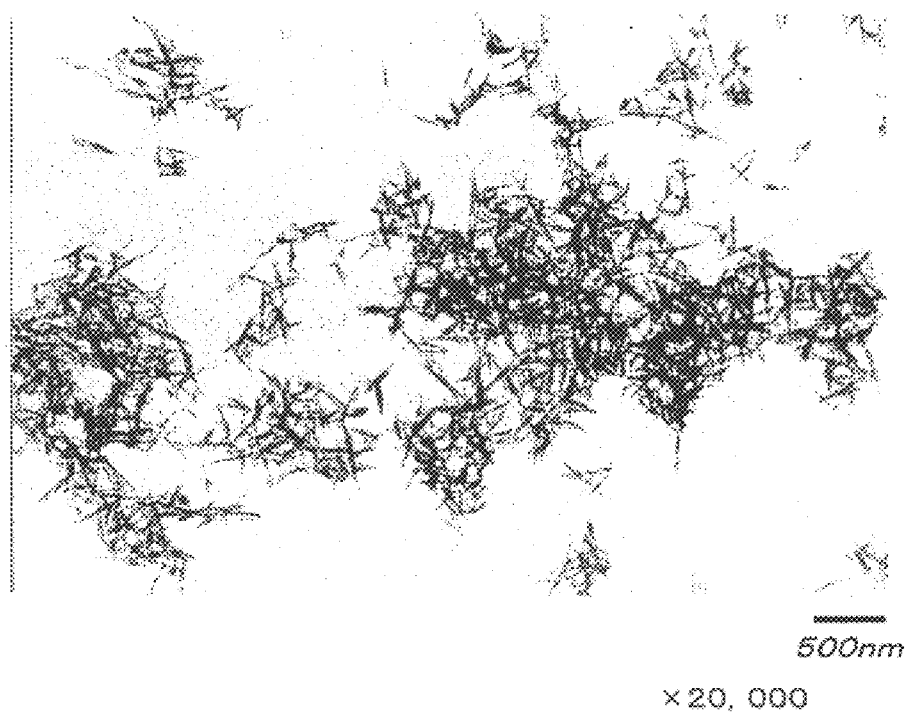

The present invention relates to a dispersed aqueous solution comprising an organic polymer/inorganic fine particle which contains a water-soluble or water-dispersible synthetic high molecular compound (A) having a carboxyl group and a water slightly soluble inorganic particle having a particle diameter of 500 nm or less, particularly a water slightly soluble inorganic fine particle (B) having a particle diameter of 500 nm or less obtained by reacting a compound of a second group element in the periodic table with at least one compound selected from organic acids, inorganic acids and salts thereof, a composite, a production process for the same and uses thereof.

The present invention is characterized in that use of the water-soluble or water-dispersible synthetic high molecular compound (A) having a carboxyl group for an organic polymer makes it possible to stably disperse the water slightly soluble inorganic fine particle (B) in a water base medium containing the organic polymer (A) and only drying of this dispersion provides a novel organic polymer/ inorganic fine particle-composite in which the water slightly soluble inorganic particles of a nanometer order are homogeneously dispersed in the organic polymer without causing coagulation or separation.

The water-soluble or water-dispersible synthetic high molecular compound used in the present invention means a compound synthesized by subjecting a raw material to chemical reaction treatment and includes those (semi-synthetic high molecular compounds) obtained by modifying natural high molecular materials. It is essential that the semi-synthetic high molecular compound used in the present invention contains a carboxyl group in a molecule, and examples thereof include carboxymethyl cellulose, carboxymethyl chitin, carboxymethyl starch and propylene glycol alginate. On the other hand, synthetic high molecular compounds synthesized by polymerization reaction of monomers of a raw material are classified into a polyolefin chain, a polyether chain, a polyester chain, a polyamine chain, a polyamide chain, a polyurethane chain, a polysilylether chain and a polysulfone chain depending on a difference in a principal chain structure. A structure in which a carboxyl group is contained on a side chain in these principal chain structures or a structure in which a carboxyl group is contained at a terminal is a basic structure of the synthetic high molecular compound intended by the present invention. Among the synthetic high molecular compounds having these basic structures, those exhibiting water solubility or water dispersibility are the synthetic high molecular compounds intended by the present invention. The principal chain structures of the synthetic high molecular compounds used in the present invention shall not specifically be restricted as long as they have the basic structures described above. In general, one of compounds widely used among the synthetic high molecular compounds exhibiting water solubility or water dispersibility includes a compound having a polyolefin chain as a principal chain. These compounds can be synthesized by radical-polymerizing or ion-polymerizing ethylenically unsaturated compounds. Any methods can be used, but radical polymerization is advantageous from an economical point of view.

The high molecular compounds exhibiting water solubility or water dispersibility having a polyolefin chain as a principal chain include those obtained by polymerizing hydrophilic monomers represented by acrylamides and N-vinyl-2-pyrrolidone and those in which a hydrophilic group is produced by chemical reaction after preparing polymers.

Examples of usable hydrophilic monomers for the former include ethylenical, non-ionic hydrophilic unsaturated compounds and ethylenical, ionic hydrophilic unsaturated compounds.

Given as examples of the ethylenical, nonionic hydrophilic unsaturated compounds are unsaturated carboxylic acid amide compounds such as acrylamide, methacrylamide, N-methylacrylamide, N-methylmethacrylamide, N,N-dimethylacrylamide, N,N-dimethylmethacrylamide, N-ethylacrylamide, N-ethylmethacrylamide, N,N-diethylacrylamide, N,N-diethylmethacrylamide, N-propylacrylamide, N-acryloylpyrrolidine, N-acryloylpiperidine, N-acryloylmorpholine, N,N-di-n-propylacrylamide, N-n-butylacrylamide, N-n-hexylacrylamide, N-n-hexylmethacrylamide, diacetoneacrylamide, N-n-octylacrylamide, N-n-octylmethacrylamide, N-tert-octylacrylamide, N-dodecylacrylamide, N-n-dodecylmethacrylamide, N,N-diglycidylacrylamide, N,N-diglycidylmethacrylamide, N-(4-glycidoxybutyl)acrylamide, N-(4-glycidoxybutyl) methacrylamide, N-(5-glycidoxy-pentyl)acrylamide, N-(6-glycidoxyhexyl)acrylamide, N,N'-methylenebisacrylamide, N,N'-ethylenebisacrylamide, N,N'-hexamethylenebisacrylamide, N-methylolacrylamide, N-methylolmethacrylamide, N-methoxymethylacrylamide, N-methoxymethylmethacrylamide, maleic acid diamide, maleic acid monoamide, fumaric acid diamide, fumaric acid monoamide, itaconic acid diamide and itaconic acid monoamide; N-vinyl-2-pyrrolidone, N-vinyloxazolidone, N-vinyl-5-methyloxazolidone, N-vinylsuccinimide, N-vinylformaldehyde N-vinylacetamide, 2-hydroxyethyl acrylate, 2-hydroxyethyl methacrylate, 3-hydroxypropyl acrylate, 3-hydroxypropyl methacrylate, 2-hydroxypropyl acrylate, 2-hydroxypropyl methacrylate, allyl alcohol and methallyl alcohol.

Among the unsaturated carboxylic acid amide compounds, the compounds represented by the following Formula (1) or (2) are preferred:

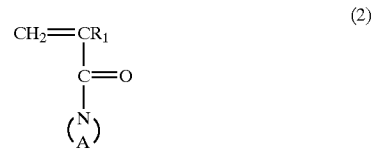

wherein $R_1$ represents a hydrogen atom or methyl group; $R_2$ and $R_3$ each represent independently a hydrogen atom or a linear or branched alkyl group having 1 to 6 carbon atoms; and A represents —$(-CH_2-)_n$— (n represents an integer of 4 to 6) or —$(-CH_2-)_2$—O—$(-CH_2-)_2$—.

Among the ionic compounds of the ethylenical hydrophilic unsaturated compounds, examples of the compounds exhibiting an anionic property include at least one compound selected from the group consisting of unsaturated carboxylic acid compounds, unsaturated sulfonic acid compounds and other anionic unsaturated compounds. Among them, the unsaturated carboxylic acid compound is an essential component in the present invention, and those which can form carboxyl groups by after-reaction including hydrolysis, such as unsaturated carboxylic acid amide compounds and unsaturated carboxylic acid ester compounds may be contained as a copolymerizable component in addition to the unsaturated carboxylic acid compounds, and in those cases a carboxyl group may be formed by after-reaction. The unsaturated carboxylic acid compound is copolymerized in a proportion of usually 0.1 to 80 mole % or 0.1 to 80% by weight, preferably 0.5 to 50 mole % or 0.5 to 50% by weight based on the total amount of the unsaturated compounds.

Given as the unsaturated carboxylic acid compound are acids such as acrylic acid, methacrylic acid, crotonic acid, angelic acid, tiglic acid, 2-pentenic acid, β-methylcrotonic acid, β-methyltiglic acid, α-methyl-2-pentenic acid, β-methyl-2-pentenic acid, maleic acid, fumaric acid, maleic anhydride, itaconic acid, citraconic acid, mesaconic acid, glutaconic acid, α-dihydromuconic acid, 2,3-dimethylmaleic acid, 2-methylglutaconic acid, 3-methylglutaconic acid, 2-methyl-α-dihydromuconic acid and 2,3-dimethyl-α-dihydromuconic acid, and alkali metal salts, ammonium salts and organic amine salts thereof.

Given as the unsaturated sulfonic acid compound are sulfonic acids such as vinylsulfonic acid, styrenesulfonic acid, 2-acrylamide-2-phenylpropane-sulfonic acid, 2-acrylamide-2-methylpropanesulfonic acid, allylsulfonic acid and methallylsulfonic acid, and alkali metal salts, ammonium salts and organic amine salts thereof.

Given as the other anionic unsaturated compound are phosphoric acid esters such as phosphoric acid mono(2-hydroxyethyl)methacrylate ester, and alkali metal salts, ammonium salts and organic amine salts thereof.

Given as examples of the compounds exhibiting an cationic property among the ionic compounds of the ethylenical hydrophilic unsaturated compounds are basic vinyl compounds such as N,N-dimethylaminoethyl acrylate (DA), N,N-dimethylaminoethyl methacrylate (DM), N,N-diethylaminoethyl acrylate, N,N-diethylaminoethyl methacrylate, N,N-dimethylaminopropylacrylamide (DMAPAA) and N,N-dimethylaminopropylmethacrylamide (DMAPMA), and salts thereof, and allylamines such as allylamine, N-methylallylamine, 2-methylallylamine and diallylamine and salts thereof. Further, given are vinyl compounds obtained by quaternarizing DA, DM, DMAPAA and DMAPMA with dimethyl sulfate, alkyl halides such as methyl chloride and methyl bromide, allyl chloride, benzyl halides such as benzyl chloride and benzyl bromide, epihalohydrins such as epichlorohydrin and epibromohydrin and epoxides such as propylene oxide and styrene oxide, and dimethyldiallylammonium chloride.

The ethylenical, hydrophilic unsaturated compounds described above can be copolymerized with ethylenical hydrophobic unsaturated compounds to such an extent that the water solubility or the water dispersibility is not damaged. A copolymerization percentage of the hydrophobic unsaturated compounds can not be specified because it varies depending on the kind of the monomers and a combination of the copolymerizable compounds, and the high percentage allows the water dispersibility to be lost, so that an amount of the hydrophobic unsaturated compounds falls generally in a range of 99 to 0% by weight and has to be controlled to such an extent that a water solubility of the copolymer is not lost.

Examples of the ethylenical, hydrophobic unsaturated compounds include at least one compound selected from the group consisting of aromatic vinyl compounds, vinyl cyanide compounds, diene compounds, unsaturated carboxylic acid ester compounds, vinyl alkyl ether compounds, other vinyl compounds and hydrophobic allyl compounds.

Given as the aromatic vinyl compounds are styrene, α-methylstyrene, α-chlorostyrene, p-tert-butylstyrene, p-methylstyrene, p-chlorostyrene, o-chlorostyrene, 2,5-dichlorostyrene, 3,4-dichlorostyrene, dimethylstyrene and divinylbenzene.

Given as the vinyl cyanide compounds are acrylonitrile, methacrylonitrile and α-chloroacrylonitrile.

Given as the diene compounds are diolefin compounds such as allene, butadiene and isoprene, and chloroprene.

Given as the unsaturated carboxylic acid ester compounds are methyl acrylate, methyl methacrylate, ethyl acrylate, ethyl methacrylate, propyl acrylate, propyl methacrylate, butyl acrylate, butyl methacrylate, 2-ethylhexyl acrylate, 2-ethylhexyl methacrylate, lauryl acrylate, lauryl methacrylate, benzyl acrylate, benzyl methacrylate, cyclohexyl acrylate, cyclohexyl methacrylate, glycidyl acrylate, glycidyl methacrylate, ethylene glycol diacrylate, ethylene glycol dimethacrylate, diethylene glycol diacrylate, diethylene glycol dimethacrylate, triethylene glycol diacrylate, triethylene glycol dimethacrylate, 1,4-butanediol diacrylate, 1,6-hexanediol acrylate, tetraethylene glycol dimethacrylate, 1,3-butylene glycol dimethacrylate, polyethylene glycol (meth)acrylate, methoxypolyethylene glycol (meth)acrylate, ethoxypolyethylene glycol (meth)acrylate, propoxypolyethylene glycol (meth) acrylate, isopropoxypolyethylene glycol (meth)acrylate, phenoxypolyethylene glycol (meth)acrylate, and divinyl compounds such as epoxy acrylates and urethane acrylates.

Given as the vinyl alkyl ether compounds are vinyl methyl ether, vinyl ethyl ether, vinyl isopropyl ether, vinyl n-propyl ether, vinyl isobutyl ether, vinyl 2-ethylhexyl ether and vinyl n-octadecyl ether.

Given as the other vinyl compounds are vinyl esters such as vinyl acetate and vinyl propionate, olefins such as ethylene, propylene, butene and α-olefin, diene compounds such as butadiene, isoprene and chloroprene, olefin halides such as vinyl chloride, vinylidene chloride, vinyl fluoride and vinylidene fluoride, divinyl esters such as divinyl adipate and divinyl sebacate, carboxylic acid dialkyl esters such as acid diethyl fumarate and dimethyl itaconate, maleimide, N-phenylmaleimide and N-cyclohexylmaleimide.

Further, given as the hydrophobic allyl compounds are diallyl isophthalate, diallyl terephthalate, diethylene glycol diallyl carbonate and triallyl cyanurate.

Known polymerization processes, for example, aqueous solution polymerization, precipitation polymerization and emulsion polymerization can be used as a process for producing the polymers of the hydrophilic monomers used in the present invention. Any combination of batch polymerization and semi-batch polymerization may be used, and the polymerization process shall by no means be restricted.

When carrying out radical polymerization, a polymerization solution is usually maintained at a fixed temperature in the presence of a radical polymerization initiator to thereby carry out the polymerization. The temperature does not have to be maintained at the same temperature during the polymerization and may suitably be changed as the polymerization goes on, and it is carried out, if necessary, while heating or cooling. The polymerization temperature varies depending on the kind of the monomers used and the kind of the polymerization initiator and falls generally in a range of 30 to 100° C. in the case of a single initiator. It is lower in the case of a redox base polymerization initiator and generally −5 to 50° C. when carrying out the polymerization in a lump, and it is usually 30 to 90° C. when adding the monomers one after another. The atmosphere in the polymerization vessel shall not specifically be restricted but is preferably substituted with inert gas such as nitrogen gas in order to quickly carry out the polymerization. The polymerization time shall not specifically be restricted and is generally 1 to 40 hours.

Water is used as the polymerization solvent, and organic solvents such as methanol, ethanol, isopropanol, acetone, ethylene glycol and propylene glycol may be used in combination.

The polymerization concentration is 1 to 40% by weight, preferably 2 to 30% by weight in terms of a monomer concentration.

Conventional water-soluble initiators can be used as the radical polymerization initiator. The peroxides include, for example, ammonium persulfate, potassium persulfate, hydrogen peroxide and tert-butyl peroxide. In this case, they can be used alone or can be used in the form of a redox base polymerization initiator as well in combination with reducing agents. Given as the reducing agent are, for example, sulfites, hydrogensulfites, salts of a lower valency ion of iron, copper and cobalt, etc., hypophosphorous acid, hypophosphites, organic amines such as N,N,N',N'-tetramethylethylene-diamine, and reducing sugars such as aldose and ketose. In the case of azo compounds, capable of being used are 2,2'-azobis-2-amidinopropane hydrochloride, 2,2'-azobis-2,4-dimethylvaleronittrile, 4,4'-azobis-4-cyanovaleic acid and salts thereof. Further, the polymerization initiators described above may be used in combination of two or more kinds thereof. An addition amount of the polymerization initiators falls in a range of 0.0001 to 10% by weight, preferably 0.01 to 8% by weight based on the monomers. In the case of the redox bases, an addition amount of the reducing agents is 0.1 to 100% by mole, preferably 0.2 to 80% by mole based on the polymerization initiators.

In polymerization of the hydrophilic monomers, a pH controller and a chain transfer agent may be used, if necessary, for the purpose of controlling the molecular weight and the polymerization speed.

The pH controller includes inorganic bases such as sodium hydroxide, potassium hydroxide and ammonia, organic bases such as ethanolamine, trimethylamine and triethylamine, and salts such as sodium hydrogencarbonate, sodium carbonate, sodium acetate and sodium dihydrogenphosphate.

Used as the chain transfer agent is a mixture comprising at least one selected from isopropyl alcohol, α-thioglycerol, mercaptosuccinic acid, thioglycolic acid, triethylamine and sodium hypophosphite.

Further, compounds such as sodium ethylenediaminetetracetate (EDTA-Na), urea and thiourea may be used in combination for the purpose of masking metal ions or controlling the polymerization speed. Use amounts of the pH controller and the chain transfer agent vary according to use purposes and fall generally in a range of 100 ppm to 10% in the case of the pH controller and 1.0 ppm to 5.0% in the case of the chain transfer agent and other additives based on the weight of the monomers.

The polymers obtained by polymerizing the hydrophilic monomers such as (meth)acrylamide base polymers and vinylpyrrolidone base polymers used in the present invention have a molecular weight, though varying depending on the polymer structures (liner or branched), falling in a range of generally $1.0 \times 10^3$ to $5.0 \times 10^6$. This is because the composite of the present invention is used for various uses, and the molecular weight falls preferably in a range of generally $1.0 \times 10^3$ to $1.0 \times 10^5$ in the uses in which dispersibility of the particles is important, $1.0 \times 10^4$ to $1.0 \times 10^6$ in the uses of various additives and films in which strength is required and $5.0 \times 10^4$ to $5.0 \times 10^6$ in the uses of flocculants, chemicals for paper making and others. The molecular weight of $1.0 \times 10^3$ or less does not provide the stable dispersion because of the low adsorption strength to the inorganic fine particles in addition to a reduction in the characteristics of the polymer itself. On the other hand, the molecular weight of $5.0 \times 10^6$ or more does not provide as well the stable dispersion because cross-linking reaction between the particles takes place preferentially. Further, a carboxyl group amount contained in the polymer falls in a range of generally 0.1 to 80 mole % or 0.1 to 80% by weight, preferably 0.5 to 50 mole % or 0.5 to 50% by weight. Next, an example in which a hydrophilic group is produced by chemical reaction after obtaining the polymer includes polyvinyl alcohol (PVA) and polyvinylamine, and any of high molecular compounds having a carboxyl group in a molecule can be used. Among them, PVA is most preferred. Polyvinyl alcohol base polymers having a carboxyl group in a molecule (carboxyl group-modified polyvinyl alcohol) are used as PVA, and usually used are those obtained by saponifying copolymers of vinyl ester compounds and ethylenically unsaturated carboxylic acids and/or those obtained by radically copolymerizing ethylenically unsaturated carboxylic acids in the presence of polyvinyl alcohol base polymers having a thiol group at the terminals.

Given as the vinyl ester compounds described above are vinyl acetate, vinyl formate, vinyl propionate, vinyl butyrate, vinyl isobutyrate, vinyl pivalate and vinyl caprylate, and vinyl acetate is preferred from an industrial point of view.

Given as the ethylenically unsaturated carboxylic acids described above are unsaturated monocarboxylic acids such as acrylic acid, methacrylic acid, crotonic acid, angelic acid, tiglic acid, 2-pentenic acid, β-methylcrotonic acid, β-methyltiglic acid, α-methyl-2-pentenic acid and β-methyl-2-pentenic acid, unsaturated dicarboxylic acids such as maleic acid, fumaric acid, maleic anhydride, itaconic acid, itaconic anhydride, citraconic acid, citraconic anhydride, mesaconic acid, glutaconic acid, α-dihydromuconic acid, 2,3-dimethylmaleic acid, 2-methylglutaconic acid, 3-methylglutaconic acid, 2-methyl-α-dihydromuconic acid and 2,3-dimethyl-α-dihydromuconic acid, and alkali metal salts, ammonium salts and organic amine salts thereof.

Allowed to be copolymerized in place of the ethylenically unsaturated carboxylic acids are ethylenically unsaturated carboxylic acid esters, ethylenically unsaturated dicarboxylic acid monoesters, ethylenically unsaturated dicarboxylic acid diesters and ethylenically unsaturated carboxylic acid amides, which produce carboxyl groups in saponification reaction. Also, the ethylenically unsaturated carboxylic acids may be copolymerized together with compounds which produce carboxyl groups in saponification reaction thereof. Further, they can be copolymerized as well with other copolymerizable monomers to such an extent that water solubility and stability of the carboxyl group-modified polyvinyl alcohol are not damaged.

The polymerization and saponification methods shall not specifically be restricted, and the carboxyl group-modified polyvinyl alcohol can be produced according to such known processes as disclosed in, for example, Japanese Patent Application Laid-Open No. Sho 53-91995.

The polyvinyl alcohol base polymers having a thiol group at the terminals can be obtained by polymerizing vinyl ester compounds in the presence of a chain transfer agent having a thiol group such as thioacetic acid and then carrying out saponification reaction thereof. In the polymerization, they can be copolymerized as well with other copolymerizable monomers to such an extent that water solubility and stability of the carboxyl group-modified polyvinyl alcohol are not damaged. Radical copolymerization of the ethylenically unsaturated carboxylic acid in the presence of the polyvinyl alcohol base polymer having a thiol group at the terminals allows the carboxyl group-modified polyvinyl alcohol (blocked copolymer) to be produced. In the block polymerization thereof, they can be copolymerized as well with other copolymerizable monomers to such an extent that water solubility and stability of the carboxyl group-modified polyvinyl alcohol are not damaged. An amount thereof varies depending on the kind of the monomers used and falls in a range of generally 1 to 50% by weight based on the vinyl ester compound before saponification reaction.

The copolymerizable monomers include ethylenically unsaturated carboxylic acids, ethylenically unsaturated carboxylic acid esters, ethylenically unsaturated dicarboxylic acid monoesters, ethylenically unsaturated dicarboxylic acid diesters, ethylenically unsaturated carboxylic acid amides, anionic ethylenically unsaturated compounds, cationic ethylenically unsaturated compounds, nonionic hydrophilic ethylenically unsaturated compounds and hydrophobic ethylenically unsaturated compounds.

Given as the ethylenically unsaturated carboxylic acid esters are methyl acrylate, methyl methacrylate, ethyl acrylate, ethyl methacrylate, propyl acrylate, propyl methacrylate, butyl acrylate, butyl methacrylate, 2-ethylhexyl acrylate, 2-ethylhexyl methacrylate, lauryl acrylate, lauryl methacrylate, benzyl acrylate, benzyl methacrylate, cyclohexyl acrylate, cyclohexyl methacrylate, glycidyl acrylate, glycidyl methacrylate, ethylene glycol diacrylate, ethylene glycol dimethacrylate, diethylene glycol diacrylate, diethylene glycol dimethacrylate, triethylene glycol diacrylate, triethylene glycol dimethacrylate, 1,4-butanediol diacrylate, 1,6-hexanediol acrylate, tetraethylene glycol dimethacrylate, 1,3-butylene glycol dimethacrylate, polyethylene glycol (meth)acrylate, methoxypolyethylene glycol (meth)acrylate, ethoxypolyethylene glycol (meth)acrylate, propoxypolyethylene glycol (meth)acrylate, isopropoxypolyethylene glycol (meth)acrylate, phenoxypolyethylene glycol (meth)acrylate, and divinyl compounds such as epoxy acrylates and urethane acrylates.

Given as examples of the ethylenically unsaturated dicarboxylic acid monoesters are maleic acid monoalkyl esters, fumaric acid monoalkyl esters, itaconic acid monoalkyl esters and citraconic acid monoalkyl esters.

Given as examples of the ethylenically unsaturated dicarboxylic acid diesters are maleic acid dialkyl esters, fumaric acid dialkyl esters, itaconic acid dialkyl esters and citraconic acid dialkyl esters.

Capable of being given as examples of the ethylenically unsaturated carboxylic acid amides are acrylamide, methacrylamide, N-methylacrylamide, N-methylmethacrylamide, N,N-dimethylacrylamide, N,N-dimethylmethacrylamide, N-ethylacrylamide, N-ethylmethacrylamide, N,N-diethylacrylamide, N,N-diethylmethacrylamide, N-propylacrylamide, N-acryloylpyrrolidine, N-acryloylpiperidine, N-acryloylhexahydroazepine, N-acryloylmorpholine, N,N-di-n-propylacrylamide, N-n-butylacrylamide, N-n-hexylacrylamide, N-n-hexylmethacrylamide, diacetoneacrylamide, N-n-octylacrylamide, N-n-octylmethacrylamide, N-tert-octylacrylamide, N-dodecylacrylamide, N-n-dodecylmethacrylamide, N,N-diglycidylacrylamide, N,N-diglycidylmethacrylamide, N-(4-glycidoxybutyl)acrylamide, N-(4-glycidoxybutyl)methacrylamide, N-(5-glycidoxy-pentyl)acrylamide, N-(6-glycidoxyhexyl)acrylamide, N,N'-methylenebisacrylamide, N,N'-ethylenebisacrylamide, N,N'-hexamethylenebisacrylamide, N-methylolacrylamide, N-methylolmethacrylamide, N-methoxymethylacrylamide, N-methoxymethylmethacrylamide, maleic acid diamide, maleic acid monoamide, fumaric acid diamide, fumaric acid monoamide, itaconic acid diamide and itaconic acid monoamide.

The anionic ethylenically unsaturated compounds other than the ethylenically unsaturated carboxylic acids described above include ethylenically unsaturated sulfonic acids and other anionic unsaturated compounds, and at least one compound selected from these groups is used.

Given as the ethylenically unsaturated sulfonic acids are sulfonic acids such as vinylsulfonic acid, styrenesulfonic acid, 2-acrylamide-2-phenylpropanesulfonic acid, 2-acrylamide-2-methylpropane-sulfonic acid, allysulfonic acid and methallysulfonic acid, and alkali metal salts, ammonium salts and organic amine salts thereof.

Given as the other anionic unsaturated compounds are phosphoric acid esters such as phosphoric acid mono(2-hydroxyethyl)methacrylate ester, and alkali metal salts, ammonium salts and organic amine salts thereof.

The cationic ethylenically unsaturated compounds include basic vinyl compounds such as N,N-dimethylaminoethyl acrylate (DA), N,N-dimethylaminoethyl methacrylate (DM), N,N-diethylaminoethyl acrylate, N,N-diethylaminoethyl methacrylate, N,N-dimethylaminopropylacrylamide (DMAPAA) and N,N-dimethylaminopropylmethacrylamide (DMAPMA) and salts thereof, and allylamines such as allylamine, N-methylallylamine, 2-methylallylamine and diallylamine and salts thereof. Further, given are vinyl compounds obtained by quaternarizing DA, DM, DMAPAA and DMAPMA with dimethyl sulfate, alkyl halides such as methyl chloride and methyl bromide, allyl chloride, benzyl halides such as benzyl chloride and benzyl bromide, epihalohydrins such as epichlorohydrin and epibromohydrin and epoxides such as propylene oxide and styrene oxide, and dimethyldiallylammonium chloride.

Given as the nonionic hydrophilic ethylenically unsaturated compounds are N-vinyl-2-pyrrolidone, N-vinyloxazolidone, N-vinyl-5-methyloxazolidone, N-vinylsuccinimide, N-vinylformamide N-vinylacetamide, N-vinylcaprolactam, 2-hydroxyethyl acrylate, 2-hydroxyethyl methacrylate, 3-hydroxypropyl acrylate, 3-hydroxypropyl methacrylate, 2-hydroxypropyl acrylate, 2-hydroxypropyl methacrylate, allyl alcohol and methallyl alcohol.

Further, the hydrophobic ethylenically unsaturated compounds other than the ethylenically unsaturated carboxylic acid esters and the vinyl ester compounds include at least one compound selected from the group consisting of aromatic vinyl compounds, vinyl cyanide compounds, diene compounds, vinyl alkyl ether compounds, other vinyl compounds and hydrophobic allyl compounds.

Given as the aromatic vinyl compounds are styrene, α-methylstyrene, α-chlorostyrene, p-tert-butylstyrene, p-methylstyrene, p-chlorostyrene, o-chlorostyrene, 2,5-dichlorostyrene, 3,4-dichlorostyrene, dimethylstyrene and divinylbenzene.

Given as the vinyl cyanide compounds are acrylonitrile, methacrylonitrile and α-chloroacrylonitrile.

Given as the diene compounds are diolefin compounds such as allene, butadiene and isoprene, and chloroprene.

Given as the vinyl alkyl ether compounds are vinyl methyl ether, vinyl ethyl ether, vinyl isopropyl ether, vinyl n-propyl ether, vinyl isobutyl ether, vinyl 2-ethylhexyl ether and vinyl n-octadecyl ether.

Given as the other vinyl compounds are olefins such as ethylene, propylene, butene and α-olefin, olefin halides such as vinyl chloride, vinylidene chloride, vinyl fluoride and vinylidene fluoride, divinyl esters such as divinyl adipate and divinyl sebacate, carboxylic acid dialkyl esters such as diethyl fumarate and dimethyl itaconate, maleimide, N-phenylmaleimide and N-cyclohexylmaleimide.

Given as the hydrophobic allyl compounds are diallyl isophthalate, diallyl terephthalate, diethylene glycol diallyl carbonate and triallyl cyanurate.

A degree of polymerization of the carboxyl group-modified polyvinyl alcohol used in the present invention falls in a range of generally 100 to 5000, preferably 200 to 3000; a degree of saponification thereof falls in a range of 60 to 100 mole % based on the vinyl ester compound before saponification; and a carboxyl group content thereof falls in a range of 0.05 to 50 mole %, preferably 0.1 to 30 mole %.

Those having the forms of so-called synthetic latex and emulsion are included as well in the water-dispersible synthetic high molecular compounds. Among those called polybutadiene latex, styrene-butadiene base latex, acrylonitrile-butadiene base latex, methyl methacrylate-butadiene base latex, 2-vinylpyridine-styrene-butadiene latex, chloroprene latex, isoprene latex, polystyrene emulsion, urethane emulsion, acryl emulsion, vinyl acetate base emulsion, vinyl acetate-ethylene (EVA) base emulsion, acrylate-styrene base emulsion, vinyl chloride latex, vinylidene chloride latex and epoxy base emulsion, those which are modified with a carboxyl group correspond to the water-dispersible synthetic high molecular compound of the present invention.

The synthetic high molecular compounds having a carboxyl group preferably used in the present invention are preferably the polymers of the ethylenically unsaturated compounds, particularly (meth)acrylamide base polymers, carboxyl group-modified polyvinyl alcohols and vinylpyrrolidone base polymers, and further preferred are:

(1) (meth)acrylamide base polymers which are polymers of 1 to 100% by weight of ethylenically unsaturated carboxyl acid amide compounds with 0 to 99% by weight of copolymerizable ethylenically unsaturated compounds, (2) carboxyl group-modified polyvinyl alcohols which are produced by saponifying polymers of ethylenically unsaturated carboxyl acids with vinyl acetate, and (3) vinylpyrrolidone base polymers which are polymers of 1 to 99.9% by weight of N-vinyl-2-pyrrolidone with 0.1 to 99% by weight of copolymerizable ethylenically unsaturated compounds.

The water slightly soluble inorganic fine particles according to the present invention shall not be restricted as long as they have a particle diameter of 500 nm or less, and they are preferably fine particles of compounds of a second group element in the periodic table, more preferably those obtained by reacting compounds of a second group element in the periodic table with at least one compound selected from organic acids, inorganic acids and salts thereof. The second group element in the periodic table includes beryllium, magnesium, calcium, strontium, barium and radium, and because of similar chemical properties thereof, at least one element selected from them can be used. Among them, magnesium, calcium, strontium and barium are preferred. Further, calcium is more preferred.

A liquid phase synthetic process is preferred as a synthetic process for the inorganic fine particles. It is a so-called precipitation process, and the water slightly soluble inorganic fine particles are synthesized by reacting an aqueous solution or a suspension of water-soluble or slightly soluble compounds of a second group element in the periodic table with organic acids, inorganic acids and salts thereof. As called a precipitation process, it is a process in which the water slightly soluble inorganic fine particles produced are usually precipitated, filtered and then dried or thermally decomposed to thereby obtain powder. In the present invention, the preceding water-soluble or water-dispersible synthetic high molecular compound having a carboxyl group is allowed to be present, whereby prepared is the organic polymer/inorganic fine particle-dispersed aqueous solution which is excellent in dispersion stability and in which the inorganic fine particles are homogeneously dispersed in the form of colloid without precipitating. It is not necessarily made completely clear why such organic polymer/inorganic fine particle-dispersed aqueous solution having excellent dispersion stability is prepared. It is suggested by experimental results obtained by the present inventors that a second group element in the periodic table constituting the inorganic fine particle is combined with a carboxyl group contained in the synthetic high molecular compound by ionic interaction. It is given as reasons therefor that this fact inhibits crystal growth and does not allow the particle diameter to grow large to 500 nm or more and that coagulation between the particles is inhibited by virtue of protective colloidal action of the combined high molecular compound.

The water slightly soluble inorganic fine particles according to the present invention has a solubility of generally 3.0 (% by weight) or less in water at 20° C., and water-insoluble inorganic fine particles are included as well. The compounds vary depending on the kind of the second group elements in the periodic table, and examples thereof include, hydroxides, fluorides, carbonates, oxalates and phosphates in the case of magnesium, fluorides, sulfates, phosphates, carbonates, silicates, oxalates and hydroxides in the case of calcium, fluorides, carbonates, oxalates, sulfates, phosphates and hydroxides in the case of strontium, and carbonates, sulfates, phosphates and oxalates in the case of barium.

Examples of the compounds of a second group element in the periodic table used for synthesizing the water slightly soluble inorganic fine particles according to the present invention include at least one compound selected from magnesium acetate, magnesium carbonate, magnesium chloride, magnesium silicofluoride, magnesium hydroxide, magnesium oxide, magnesium nitrate, magnesium sulfate, calcium acetate, calcium dihydrogenphosphate, calcium lactate, calcium citrate, calcium hydroxide, calcium carbonate, calcium chloride, calcium nitrate, calcium sulfate, calcium thiosulfate, strontium hydroxide, strontium carbonate, strontium nitrate, strontium chloride, barium acetate, barium chloride, barium nitrate, barium sulfate, barium hydroxide and barium fluoride.

The organic acids, the inorganic acids and the salts thereof used in the present invention may be any ones as long as they react with the compounds of second group element in the periodic table to form the water slightly soluble inorganic fine particles. Among them, oxo-acids, halohydric acids and salts thereof are preferred.

Examples of the oxo-acids include boric acid, metaboric acid, carbonic acid, isocyanic acid, fulminic acid, ortho-silicic acid, metasilicic acid, nitric acid, nitrous acid, phosphoric acid (orthophosphoric acid), pyrophosphoric acid (diphosphoric acid), metaphosphoric acid, phosphonic acid (phosphorous acid), diphosphonic acid (diphosphorous acid), phosphinic acid (hypophosphorous acid), sulfuric acid, disulfuric acid, thiosulfuric acid, sulfurous acid, chromic acid, dichromic acid, perchrolic acid, formic acid, acetic acid, propionic acid, butyric acid, oxalic acid, malonic acid, succinic acid, glutaric acid, adipic acid, maleic acid, fumaric acid, lactic acid, malic acid, tartaric acid, benzoic acid and phthalic acid.

Examples of the halohydric acids include hydrofluoric acid, hydrochloric acid, hydrobromic acid and hydroiodic acid.

Examples of the salts of the oxo-acids and the halohydric acids include alkali metal salts, alkaline earth metal salts, ammonium salts and organic amine salts thereof.

As an inorganic component for animal bones and shells, calcium carbonate which is contained in shells and the like and calcium phosphate which is contained in bones, teeth, scales and the like are principal structural components for organic/inorganic composites existed in organisms. Among the water slightly soluble fine particle of the present invention, calcium compounds including these calcium carbonate and calcium phosphate are particularly suitably used since they have high affinity with organic substances.

A case where the water slightly soluble inorganic fine particle is calcium phosphate shall be described below in detail, but merely the raw materials to be used are different in the case of the calcium compounds, and the same fundamental procedure can be employed. Also, in the case of compounds of other second group element, merely the raw materials to be used are different, and the same procedure can be applied.

In calcium phosphate contained in the dispersed aqueous solution of the present invention, the total weight of a part originating in phosphoric acid and a calcium atom accounts for 50% by weight or more. Examples thereof include apatite compounds such as hydroxyaptite, fluoroapatite, chloroapatite, carbonate-containing apatite, magnesium-containing apatite and iron-containing apatite, and tricalcium phosphate.

The apatite compound included as calcium phosphate in the present invention has a basic composition represented by $M_x(RO_4)_yX_z$. In the case where the M site is a calcium ion ($Ca^{2+}$) and the $RO_4$ site is a phosphoric acid ion ($PO_4^{3-}$) and where the X site is a hydroxide ion ($OH^-$), x, y and z are each x=10, y=6 and z=2, and it is a compound which is usually called hydroxyaptite. Th respective sites of M, $RO_4$ and X can be substituted with various ions and can be vacancies. The substitution amount and the vacancy amount vary depending on the kind of the ions, and if the total weight of the part originating in phosphoric acid and a calcium atom accounts for 50% by weight or more, the sites may be substituted with various ions or may be vacancies.

If the total weight of the part originating in phosphoric acid and a calcium atom is less than 50% by weight, characteristics as calcium phosphate are lost in a certain case, and therefore it is not preferred. The M site is basically $Ca^{2+}$, and examples of the substitutable ion species include $H^+$, $Na^+$, $K_{30}$, $H_3O^+$, $Sr^{+2}$, $Ba^{+2}$, $Cd^{+2}$, $Pb^{+2}$, $Zn^{+2}$, $Mg^{+2}$, $Fe^{+2}$, $Mn^{+2}$, $Ni^{+2}$, $Cu^{+2}$, $Hg^{+2}$, $Ra^{+2}$, $Al^{+3}$, $Fe^{+3}$, $Y^{+3}$, $Ce^{+3}$, $Nd^{+3}$, $La^{+3}$, $Dy^{+3}$, $Eu^{+3}$ and $Zr^{+4}$. The M site is basically $PO_4^{3-}$, and examples of the substitutable ion species include $SO_4^{2-}$, $CO_3^{2-}$, $HPO_4^{2-}$, $PO_3F^{2-}$, $AsO_4^{3-}$, $VO_4^{3-}$, $CrO_4^{3-}$, $BO_3^{4-}$, $SiO_4^{4-}$, $GeO_4^{4-}$, $BO_4^{5-}$, $AlO_4^{5-}$, and $H_4O_4^{4-}$. Examples of molecules and ion species coming into the X site include $OH^-$, $F^-$, $Cl^-$, $Br^-$, $I^-$, $O^{2-}$, $CO_3^{2-}$ and $H_2O$.

Calcium carbonate which is contained in the dispersed aqueous solution of the present invention has a particle diameter of 500 nm or less. If the particle diameter exceeds 500 nm, the particles are liable to settle and separate from the dispersed aqueous solution, so that the dispersed aqueous solution is lacking in stability. Accordingly, such a diameter is not suitable. A crystal structure of calcium carbonate may be any structure and may be amorphous as well. Further, a shape of calcium phosphate shall not specifically be restricted and may be any one such as spherical, acicular, columnar and amorphous. The particle diameter distribution shall not specifically be restricted as long as the particle diameter is 500 nm or less. The particle diameter used here is a major axis diameter of the particle.

In a process for producing (compounding) the water-soluble or water-dispersible high molecular compound containing a carboxyl group/calcium phosphate fine particle-dispersed aqueous solution, calcium phosphate is particularly preferably produced in the presence of the water-soluble or water-dispersible high molecular compound containing a carboxyl group in order to obtain the dispersed solution having excellent dispersion stability, and the present invention is characterized by that point. The process for producing calcium phosphate may be any production process as long as it can be produced in the presence of the water-soluble or water-dispersible high molecular compound containing a carboxyl group. A so-called wet process (liquid phase process/precipitation process) is preferred. The wet process is a process in which a calcium compound (suspended) aqueous solution is mixed with phosphoric acid or a phosphate aqueous solution to thereby synthesize calcium phosphate, and usually employed is either of a system in which both solutions are dropwise added at the same time or a system in which one solution is dropwise added to another solution. The dropping time shall not specifically be restricted and is generally 5 minutes to 24 hours. The reaction solution is ripened, if necessary, after finishing dropwise adding.

The water-soluble or water-dispersible high molecular compound containing a carboxyl group may be present in a reaction solution in which calcium phosphate is produced and may be mixed in either of a calcium compound (suspended) aqueous solution or phosphoric acid or a phosphate aqueous solution or may be mixed in both solutions. It may be added continuously or intermittently to a reactor independently from both the solutions. However, in the case where the high molecular compound contains the parts liable to be alkali-hydrolyzed, for example, in the case where compounded is carboxyl group-modified polyvinyl alcohol having a large content (generally 5 to 60 mole %) of a non-saponified part, attentions have to be paid to using a substance having a high alkalinity such as calcium hydroxide as the calcium source. For example, mixing of calcium hydroxide with the carboxyl group-modified polyvinyl alcohol causes hydrolytic reaction of the non-saponified parts as side reaction, so that it becomes a problem in a certain case. In such case, a portion of phosphoric acid equivalent to an amount of calcium hydroxide consumed by the hydrolytic reaction becomes excessive, so that a reduction in a pH of the reaction solution is brought about and calcium phosphate is incompletely produced. In addition thereto, compounding becomes inferior, and separation and setting take place in the reaction solution in a certain case. This problem can be solved by adding dropwise both of calcium hydroxide and the carboxyl group-modified polyvinyl alcohol or one to the other. In the case a production reaction of calcium phosphate takes place preferentially, so that the side reaction can be inhibited. This method makes it possible to produce a carboxyl group-modified polyvinyl alcohol containing a non-saponified part/calcium phosphate-dispersed aqueous solution. If influence exerted by sodium acetate produced by saponification does not cause a problem, an amount of alkali equivalent to the non-saponified part can be added to the carboxyl group-modified polyvinyl alcohol to carry out saponification reaction in advance, and then the compounding reaction may be carried out, but carboxyl group-modified polyvinyl alcohol of a completely saponified type is preferably used since influence such as coloring caused by impurities can be controlled. However, as is the case with the (meth)acrylamide base polymer, those producing a carboxyl group by hydrolytic reaction may rather positively cause a hydrolytic reaction in compounding reaction in a certain case.

The calcium salts used for the synthesis include calcium chloride, calcium nitrate, calcium acetate, calcium hydroxide, calcium carbonate and calcium sulfate·dihydrate. The phosphates include ammonium dihydrogenphosphate, diammonium hydrogenphosphate and sodium and potassium salts thereof other than ammonium salts. Organic or inorganic salts other than the intended compounds, which are by-produced as the reaction goes on, have to be removed depending on uses, and in such case, the salts are removed by known methods such as dialysis. When calcium phosphate is the intended compound, by-produced salts are not produced if calcium hydroxide and phosphoric acid are raw materials, and therefore they are particularly preferred. Further, it is known that among calcium phosphates, those having an apatite structure can be substituted, as described above, with various ions because of flexibility of the structure, and compounds containing ion species other than calcium and phosphoric acid can be used as well, if necessary, in combination.

A weight ratio of the water-soluble or water-dispersible high molecular compound containing a carboxyl group to calcium phosphate falls in a range of 10:90 to 99.99:0.01, preferably 20:80 to 99.99:0.01 and more preferably 30:70 to 99:1. If an amount of calcium phosphate is less than 0.01%, an effect of adding calcium phosphate runs short. On the other hand, if it exceeds 90%, the dispersion stability becomes inferior, and settling and separation are liable to be caused, so that the homogeneous composite can not be formed. Accordingly, such a amount is not preferable.

Usually, the reaction solution is maintained at a prescribed temperature to thereby carry out the reaction. The temperature does not have to be maintained at the same temperature during the reaction and may suitably be changed as the reaction goes on, and the reaction is carried out, if necessary, while heating or cooling. A size of the calcium phosphate particles produced is changed depending on the reaction temperature, and therefore the particle diameter can be changed by changing the reaction temperature, which results in making it possible to control transparency of a film prepared from the dispersed aqueous solution. The reaction temperature falls generally in a range of 5 to 95° C. The atmosphere in the reactor shall not specifically be restricted, and the reaction is usually carried out in the air, but it is better to replace the reactor with an inert gas such as nitrogen gas in order to control the composition of calcium phosphate. The synthesis time shall not specifically be restricted and is generally 1 to 120 hours totaling dropping and ripening time.

A stirring method shall not specifically be restricted as long as it is a method for homogeneously mixing, and examples thereof include a method by rotation and a method by a supersonic wave. When using a batch reactor with stirring blades, the stirring speed falls usually in a range of 30 to 10000 rpm, though can not absolutely be determined since the shape of the stirring blades and a viscosity of the solution exert an influence on it.

Water is used as the reaction solvent, and allowed to be used in combination are organic solvents such as methanol, ethanol, isopropanol, acetone, ethylene glycol, propylene glycol and glycerin.

The concentration in synthesizing shall not specifically be restricted and falls generally in a range of 0.5 to 60% by weight, preferably 1 to 50% by weight totaling the solid content of calcium phosphate and the water-soluble or water-dispersible high molecular compound containing a carboxyl group. If the concentration exceeds 50% by weight, a viscosity of the dispersed solution is elevated, and handling becomes difficult in a certain case.

Calcium phosphate produced is different in a species depending on the pH in reacting, and therefore when producing the specific species, the reaction is carried out while controlling the pH in a certain case. The pH can be controlled by ammonia gas, aqueous ammonia, sodium hydroxide and potassium hydroxide. In particular, (1) when the intended compound is dissolved by a change in the pH and (2) when the composite is separated according to a change in a dissociation state of a carboxyl group, the pH has to be strictly controlled. For example, in the case of hydroxyapatite (calcium phosphate), alkali is suitably added after the reaction so that the pH is not lowered to 5 or less because of the reason of (2).

The water-soluble or water-dispersible high molecular compound containing a carboxyl group/calcium phosphate fine particle-dispersed aqueous solution thus obtained, which has excellent stability, is a homogeneous emulsion solution and does not cause settling and separation even after left standing for long time. The solution having excellent stability described in this case means those in which a content of solids settled or separated after produced exclusive of settled particles (settled after left standing for a night) existed immediately after produced is 1% by weight or less when one month passed, or those which do not cause settling and separation even by carrying out centrifugal separation at 2000 rpm for 10 minutes.

Also when the water slightly soluble inorganic fine particle is calcium carbonate, the solution is produced by the same method as in calcium phosphate. In this case, the same raw materials as those used for calcium phosphate can be used as the calcium source, and suitably used as the carbonate source are carbon dioxide, sodium carbonate, sodium hydrogencarbonate, potassium carbonate, potassium hydrogencarbonate and ammonium carbonate. A combination of calcium hydroxide and carbonic acid (carbon dioxide) is preferred in order to prevent by product salts from being produced as is the case with calcium phosphate.

The water-soluble or water-dispersible high molecular compound containing a carboxyl group/calcium phosphate composite of the present invention, which has excellent transparency, is produced in the form of a solid by removing water from the water-soluble or water-dispersible high molecular compound containing a carboxyl group/calcium phosphate fine particle-dispersed aqueous solution thus obtained, which has excellent dispersion stability. The composite can be processed into an optional shape such as film, sheet, powder, foamed matter and string according to uses by means of known methods and apparatuses.

Further, it can be processed as well into a gelatinous composite by a method in which a cross-linking structure is physically formed by a change in a temperature and a method in which a cross-linking agent is used to form a cross-linking structure by a chemical bond (ionic bond and covalent bond).

When processed into, for example, a film, the film can be produced by coating the stable dispersed aqueous solution described above as it is or after subjecting it to concentration treatment and pH controlling and adding, if necessary, a known plasticizer such as ethylene glycol and glycerin and additives such as a cross-linking agent, a thickener, a filler, a colorant, an antioxidant, a UV absorber and a heat-stabilizer on a substrate such as glass, quartz, metal, ceramics, plastic and rubber, a roll or a belt to be formed and, if necessary, it is subjected to treatments such as heating, reducing pressure, blowing the air, irradiation with an IR ray and irradiation with a microwave to vaporize water and/or the water based solvent. The coating method shall not specifically be restricted and includes a flow coating method, a dipping method and a spraying method, and capable of being used are known coaters such as a bar coater, a spin coater, a knife coater, a blade coater, a curtain coater, a gravure coater and a spray coater. The coating thickness (thickness before drying) is generally 1 µm to 10 mm and can optionally be set according to selection of the coating method. The temperature for vaporizing water and/or the water based solvent falls in a range of 0 to 150° C., and it is vaporized at an atmospheric pressure or under reduced pressure. In this case, dried air or dried nitrogen can be allowed to flow to shorten the drying time. Further, when accelerating the cross-linking reaction for the purpose of endowing the film with water resistance, the film is subjected to heat treatment at 40 to 200° C. for several seconds to several ten minutes. When peeling this film from the substrate for using, a plastic-made substrate has better releasability. When using the other substrates, it is recommendable to coat, if necessary, known releasing agents in advance on the respective substrates. The film thus produced is characterized by having excellent transparency. This shows that the calcium phosphate fine particles have a size which is not larger than a wavelength in a visible ray area and that the respective particles are homogeneously dispersed in the polymer matrix without causing coagulation. The transparency can quantitatively be evaluated by a visible ray transmittance in 400 nm and 700 nm. In this case, the term of having excellent transparency means a light transmittance of 50% or more at a wavelength of 700 nm in a film thickness of 30 to 300 µm. This film turns cloudy when absorbing moisture and turns transparent when dried, and this change is reversible. The term of having excellent transparency is mentioned under a dry condition (moisture content: 10% by weight or less).

Further, this transparent film can be redispersed in water if not subjected to specific treatment such as cross-linking. The redispersibility is notably exhibited in the case of a (meth)acrylamide base polymer. Uncertain is the reason why what has been once turned into a film as described above has such excellent dispersion stability that it can be redispersed, and it is estimated that this fact supports the presence of adsorption action originating in an ionic bond between the polymer and the particles as described above and protective colloidal action.

The film has a very high hydrophilicity and therefore causes a problem on water resistance in a certain case. In such case, (1) a method of physically preventing water and humidity from penetrating and (2) a method of endowing the film with water resistance in preparing it are available. A method of laminating a hydrophobic film is effective as the method (1). The method (2) includes a method providing the water-soluble or water-dispersible high molecular compound containing a carboxyl group/inorganic fine particle-dispersed aqueous solution itself with a cross-linking property and a method of adding a water resistance-providing agent. To be specific, the former includes a method (I) of introducing a cross-linking functional group by copolymerization in producing the water-soluble or water-dispersible high molecular compound containing a carboxyl group and a method (II) of adding a cross-linking agent which can be reacted with the water-soluble or water-dispersible high molecular compound containing a carboxyl group. In the method (I), a carboxyl group, an amino group, an epoxy group, a hydroxyl group and an oxazoline group are used as the functional group, and the water resistance is derived by a reaction between these functional groups themselves or a cross-linking reaction caused by polyvalent metal ions. The cross-linking agent in the method (II) includes formalin, a urea-formalin resin, a polyamide-polyamine resin and modified products thereof. Also, the latter includes a method of mixing the dispersed aqueous solution with a curable emulsion resin, and known emulsions of an acryl base, a polyester base and a polyurethane base can be used.

Capable of being used as a method for turning the composite into powder from the water-soluble or water-dispersible high molecular compound containing a carboxyl group/inorganic fine particle-dispersed aqueous solution is a method in which the solvent is vaporized, as is the case with the film processing, directly from the dispersed aqueous solution of the composite as it is or after subjecting it to concentration treatment and pH controlling or adding, if necessary, a known plasticizer such as ethylene glycol and glycerin and additives such as a cross-linking agent, a thickener, a filler, a colorant, an antioxidant, a UV absorber and a heat-stabilizer by means of spray drying and freeze drying or a method in which solid-separating treatment is carried out by using an organic solvent such as methanol, which is miscible with water but does not dissolve the composite or a compound having a high salting-out effect such as sodium sulfate and in which it is turned into powder after drying. However, the former is preferred in light of the object of the present invention.

The other shape processings can be carried out, as is the case with the film processing, by known methods using the dispersed aqueous solution of the composite as it is or after subjecting it to concentration treatment and pH controlling or adding, if necessary, a known plasticizer such as ethylene glycol and glycerin and additives such as a cross-linking agent, a thickener, a filler, a colorant, an antioxidant, a UV absorber and a heat stabilizer.

It is known that the water-soluble or water-dispersible high molecular compound containing a carboxyl group/ inorganic fine particle composite of the present invention is a polymer material having high safety, particularly in the case of polyvinyl alcohol and polyvinylpyrrolidone. When a material for compounding is calcium phosphate or calcium carbonate, the composite is characterized by the point of "a polymer-compounded material in which particles having high biological affinity are homogeneously dispersed in a nanometer size" and has various uses. These composites can be processed into various shapes as described above and therefore are very useful materials particularly as medical or cosmetic materials. They can be used for artificial bone materials, bone fillers, dental materials, DDS carriers and dermatopathy remedies as medical materials. Further, as described above, these composite films are characterized in that they become cloudy when absorbing moisture and are turned into transparent films when dried. This is owing to scattering originating in hydration of the particle and is not a phenomenon which is limited to a film. Making use of this property makes it possible to apply them to cosmetics having a high UV-shielding property, window materials in which the transparency is reversibly changed by humidity and humidity sensors.

Thus, included as well in the present invention are those containing the preceding high molecular compound/ inorganic fine particle-dispersed aqueous solution having excellent dispersion stability and cosmetics containing the high molecular compound/inorganic fine particle composite having excellent transparency.

The water-soluble or water-dispersible high molecular compound containing a carboxyl group/inorganic fine particle composite of the present invention is improved in a tensile strength, a hardness, a thermal characteristic and a gas barrier property as compared with those of the film of the polymer alone before compounding. For example, polyvinyl alcohol is known as a material having a high gas barrier property, but the compounding elevates the barrier property to a large extent as compared therewith. Making use of these characteristics can be achieved by preparing a multilayer film in which polyvinyl alcohol having inferior water resistance is used for the intermediate layer. In uses in which the water resistance is not so much problem, a polyvinyl alcohol/inorganic fine particle composite may be subjected, if necessary, to water resistance treatment of coating a water resistant polymer on the surface layer. Further, there is the advantage that the film itself is increased in a strength, while various base materials are coated or impregnated with it, whereby it can be used as well for the purpose to elevate a strength of the base materials. Among them, application to paper is useful, and paper-making chemicals are included as well in the present invention.

The paper-making chemical of the present invention is obtained from the preceding high molecular compound/ inorganic fine particle-dispersed aqueous solution having excellent dispersion stability. Also, the paper-making chemical of the present invention is a paper-making chemical comprising the water-soluble or water-dispersible high molecular compound (A) containing a carboxyl group and the water slightly soluble inorganic fine particle (B) having a particle diameter of 500 nm or less obtained by reacting a compound of a second group element in the periodic table with at least one compound selected from organic acids, inorganic acids and salts thereof in a proportion of (A):(B)= 10:90 to 99.99:0.01 (weight ratio).

Paper obtained by using the paper-making chemical of the present invention is improved in a paper-strengthening property. In particular, the paper strength is elevated to a large extent by coating (externally adding) the paper-making chemical of the present invention on the surface of paper. A concentration of the coating liquid in coating on paper falls in a range of 0.01 to 20.0% by weight, preferably 0.10 to 10.0% by weight. The coating amount thereof falls in a range of 0.001 to 20.0 g/m$^2$, preferably 0.005 to 10.0 g/m$^2$. Coating on paper is carried out by means of conventional methods such as impregnation, a size press, a gate roll coater, a calender, a blade coater and spraying. The drying temperature after coating may be a temperature at which water is vaporized and falls preferably in a range of 100 to 180° C. Further, the paper-making chemicals of the present invention can elevate further more the surface strength and the internal strength by combining with known surface coating chemicals of a starch base, a carboxymethyl cellulose base, a PVA base and a PAM base.

The paper-making chemical of the present invention can be fixed on pulp by interaction with aluminum sulfate, aluminum chloride, sodium aluminate and water-soluble polymers having a cation group such as polyethylenimine, Mannich-modified products and Hofmann-modified products of polyacrylamide, polyalkylenepolyamine and cationic starch, so that it can also be used as an internally added chemical for paper making. When used as an internally added chemical, it is added in a proportion of 0.01 to 5.0% by weight, preferably 0.05 to 2.0% by weight based on the weight of pulp and may be added in the same place as in conventional internally added chemicals, such as a stuff box and a machine chest.

The paper-making chemical of the present invention may be mixed, if necessary, with a defoaming agent, a preservative, a rust preventive and a lubrication preventive or may be used in combination with them in using.

It is known that calcium phosphate and calcium carbonate have high affinity not only to organisms but also organic substances. Calcium phosphate fine particles of a nanometer size contained in the composite of the present invention do not form a coagulation structure unlike conventional ones and are homogeneously dispersed in the composite, so that the specific surface area is elevated to a large extent, and the interaction with organic substances contained in water grows large. Accordingly, the composite can suitably be used for ink jet recording material, and a chemical for an ink jet recording sheet is included as well in the present invention.

The chemical for an ink jet recording sheet of the present invention is obtained from the preceding high molecular compound/inorganic fine particle-dispersed aqueous solution having excellent dispersion stability. Also, the chemical for an ink jet recording sheet of the present invention is an ink jet recording sheet chemical comprising the water-soluble or water-dispersible high molecular compound (A) containing a carboxyl group and the water slightly soluble inorganic fine particle (B) having a particle diameter of 500 nm or less obtained by reacting a compound of a second group element in the periodic table with at least one compound selected from organic acids, inorganic acids and salts thereof in a proportion of (A):(B)=10:90 to 99.99:0.01 (weight ratio).

The chemical for an ink jet recording sheet of the present invention has a very excellent characteristic against a yellowing property that paper discolors yellow during storage over a long period of time, which is exhibited by conventionally used inorganic fillers.

The chemical for an ink jet recording sheet of the present invention can produce an ink jet recording sheet having excellent yellowing resistance by coating on a sheet base material. The sheet base material shall not specifically be restricted and includes pulp and paper using pulp as a principal raw material, recycled paper, synthetic paper, cloth, nonwoven fabric, films and plates using polyolefins, acryl base polymers and polyesters as a principal raw material, and glass plates.

The chemical for an ink jet recording sheet of the present invention can be used not only alone but also, if necessary, in combination with known inorganic fillers, organic fillers, binders and other various additives as long as the yellowing resistance is not damaged. The inorganic fillers include calcium carbonate, kaolin, clay, talc, mica, calcium sulfate, barium sulfate, titanium dioxide, zinc oxide, zinc sulfide, zinc carbonate, satin white, zeolite, smectite, diatomaceous earth, calcium silicate, aluminum silicate, amorphous silica and alumina, and the organic fillers include plastic pigments of a styrene base and a urea resin base. The binders include polyvinyl alcohol, cellulose derivatives such as carboxymethyl cellulose and hydroxyethyl cellulose, polyvinylpyrrolidone, water-soluble acryl resins, casein, soybean protein, gelatin, starch, styrene-butadiene base latex and acryl base emulsion. The other additives include ink fixing agents, water resistance-providing agents, dot-controlling agents, humectants, pH controlling agents, fluorescent whitening agents, antioxidants, UV absorbers, preservatives, defoaming agents, thickeners, pigment dispersants and mold releasing agents.

Means for coating the chemical for an ink jet recording sheet of the present invention on a base material shall not specifically be restricted and can suitably be selected according to the purposes. Used are various known methods, for example, a blade coater, a roll coater, an air knife coater, a bar coater, a curtain coater, a spray coater, a size press and impregnation. Smoothing treatment can be carried out, if necessary, by means of a smoothing apparatus such as a super calender and a soft calender. The coating layer may have a lamination structure having two or more layers according to the purposes. A coating amount of the coating layer shall not specifically be restricted and is preferably 3 to 30 g/m$^2$ in terms of a solid content of the composite. A coating amount of more than 30 g/m$^2$ does not further elevate the characteristics, and that of less than 3 g/m$^2$ is likely to provide the unsatisfactory ink absorptivity.

The water-soluble or water-dispersible high molecular compound containing a carboxyl group/calcium phosphate composite of the present invention is characterized by having high transparency and containing calcium phosphate having high affinity to organic substances and organisms in a wide proportion. Accordingly, it can be used over the broad fields such as, in addition to those described above, coating materials, adhesives, pigment binders, ceramics binders, fiber processing agents, emulsifiers, fillers for chromatography, filter materials, resin modifiers, waste water treating agents, fungicides, flame retardants, sensor materials for humidity and carbon dioxide, cell culture medium, separation membranes and food additives.

EXAMPLES

The present invention shall be explained below in details with reference to examples, but the present invention shall not be restricted by the examples. Percentages used in the following examples show weight basis unless otherwise described.

The viscosity is a value measured by means of a B type viscometer (manufactured by Tokimec Inc.).

Analysis by X-ray diffraction was carried out by means of RINT X-ray Diffractometer (manufactured by Rigaku Corporation).

FT-IR was determined by means of an FT/IR-8300 Fourier transform infrared spectrophotometer manufactured by JASCO Corporation.

The light transmittance was determined by means of a Shimadzu automatic spectrophotometer (manufactured by Shimadzu Corporation).

Transmission electron microscope (TEM) observation was carried out by means of an H-300 type Hitachi electron microscope (manufactured by Hitachi, Ltd.) and a JEM-2010 type transmission electron microscope (manufactured by JEOL, Ltd.).

The ultramicrohardness was determined by means of a Shimadzu dynamic ultramicrohardness tester DUH-201 type (manufactured by Shimadzu Corporation).

Polymer Production Example 1

A four neck flask equipped with a stirrer, a reflux condenser, a thermometer and a nitrogen gas-inlet tube was charged with 30.00 g of acrylamide, 0.15 g of sodium hypophosphite monohydrate and 266.85 g of distilled water, and they were mixed and dissolved, followed by adjusting the PH to 4.5. The solution was controlled to a temperature of 80° C. while allowing nitrogen gas to flow from the upper part of the solution level at a fixed flow rate, and then 3.0 g of an aqueous solution dissolving 0.30 g of ammonium persulfate was added thereto to carry out polymerization reaction for 3 hours. The solution was cooled down to 30° C. or lower to terminate the reaction to obtain a (meth) acrylamide base polymer (Polymer A) aqueous solution (non-volatile matter content: 11.12%) having a Brookfield viscosity of 114.4 mPa·s at 25° C.

The weight average molecular weight was 337,000.

Polymer Production Examples 2 to 5

Acrylamide, copolymerizable monomers, the polymerization initiator and the chain transfer agent were used in the amounts described in Table 1 to carry out the reaction in the same manner as in Polymer Production Example 1, whereby obtained were (meth)acrylamide base polymer (Polymers B to E) aqueous solutions.

The polymerization results thereof are described in Table 1.

Polymer Production Example 6

A four neck flask equipped with a stirrer, a reflux condenser, a thermometer and a nitrogen gas-inlet tube was charged with 30.00 g of N,N-dimethylacrylamide (DMA), 0.15 g of sodium hypophosphite monohydrate and 266.85 g of distilled water, and they were mixed and dissolved, followed by adjusting the PH to 4.5. The solution was controlled to a temperature of 80° C. while allowing nitrogen gas to flow from the upper part of the solution level at a fixed flow rate, and then 3.0 g of an aqueous solution dissolving 0.30 g of ammonium persulfate was added thereto to carry out polymerization reaction for 3 hours. The solution was cooled down to 30° C. or lower to terminate the reaction to obtain a (meth)acrylamide base polymer (Polymer F) aqueous solution (non-volatile matter content: 10.58%) having a Brookfield viscosity of 37.5 mPa·s at 25° C.

The weight average molecular weight was 232,200.

Polymer Production Examples 7 to 20

DMA, copolymerizable monomers, the polymerization initiator and the chain transfer agent were used in the amounts described in Table 1 to carry out the reaction in the same manner as in Polymer Production Example 6, whereby obtained were (meth)acrylamide base polymer (Polymers G to P: those having the same composition were distinguished by suffixes of ① and the like).

The polymerization results thereof are described in Table 1.

Polymer Production Example 21

A four neck flask equipped with a stirrer, a reflux condenser, a thermometer and a nitrogen gas-inlet tube was charged with 22.12 g of N-vinyl-2-pyrrolidone (NVP), 2.88 g of itaconic acid, 0.13 g of sodium hypophosphite monohydrate and 218.84 g of distilled water, and they were mixed and dissolved, followed by adjusting the PH to 4.5. The solution was controlled to a temperature of 80° C. while allowing nitrogen gas to flow from the upper part of the solution level at a fixed flow rate, and then 2.5 g of an aqueous solution dissolving 0.25 g of 4,4'-azobis(2-cyanovaleric acid) (V-501: manufactured by Wako Pure Chemicals Industries, Ltd.) was added thereto to carry out polymerization reaction for 3 hours. The solution was cooled down to 30° C. or lower to terminate the reaction to obtain a vinylpyrrolidone base polymer (Polymer R) aqueous solution (non-volatile matter content: 11.28%) having a Brookfield viscosity of 54.5 mPa·s at 25° C.

The weight average molecular weight was 251,000.

Polymer Production Examples 22 to 24

NVP, copolymerizable monomers, the polymerization initiator and the chain transfer agent were used in the amounts described in Table 2 to carry out the reaction in the same manner as in Polymer Production Example 21, whereby obtained were vinylpyrrolidone base polymer (Polymers S to U).

The polymerization results thereof are described in Table 2.

Polymer Production Comparative Example 1

A four neck flask equipped with a stirrer, a reflux condenser, a thermometer and a nitrogen gas-inlet tube was charged with 30.00 g of N-vinyl-2-pyrrolidone (NVP) and 268.50 g of distilled water, and they were mixed and dissolved, followed by adjusting the PH to 4.5. The solution was controlled to a temperature of 80° C. while allowing nitrogen gas to flow from the upper part of the solution level at a fixed flow rate, and then 1.5 g of an aqueous solution dissolving 0.15 g of 2,2'-azobis(2-amidinopropane) dihydrochloride (V-50: manufactured by Wako Pure Chemicals Industries, Ltd.) was added thereto to carry out polymerization reaction for 3 hours. The solution was cooled down to 30° C. or lower to terminate the reaction to obtain a vinylpyrrolidone base polymer (Polymer V) aqueous solution (non-volatile matter content: 10.57%) having a Brookfield viscosity of 36.0 mPa·s at 25° C.

The weight average molecular weight was 149,800.

Polymer Production Comparative Examples 2 to 4

NVP, copolymerizable monomers, the polymerization initiator and the chain transfer agent were used in the amounts described in Table 2 to carry out the reaction in the same manner as in Polymer Production Comparative Example 1, whereby obtained were vinylpyrrolidone base polymer (Polymers W to Y) aqueous solutions.

The polymerization results thereof are described in Table 2.

Compounding Examples

Compounding of the polymers and calcium phosphate is shown in the following compounding examples.

Represented by I was a method for feeding a mixed solution of a polymer and phosphoric acid to a calcium hydroxide suspension, and represented by II was a method for feeding phosphoric acid to a mixed suspension of calcium hydroxide and a polymer to show them in Tables 3 to 5.

Stability of the resulting organic polymer/calcium phosphate fine particle-dispersed solutions was evaluated by a method of observing visually the dispersion state after standing for one day after produced (standing dispersibility) and a method of observing visually the dispersion state after carrying out centrifugal treatment at 2,000 rpm for 10 minutes (centrifugal dispersibility) according to five grades of 1 to 5 respectively:

1: no separation
2: no separation, and trace amount of precipitates observed in early stage
3: separated supernatant<10%
4: separated supernatant 10 to 25%
5: separated supernatant>25%

In the grade 2, a very small amount of the precipitates is observed after left standing for one night after produced, and filtering treatment thereof carried out if necessary provides the dispersed aqueous solutions of the present invention. The grades 1 and 2 are ranges included in the stable dispersed aqueous solution of the present invention.

Compounding (1) with (Meth)acrylamide Base Polymers

Compounding Example 1

A round bottom separable flask equipped with a stirrer and a thermometer was charged with 4.61 g of calcium hydroxide and 145.39 g of distilled water, and they were vigorously stirred to prepare a suspension. The suspension was controlled to a temperature of 40° C., and an aqueous solution prepared by mixing and dissolving 33.01 g of a 11.1% phosphoric acid aqueous solution, 56.21 g of the water-soluble polymer (Polymer A) aqueous solution adjusted to a pH of 10.0 obtained in Polymer Production Example 1 and 10.78 g of distilled water was continuously added thereto in 2 hours by means of a microtube pump while stirring at a stirring rate of 200 rpm (reaction method I). After addition, the reaction was further carried out at 40° C. for one hour to obtain a (meth)acrylamide base polymer/calcium phosphate fine particle (50:50)-dispersed aqueous solution (a-1) which does not cause separation even after standing for one day and which is excellent in stability.

The resulting dispersed aqueous solution had a pH of 8.75, and production of precipitates was scarcely observed. It did not cause a change such as separation and settling and was stable even after standing at room temperature for several weeks. Further, the resulting fine particle-dispersed aqueous solution was subjected to centrifugal treatment at 2,000 rpm for 10 minutes to find that a change such as separation and settling was not observed.

Compounding Examples 2 to 33

Various (meth)acrylamide base polymers B to P described in Table 3 were used to carry out the reaction under the conditions shown in Table 3 in the same manner as in Compounding Example 1 to obtain fine particle-dispersed aqueous solutions b-1 to p-1.

Shown in table 3 are the compounding ratios, the charge amounts, the reaction conditions, the reaction methods and the reaction results.

In the methods I and II, the polymer aqueous solutions were controlled in advance to a pH of 10.0 and then mixed with phosphoric acid or calcium hydroxide. The feeding amount thereof was set the amount of 40% of the total reaction solution as a standard.

In the compounding examples, a reaction concentration (solid content) of 5% and a reaction temperature of 40° C. were set as standards, but it was shown that compounding could be carried out as well without causing any problems in the examples (Compounding Examples 10 and 11) in which the reaction concentration was elevated to 10% and the examples (Compounding Examples 13 to 16) in which the reaction temperature was set at 20 to 80° C.

Polymers A, C, D, E and F were polymers obtained from the copolymerizable monomers containing no carboxyl groups, but an amide bond of acrylamide or N,N-dimethylacrylamide, which was the main component for the polymer was subjected to hydrolysis reaction by alkali (calcium hydroxide)in the compounding reaction step to produce a carboxyl group (ammonia and dimethylamine which were produced by the hydrolysis reaction were detected), and as a result, compounding was improved.

Compounding (2) with (Meth)acrylamide Base Polymers

Compounding Examples 34 to 38

Carboxyl group-containing polyacrylamide (Hopelon 3150B, manufactured by Mitsui Chemicals, Inc.) was used to carry out the reaction under the conditions shown in Table 4 in the same manner as in Compounding Example 1 to obtain fine particle-dispersed aqueous solutions q-1 to q-5.

Shown in table 4 are the compounding ratios, the charge amounts, the reaction conditions, the reaction methods and the reaction results.

Compounding with Vinylpyrrolidone Base Polymers

Compounding Examples 39 to 42

The vinylpyrrolidone base polymers R to U described in Table 2 were used to carry out the reaction under the conditions shown in Table 4 in the same manner as in Compounding Example 1 to obtain fine particle-dispersed aqueous solutions r-1 to u-1.

Shown in table 4 are the compounding ratios, the charge amounts, the reaction conditions, the reaction methods and the reaction results.

Compounding Comparative Examples 1 to 5

No polymer (a blank; Comparative Example 1) and the water-soluble polymers V to Y described in Table 2 were used to carry out the reactions under the conditions shown in Table 4 in the same manner as in Compounding Example 1, but settling and separation were caused in all cases immediately after stopping stirring and standing.

Shown in table 4 are the compounding ratios, the charge amounts, the reaction conditions, the reaction methods and the reaction results.

As apparent from comparison of Compounding Examples 39 to 42 with Compounding Comparative Examples 1 to 5, it can be found that in the case of the vinylpyrrolidone base polymers, the copolymer component containing a carboxyl group is necessary in order to prepare a stable compounded dispersed solution. N-vinyl-2-pyrrolidone which is a principal component for the polymer is not susceptible to hydrolysis reaction with an alkali under the compounding conditions in the present invention and does not produce as well a carboxyl group in the compounding reaction step. In such sense, it is different from the amide base polymers described above, and therefore use of the copolymers containing no carboxyl group does not provide a stable dispersed solution as shown in the coparative examples.

Compounding Examples with Carboxyl Group-modified PVA

Compounding Example 43

A round bottom separable flask equipped with a stirrer and a thermometer was charged with 127.01 g of a carboxyl group-modified polyvinyl alcohol (PVA KM-118; saponification degree: 97.4 mole %, polymerization degree: 1,800, manufactured by Kuraray Co., Ltd.) aqueous solution (9.35%) prepared by dissolving PVA in advance in distilled water and 20.91 g of distilled water, and 1.62 g of 10% sodium hydroxide aqueous solution was added thereto. Then, 0.461 g of calcium hydroxide was added while stirring to prepare a suspension. The suspension was controlled to a temperature of 40° C., and an aqueous solution prepared by mixing and dissolving 3.50 g of a 10.5% phosphoric acid aqueous solution and 96.50 g of distilled water was continuously added thereto in 2 hours by means of a microtube pump while stirring at a stirring rate of 200 rpm. After addition, the reaction was further carried out at 40° C. for 2 hours to obtain a carboxyl group-modified polyvinyl alcohol/calcium phosphate fine particle (95:5)-dispersed aqueous solution (z-1). The resulting dispersed aqueous solution had a pH of 6.55, and production of precipitates was scarcely observed. It did not cause a change such as separation and settling and was stable even after standing for several weeks. Further, the resulting fine particle-dispersed aqueous solution was subjected to centrifugal treatment at 2,000 rpm for 10 minutes to find that a change such as separation and settling was not observed. The reaction solution had a solid content of 5.2%.

Compounding Examples 44 to 66

Carboxyl group-modified polyvinyl alcohols (Z1 to Z13) were used to carry out reactions under the conditions shown in Table 5 in the same manner as in Compounding Example 43.

Shown in table 5 are the compounding ratios, the charge amounts, the reaction conditions, the reaction methods and the reaction results.

The carboxyl group-modified polyvinyl alcohols used for compounding are Z1: KM-118 (saponification degree: 97.4 mole %), Z2: KM-618 (saponification degree: 93.7 mole %), Z3: KL-118 (saponification degree: 97.4 mole %) (Z3' was subjected in advance to hydrolysis treatment with NaOH in an amount equivalent to non-saponified groups), Z4: KL-5112 (saponification degree: 95.1 mole %) and Z5: SK-5102 (saponification degree: 97.6 mole %) (all described above are manufactured by Kuraray Co., Ltd.), Z6: UFA170 (saponification degree: >96.5 mole %), Z7: UFA170M (saponification degree: 92 to 95 mole %) and Z8: UPA170 (saponification degree: 88 to 92 mole %) (all described above are manufactured by Unitika, Ltd.), and Z9: T-330H (saponification degree: >99.0 mole %), Z10: T-330 (saponification degree: 95.0 to 98.0 mole %), Z11: T-350 (saponification degree: 93.0 to 95.0 mole %), Z12: T-230 (saponification degree: 95.0 to 98.0 mole %) and Z13: T-215 (saponification degree: 95.0 to 98.0 mole %) (all described above are manufactured by The Nippon Synthetic Chemical Industry Co., Ltd.).

Compounding Comparative Example 6

A round bottom separable flask equipped with a stirrer and a thermometer was charged with 62.50 g of a high purity polyvinyl alcohol (PVA 103C; saponification degree: 98.6 mole %, polymerization degree: 300, manufactured by Kuraray Co., Ltd.) aqueous solution (10.0%) prepared by dissolving PVA in advance in distilled water and 82.89 g of distilled water, and 0.05 g of 10% sodium hydroxide aqueous solution was added thereto. Then, 4.61 g of calcium hydroxide was added while stirring to prepare a suspension. The suspension was controlled to a temperature of 40° C., and an aqueous solution prepared by mixing and dissolving 34.97 g of a 10.5% phosphoric acid aqueous solution and 65.03 g of distilled water was continuously added thereto in 2 hours by means of a microtube pump while stirring at a stirring rate of 200 rpm. After addition, the reaction was further carried out at 40° C. for 2 hours to obtain a polyvinyl alcohol/calcium phosphate fine particle (50 50)-dispersed aqueous solution (Z14-1).

The resulting dispersed aqueous solution had a pH of 7.61, and after standing for a night, about 20% of the reaction solution was turned into a transparent supernatant and separated (standing dispersibility 4). The reaction solution had a solid content of 5.0%.

Compounding Comparative Examples 7 to 11

Various polyvinyl alcohols Z14 to Z16 were used to carry out the reaction under the conditions shown in Table 5 in the same manner as in Compounding Comparative Example 6 to find that standing without stirring caused settling and separation in all cases.

Shown in table 5 are the compounding ratios, the charge amounts, the reaction conditions, the reaction methods and the reaction results.

The polyvinyl alcohols used for compounding are Z14: 103C (high purity polyvinyl alcohol, saponification degree: 98.6 mole %), Z15: 205C (high purity polyvinyl alcohol, saponification degree: 88.1 mole %), Z16: CM-318 (cationic polyvinyl alcohol, saponification degree: 96.4 mole %) and Z17: 205S (partially saponified type polyvinyl alcohol, saponification degree: 88.0 mole %) (Z14' and Z16' were subjected in advance to hydrolysis treatment with NaOH in an amount equivalent to non-saponified groups) (all described above are manufactured by Kuraray Co., Ltd.).

As apparent from Compounding Comparative Examples 6 to 11, the stable fine particle-dispersed aqueous solutions are not prepared from PVA having no carboxyl group in a molecule. In Compounding Comparative Examples 7 and 10, complete saponification treatment has been carried out to remove an influence caused by the non-saponified part, but compounding is inferior. Thus, an effect exerted to compounding by a carboxyl group is apparent.

Stability of Compounded Dispersed Aqueous Solution (1) pH Effect

Distilled water was added to the dispersed aqueous solution (h-3) obtained in Compounding Example 10 to adjust a concentration to 0.5 wt %. A 11.1 wt % phosphoric acid aqueous solution was added little by little to about 30 ml of this dispersed solution by means of a microsyringe to control the pH to 6.51, 5.93, 5.52 and 5.01. No change was observed immediately after addition in any case, but the one controlled to a pH of 5.01 was completely separated into two layers after left standing a night. A visual change was not observed in the other cases.

Further, continuous addition of 11.1 wt % phosphoric acid to the 0.5 wt % diluted solution allowed phosphoric acid to be consumed in the vicinity of pH 4.5 and allowed the cloudy dispersed aqueous solution to turn completely transparent. A pH area in which two-phase separation is caused is a pKa area of a carboxyl group of a polymer, and it is considered that a partial or overall loss in an ionicity of a carboxylic acid anion with a reduction in the pH exerts an influence on stability of the compounded dispersed solution. Further reduction in the pH allows the composite to disappear as hydroxyapatite is dissolved, so that the cloudy dispersed aqueous solution turns transparent.

(2) Inorganic Salt Addition Effect

The dispersed aqueous solution obtained in Compounding Example 10 was controlled to a concentration of 0.5 wt % in the same manner as the case of the above (1). In this case, NaCl or $Na_2SO_4$ was added so that the salt concentration became 0.05 to 2.0 mol/l, and stability of the dispersed solution was evaluated.

A change caused by adding NaCl was not observed in this concentration range, but the $Na_2SO_4$-added system was completely separated into two layers in a concentration of 0.25 ml/l or more, and no change was observed in a concentration of 0.05 ml/l even after one month passed.

The effects of pH and salt addition described above show that an ionic action plays an important role in the dispersion stability, and it is strongly indicated that such action is exerted by the carboxylic acid anion.

Electron Microscope Observation/dispersed Solution

Poly(meth)acrylamide (PAM) Base Composite

The (meth)acrylamide base polymer/calcium phosphate fine particle-dispersed aqueous solution (h-2) obtained in Compounding Example 9 was diluted, dried on collodion film-clad copper mesh and photographed to obtain a transmission electron microscopic photograph, which was shown in FIG. 1(a).

Figure 2:
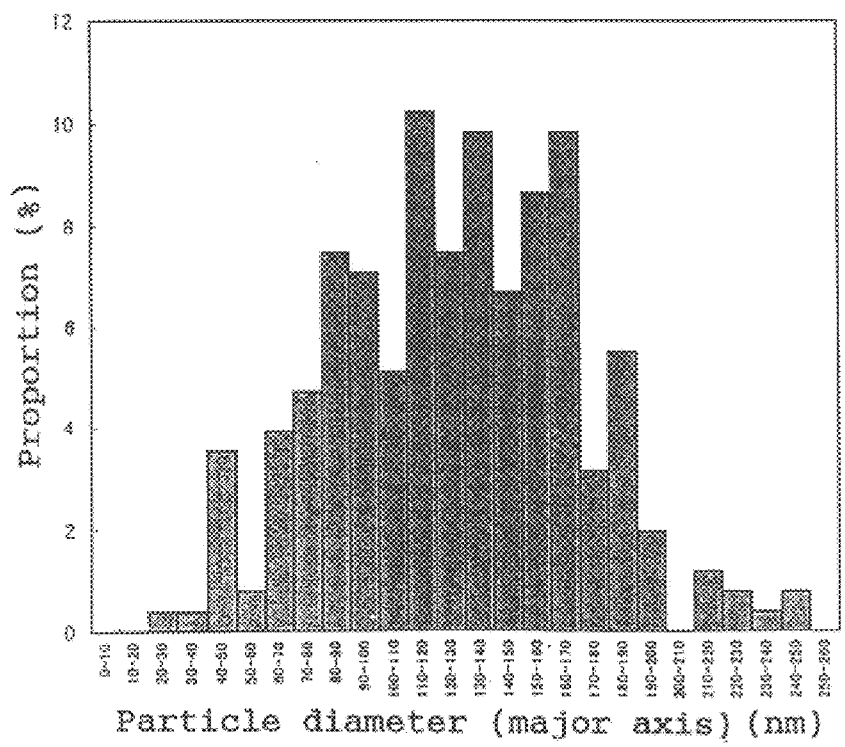
FIG. 2 is a particle diameter distribution diagram in the major axis direction determined from FIG. 1(*a*).

As apparent from FIG. 1(a), the calcium phosphate fine particles are long and slender, elliptical particles, and these primary particles are dispersed homogeneously on the collodion film without coagulating. Particle diameter distribution in the major axis direction which was determined from FIG. 1 was shown in FIG. 2.

Carboxyl Group-modified PVA Base Composite

The carboxyl group-modified polyvinyl alcohol/calcium phosphate fine particle-dispersed aqueous solution (z1-8) obtained in Compounding Example 50 was diluted, dried on collodion film-clad copper mesh and photographed to obtain a transmission electron microscopic photograph, which was shown in FIG. 1(b).

Also in FIG. 1(b), the calcium phosphate fine particles are long and slender, elliptical particles as is almost the case with FIG. 1(a), and these primary particles are dispersed homogeneously on the collodion film without coagulating.

Blank

The calcium phosphate-dispersed aqueous solution (blank) obtained in Compounding Comparative Example 1 caused setting and separation and therefore was sampled after well stirred. Then, it was diluted, dried on collodion film-clad copper mesh and photographed to obtain a transmission electron microscopic photograph, which was shown in FIG. 1(c).

Observing FIG. 1(c), it can be found that a structure in which a lot of long and slender, acicular crystals are coagulated is formed and notably different from those of (a) and (b) which are the stable dispersed aqueous solutions.

Film Preparation

Film Preparation Example 1

The stable dispersed aqueous solutions (a-1 to z13-1) obtained in Compounding Examples 1 to 66 were put in polymethylpentene resin-made Petri dishes having a diameter of 90 mm and placed on a horizontal table, and dried nitrogen was allowed to flow over them, whereby carboxyl group-containing polymer/calcium phosphate composite films having excellent transparency were produced. All samples were turned into transparent films. Further, a change in transparency was not observed as well in the films which were subjected to drying treatment at 110° C. for 2 hours by means of an air-blasting dryer.

The films having various thicknesses were prepared by controlling a solution amount put in the Petri dish. In particular, the films prepared from the PVA base compounded dispersed aqueous solutions (z1-1 to z13-1) obtained in Compounding Examples 43 to 66 were tough and soft films and endowed with cutting processability with scissors. Further, 10%, 20% and 30% of glycerin based on the solid content weight were added as a plasticizer to these dispersed solutions, whereby even the films prepared from the composites containing 50% calcium phosphate were turned into films which were highly flexible and were not cracked by bending even if they were completely dried.

The dispersed aqueous solutions (v-1 to y-1 and z14-1 to z16-2) obtained in Compounding Comparative Examples 2 to 10 caused settling and separation, so that after well stirred, they were put in polymethylpentene resin-made Petri dishes having a diameter of 90 mm and placed on a horizontal table, and dried nitrogen was allowed to flow over them, whereby it was tried to produce polyvinyl alcohol containing no carboxyl groups/calcium phosphate-composite films. However, they were completely separated into transparent polymer films and white solids, and the homogeneous composite films were not obtained.

Film Preparation Example 2

The stable dispersed aqueous solutions (a-1 to z13-1) obtained in Compounding Examples 1 to 66 which were subjected, if necessary, to filtering treatment with a filter cloth or a metal mesh were applied on polyethylene terephthalate (PET) films by means of a bar coater, and the films were fixed and air-dried, whereby prepared were films having the carboxyl group-containing polymer/calcium phosphate composite having excellent transparency on a surface layer.

Film Preparation Example 3

The stable dispersed aqueous solutions (a-1 to z13-1) obtained in Compounding Examples 1 to 66 which were subjected, if necessary, to filtering treatment with a filter cloth or a metal mesh were allowed to be flow-coated on glass. They were put on a horizontal table, and dried nitrogen was allowed to flow over them, whereby prepared were glass plates having the carboxyl group-containing polymer/calcium phosphate composite films having excellent transparency on a surface layer.

Film Tensile Strength Measurement
Carboxyl Group-modified PVA Base Composite

The film having an average film thickness of 64 $\mu$m obtained in Film Preparation Example 1 from the dispersed aqueous solution (z1-9) (polymer:calcium phosphate=50:50 composite) obtained in Compounding Example 51 and a film having an average film thickness of 75 $\mu$m produced from the raw material PVA (Z1: KM-118) aqueous solution used for compounding by the same method were used to prepare samples, and the respective samples which were subjected to humidity conditioning under the conditions of 23±2° C. and 50±5% RH were subjected to a tensile test at a speed of 50.0 mm/min with test pieces of a JIS K7113 No. 2 (1/2) form.

The PVA alone base film had a tensile strength (rupture) of 65.3 MPa, but the composite film had a tensile strength of 116.8 MPa and was observed to be improved in a strength by about 80%.

Ultramicrohardness Measurement
Carboxyl Group-modified PVA Base Composite

The film obtained in Film Preparation Example 1 from the dispersed aqueous solution (z1-9) (polymer:calcium phosphate=50:50 composite) obtained in Compounding Example 51 and a film produced from the raw material PVA (Z1: KM-118) alone used for compounding were used for measurement by means of a Shimadzu dynamic ultramicrohardness tester DUH-201 type (manufactured by Shimadzu Corporation). The respective films had the same film thickness as those of the films which were used for the tensile test, and the samples which were subjected to humidity conditioning under the conditions of 23±2° C. and 50±5% RH were tested under the conditions of a test load of 9.8 mN, a holding time of 5 seconds, a loading speed of 1.428 mN/sec and a displacement full scale of 10 $\mu$m based on a No-2 mode.

Indentation depths (D1 and D2 ($\mu$m)) observed in applying a load of 9.8 mN for a holding time of 5 seconds and after removing the load were measured at ten spots in the film to calculate average values, and they were 1.42 and 1.04 in the PVA alone base films and 1.06 and 0.77 in the composite base films, respectively. The dynamic hardnesses (DHT115-1, DHT115-2) calculated from these values were 19.0 and 35.4 in the PVA alone base films and 33.8 and 8.65 in the composite base films, respectively, and it was confirmed that the surface hardness grew large by compounding.

The dynamic hardness is calculated from the following calculation equation:

$$\text{dynamic hardness} = \{9.8 \text{ (mN)}/D2\} \times \alpha$$

wherein $\alpha$ is 3.8584 when a triangular pyramid indentator (115°) is used.

Gas Permeability

The film obtained in Film Preparation Example 1 from the dispersed aqueous solution (z1-9) (polymer:calcium phosphate=50:50 composite) obtained in Compounding Example 51 and a film produced from the raw material PVA (Z1: KM-118) alone used for compounding were used to measure a permeability of helium gas through the film. The permeability was determined by means of a gas permeability-measuring apparatus for a film disclosed in Japanese Parent Application Laid-Open No. Hei 6-241978 in which a quadrupole mass spectrometer was used for a detector. The PVA alone film had a thickness of 82 $\mu$m and a permeation amount of helium gas of 10.7 cc/m$^2$·day (permeability coefficient: $13.3*10^{-13}$ cc*cm/cm$^2$·sec·cmHg), and the composite film had a thickness of 55 $\mu$m and a permeation amount of helium gas of 7.5 cc/m$^2$·day (permeability coefficient: 6.3*10–13 cc*cm/cm$^2$·sec·cmHg). It was confirmed that the permeability coeffieicnt was reduced by 50% or less by compounding and the gas barrier property was elevated to a large extent.

FT-IR Measurement

PVA Base Composite

Figure 3:
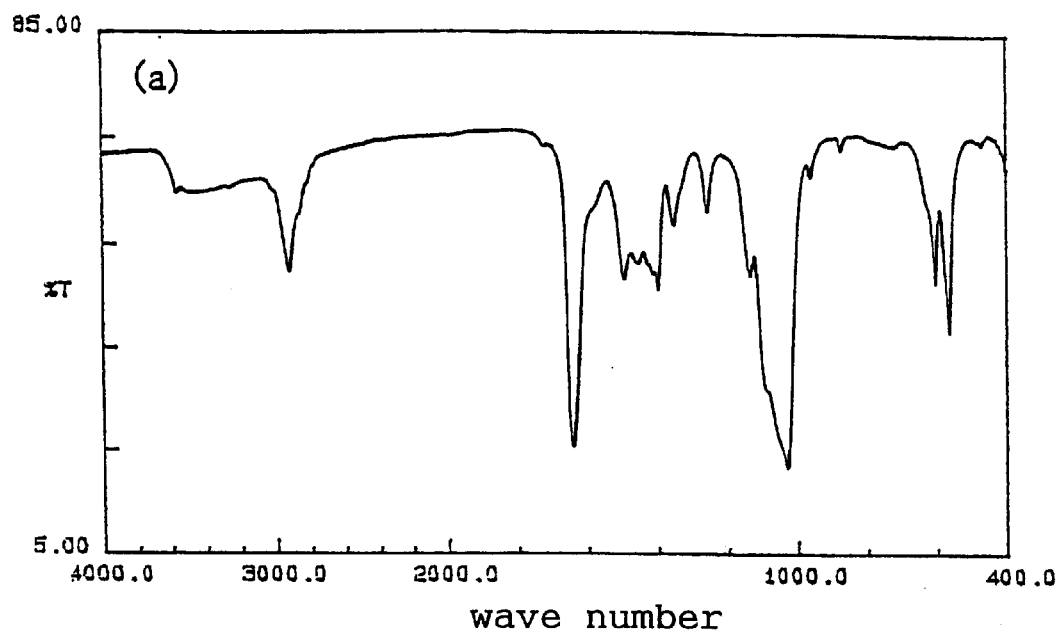
FIG. 3(*a*) is a diagram showing FT-IR spectra of a sample prepared by casting the PAM base-dispersed aqueous solution (h-5) prepared in Compounding Example 12 on an aperture plate of KRS-5 to form a thin film.
Figure 3:
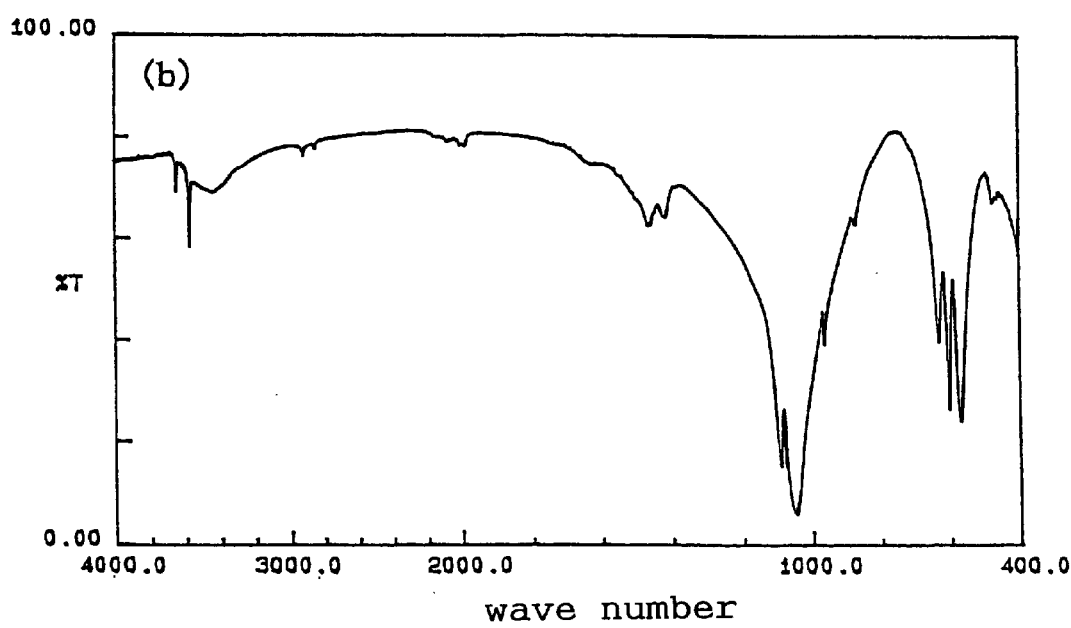

The dispersed aqueous solution (h-5) produced in Compounding Example 12 was cast on an aperture plate of KRS-5 to prepare a sample of a thin film, and FT-IR spectra of the sample are shown in FIG. 3(a).

Observed were both of a peak originating in the (meth)acrylamide base polymer and a peak originating in hydroxyapatite.

Further, this film was subjected to heat treatment at 800° C. for 3 hours in an electric furnace to find that a white solid remained and a weight thereof accounted for 50% of the film before the heat treatment. IR spectra of the white solid are shown in FIG. 3(b). It was confirmed that the polymer component was burnt and hydroxyapatite which was accelerated in crystallization remained quantitatively.

Carboxyl Group-modified PVA Base Composite

Figure 4:
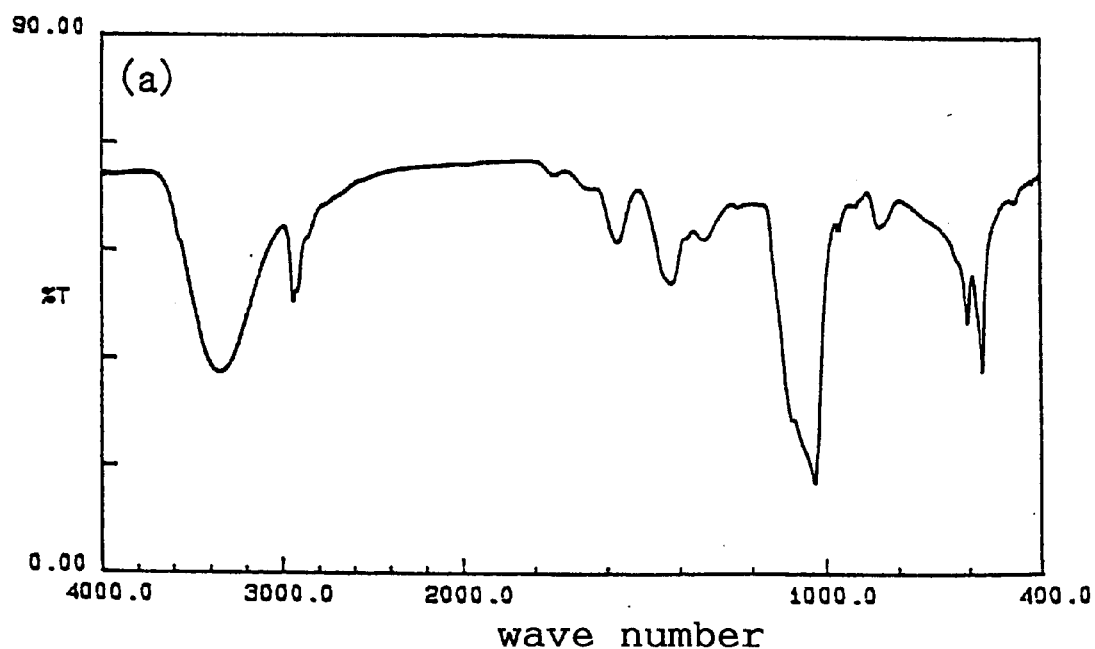
FIG. 4(*a*) is a diagram showing FT-IR spectra of a sample prepared by casting the carboxyl group-modified PVA base-dispersed aqueous solution (z1-7) prepared in Compounding Example 49 on an aperture plate of KRS-5 to form a thin film.
Figure 4:
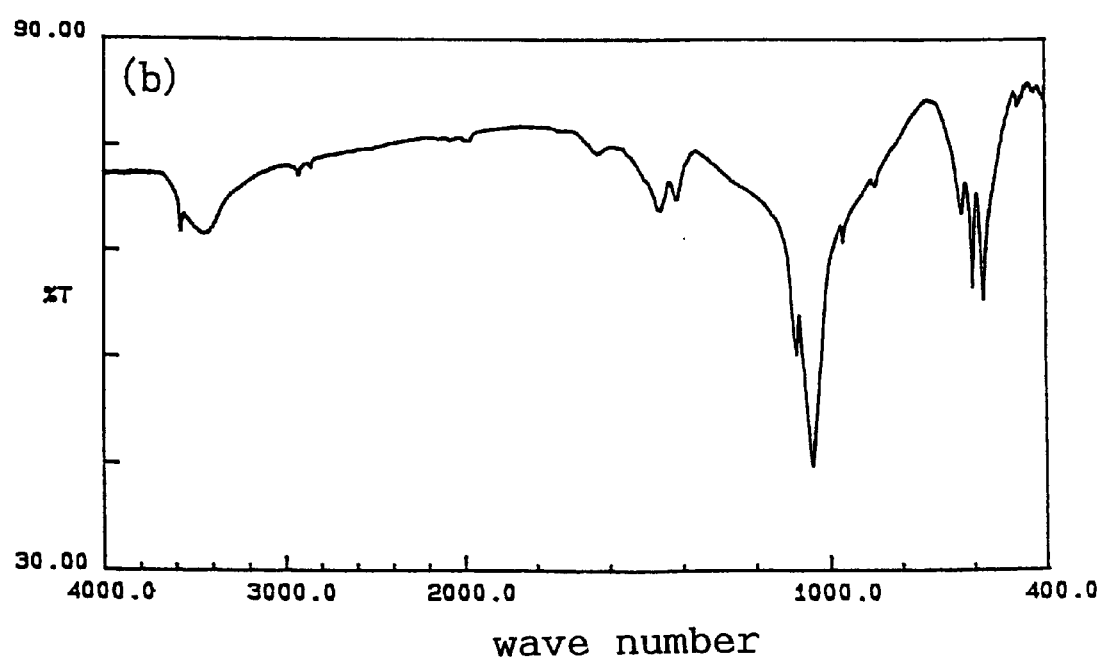

The dispersed aqueous solution (z1-7) produced in Compounding Example 49 was cast on an aperture plate of KRS-5 to prepare a sample of a thin film, and FT-IR spectra of the sample are shown in FIG. 4(a).

Observed were both of a peak originating in the carboxyl group-modified polyvinyl alcohol and a peak originating in hydroxyapatite.

Further, this film was subjected to heat treatment at 800° C. for 9 hours in an electric furnace to find that a white solid remained and a weight thereof accounted for 50% of the film before the heat treatment. IR spectra of the white solid which was measured by a KBr tablet method is shown in FIG. 4(b). It was confirmed that the polymer component was burnt and hydroxyapatite which was accelerated in crystallization remained quantitatively.

Polyvinylpyrrolidone Base Composite

Figure 5:
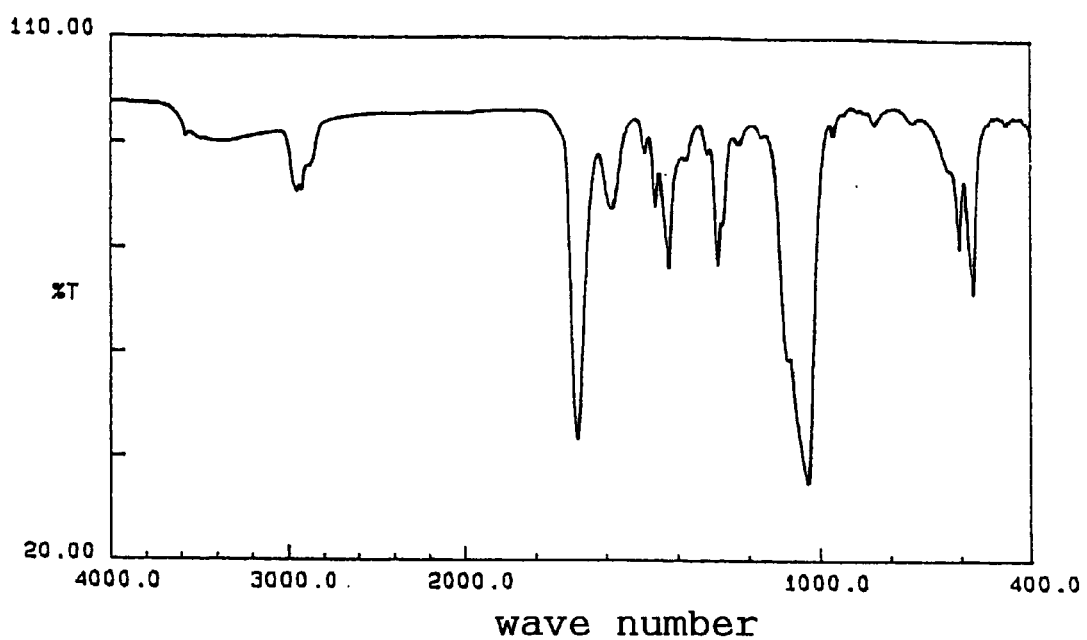
FIG. 5 is a diagram showing FT-IR spectra of a sample prepared by casting the polyvinylpyrrolidone base-dispersed aqueous solution (u-1) prepared in Compounding Example 42 on an aperture plate of KRS-5 to form a thin film.

The dispersed aqueous solution (u-1) produced in Compounding Example 42 was cast on an aperture plate of KRS-5 to prepare a sample of a thin film, and FT-IR spectra of the sample are shown in FIG. 5.

Observed were both of a peak originating in the polyvinylpyrrolidone base polymer and a peak originating in hydroxyapatite.

X-ray Diffraction Analysis (XRD)

PVA Base Composite

Shown in FIG. 6(a) is XRD spectra of a sample obtained by powdering the dispersed aqueous solution (h-5) produced in Compounding Example 12 by freeze-drying, and shown in FIG. 6(b) is XRD spectra of a sample obtained by casting the same dispersed aqueous solution on a glass substrate to prepare a film by the method shown in Film Preparation Example 3. A mark * was given to a peak corresponding to the (h, k, 0) face.

A spectral pattern of the powder was consistent with that of hydroxyapatite, but while a peak of the (h, k, 0) face was observed in the spectra of the film, the other peaks were reduced in an intensity to a large extent or disappeared. Thus, it is estimated that the hydroxyapatite particles contained in the film are oriented parallel to the glass face in a c axis.

Carboxyl Group-modified PVA base composite

Figure 7:
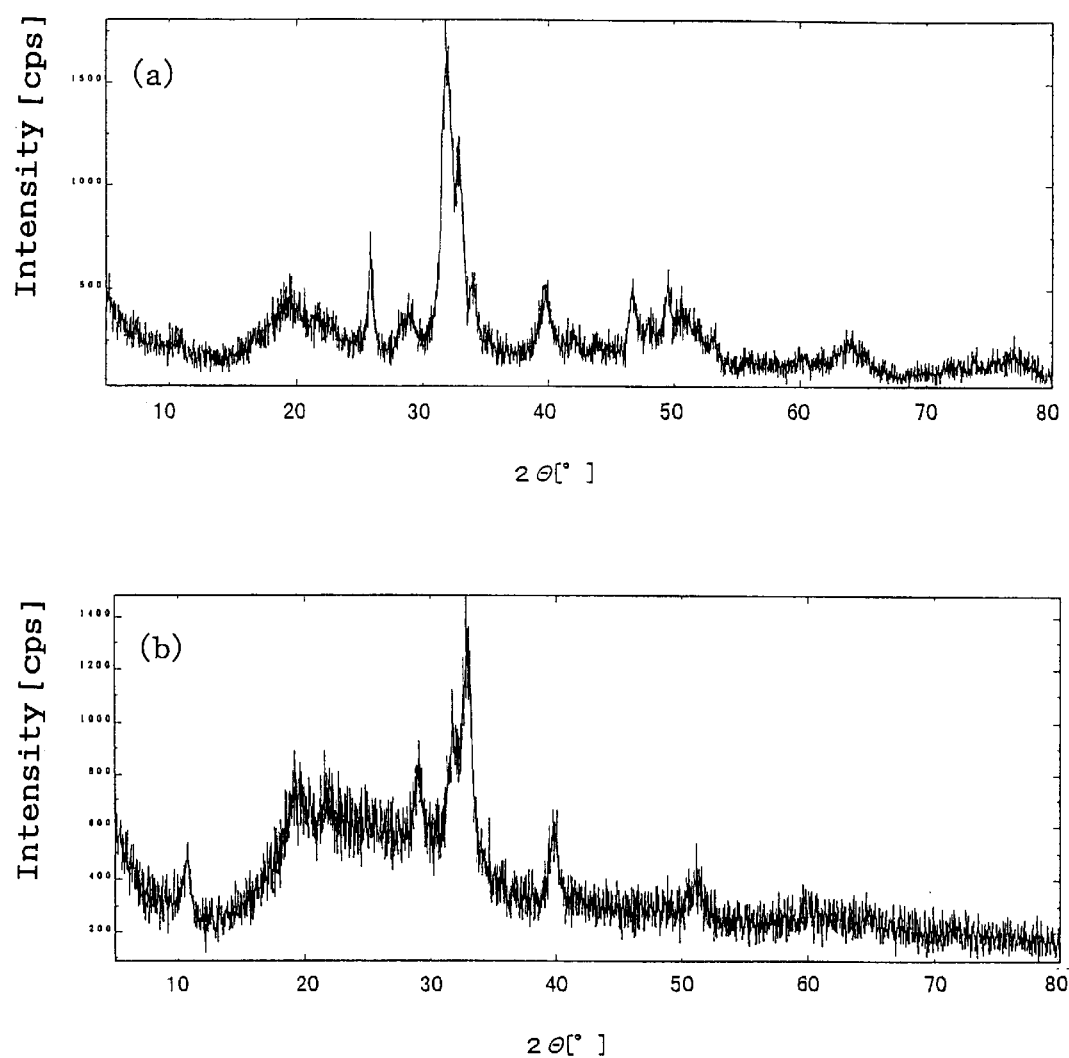
FIG. 7(*a*) is a diagram showing XRD spectra of a sample prepared by turning the carboxyl group-modified PVA base-dispersed aqueous solution (z1-7) prepared in Compounding Example 49 into powder by freeze drying.

A spectral pattern of XRD spectra of a sample obtained by powdering the dispersed aqueous solution (z1-7) produced in Compounding Example 49 by freeze-drying was almost consistent with that of hydroxyapatite (FIG. 7 (a)). A peak of a (h, k, 0) face in hydroxyapatite was observed, but the other peaks were reduced in an intensity to a large extent or disappeared. Shown in FIG. 7(a) was XRD spectra of a sample obtained by casting the same dispersed aqueous solution on a glass substrate to prepare a film. It was estimated that the hydroxyapatite particles contained in the film were oriented parallel to the glass face in a c axis as was the case with the composite with the(meth)acrylamide base polymer.

Electron Microscope Observation/film

PAM Base Composite

Figure 8:
FIG. 8 is a transmission electron microscopic photograph obtained by photographing a film prepared according to Film Preparation Example 1 from the (meth)acrylamide base polymer/calcium phosphate fine particle-dispersed aqueous solution (h-5) obtained in Compounding Example 12 from a plane direction (a) and a cross-sectional direction (b) based on a ultrathin sectioning method.
Figure 8:
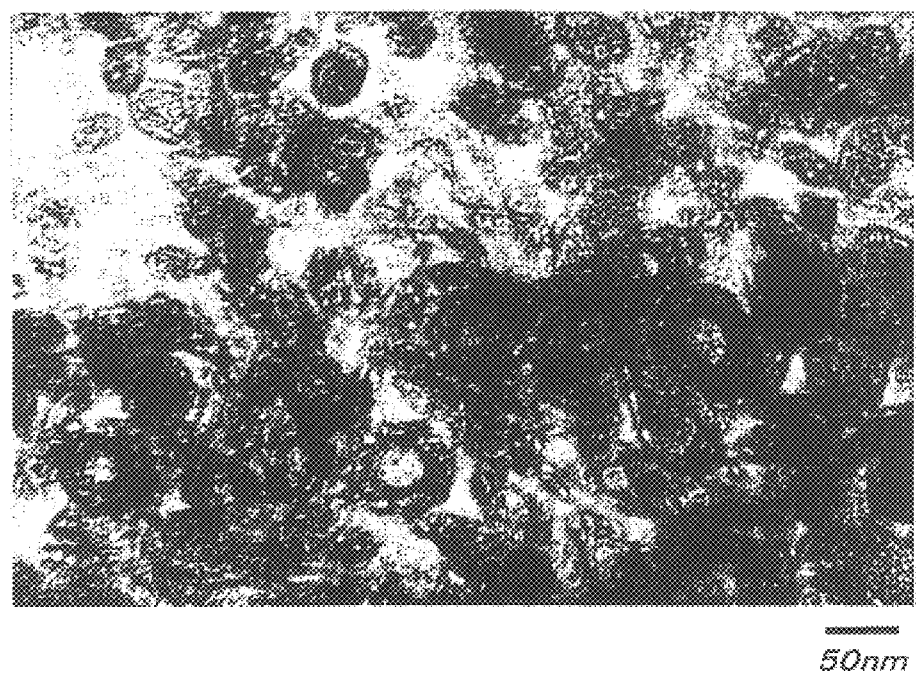

The composite film (Film Preparation Example 1) produced from the (meth)acrylamide base polymer/calcium phosphate fine particle-dispersed aqueous solution (h-5) obtained in Compounding Example 12 by a casting method was observed from a plane direction and a cross-sectional direction of the film by ultramicrotomy by means of a transmission electron microscope (TEM). The result in the plane direction is shown in FIG. 8(a), and the result in the cross-sectional direction is shown in FIG. 8(b).

Long and slender, elliptical particles having a major axis of 70 to 200 nm and a minor axis of 25 to 50 nm were observed in the plane direction (a). On the other, a large number of such images as those obtained by cutting crosswise the long and slender particle was observed in the cross-sectional direction (b), and those exhibiting a hollow structure were partially observed as well. An electron microscopic image showing that the major axis is oriented in the plane direction is well consistent with the results obtained by XRD. As a result of local elemental analysis of the particles by a UTW (ultra thin window) type EDS detector (energy dispersive spectroscopy), an element ratio of Ca/P was a value of 1.43 in terms of an average in three points. A Ca/P ratio of hydroxyapatite was 1.67, and therefore it was shown from the results of XRD, IR and TEM that the calcium phosphate particles contained in the film comprise hydroxyapatite of a calcium-defective type.

Measurement of Light Transmittance Through Film

PAM Base Composite

Wavelength dependency of a light transmittance of the composite films (the films had an average film thickness falling in a range of 230 to 270 $\mu$m) produced from the dispersed solution a-1 to u-1 having excellent stability by the method according to Film Preparation Example 1 showed a similar pattern, and any of the films had a transmittance exceeding 50% at 700 nm and exhibited high transparency. Among them, comparison of the polymer/calcium phosphate composite film with the film of the polymer alone was shown in FIG. 9.

Figure 9:
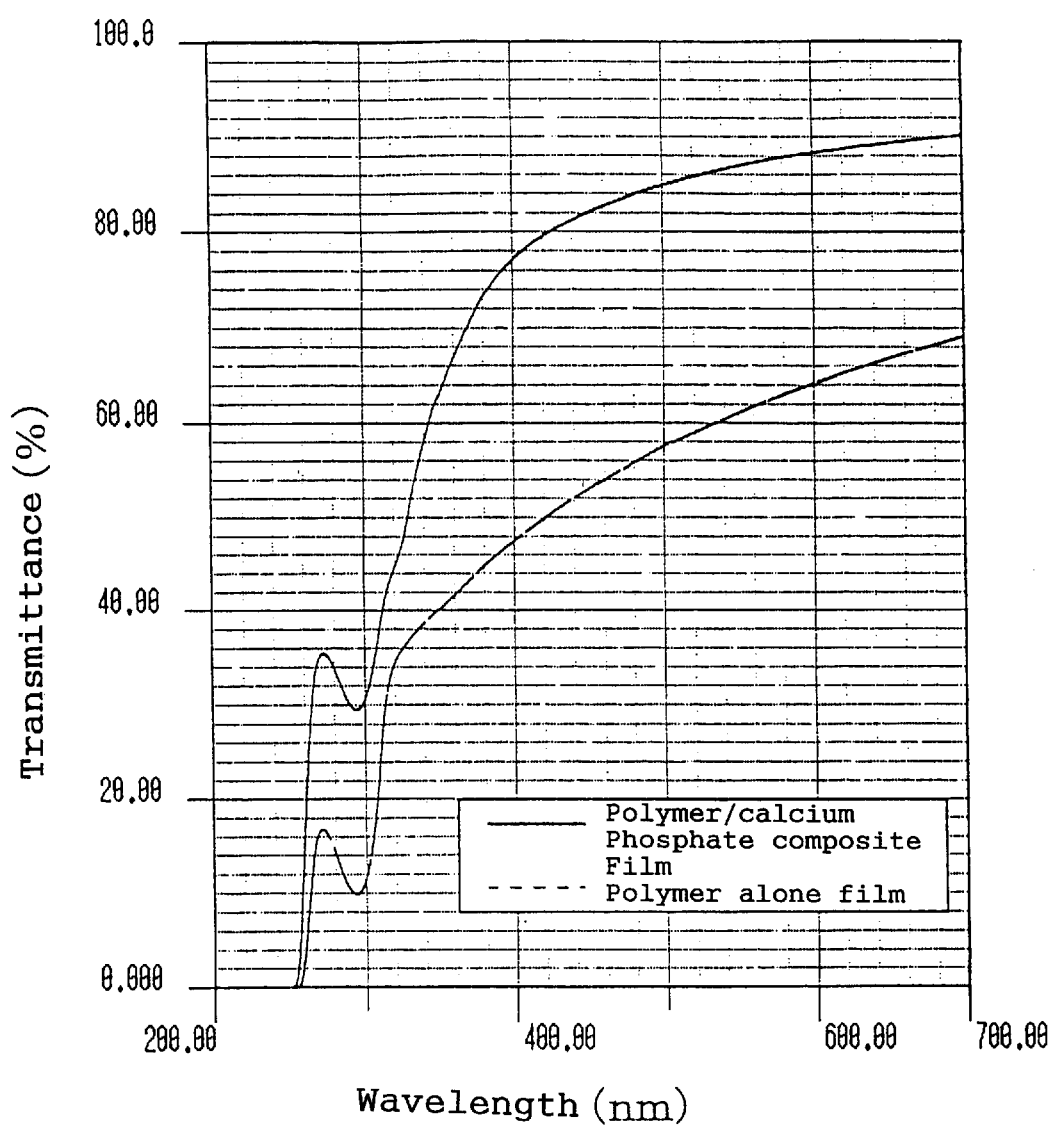
FIG. 9 is a diagram showing a wavelength dependency of light transmission factors of a film prepared according to Film Preparation Example 1 from the (meth)acrylamide base polymer/calcium phosphate fine particle-dispersed aqueous solution (h-7) obtained in Compounding Example 14 and a film of a (meth)acrylamide base polymer H② alone.

As apparent from FIG. 9, the composite film has better transparency as compared with that of the film of the polymer alone.

Figure 10:
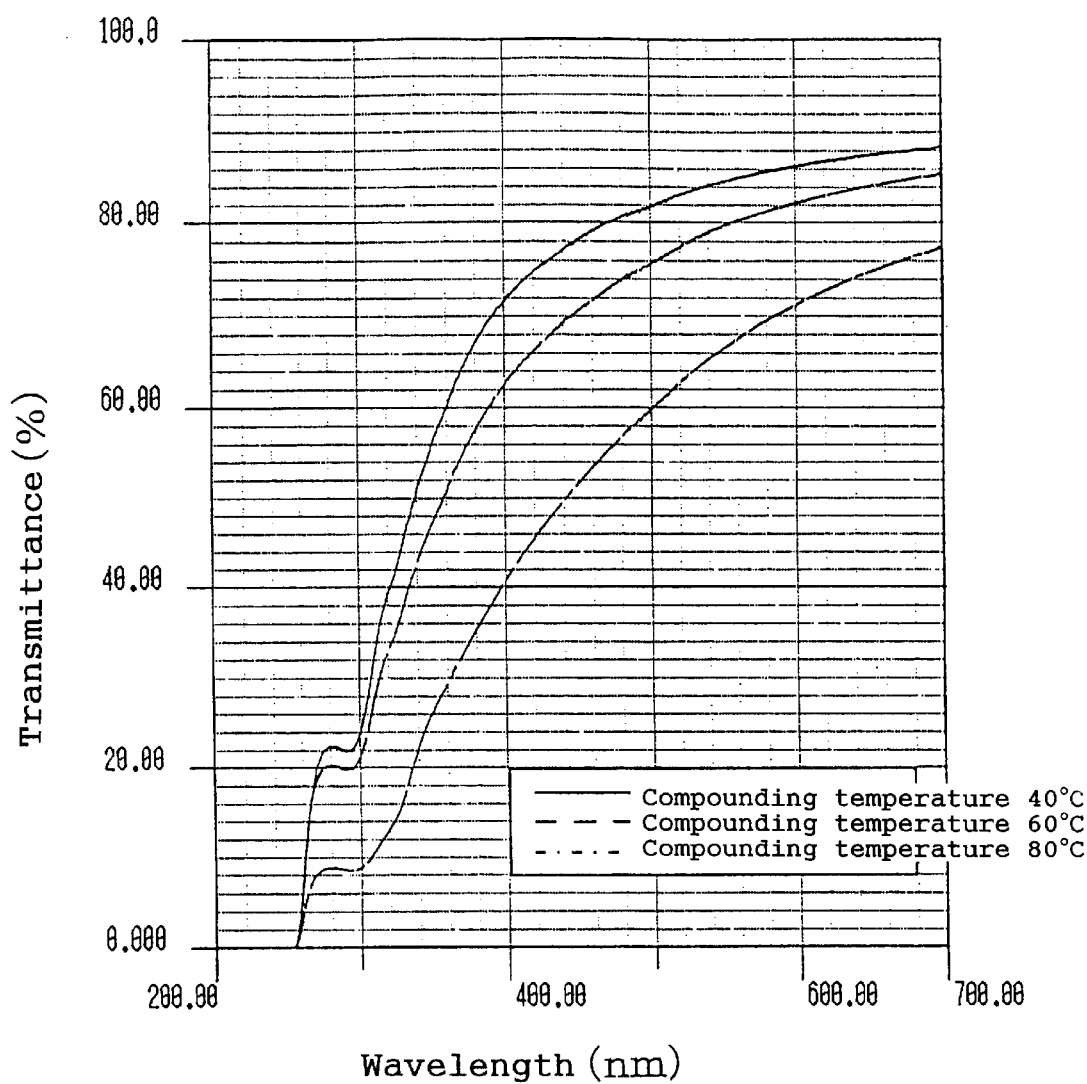
FIG. 10 is a diagram showing a wavelength dependency of light transmission factors of (meth)acrylamide base polymer/calcium phosphate-composite films prepared at different compounding temperatures [filems prepared from dispersed aqueous solution h-7 (compounding temperature: 40° C.), dispersed aqueous solution h-8 (compounding temperature: 60° C.) and dispersed aqueous solution h-9 (compounding temperature: 80° C.)].

Further, an effect exerted on the transparency by the compounding temperature was shown in FIG. 10 [the film (compounding temperature: 40° C.) prepared from the dispersed aqueous solution h-7, the film (compounding temperature: 60° C.) prepared from the dispersed aqueous solution h-8 and the film (compounding temperature: 80° C.) prepared from the dispersed aqueous solution h-9]. It was found from FIG. 10 that the transparency of the film was changed according to the compounding temperature.

Figure 11:
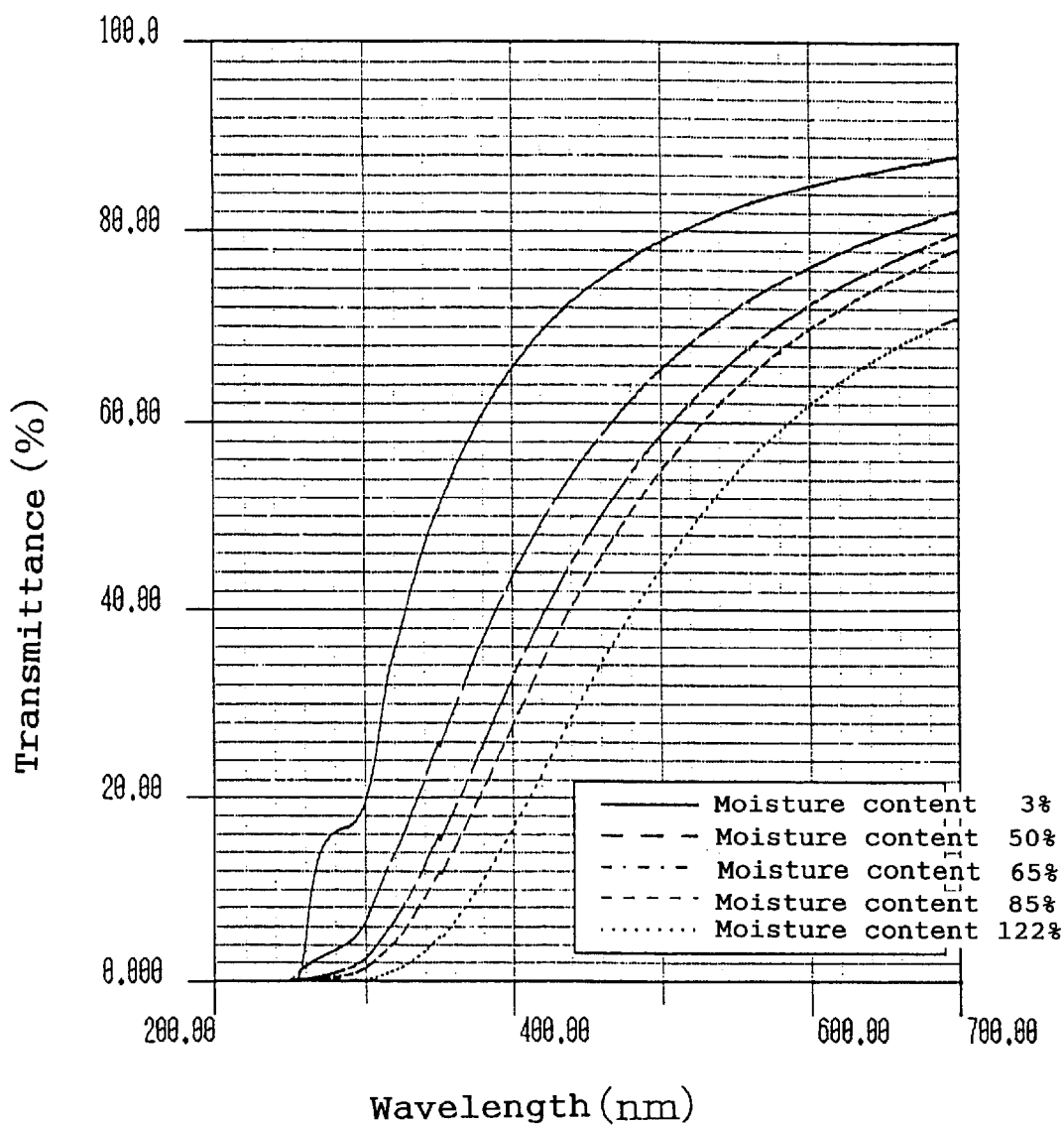
FIG. 11 is a diagram showing a wavelength dependency of light transmission factors of (meth)acrylamide base polymer/calcium phosphate-composite films having different moisture contents (prepared from the dispersed aqueous solution h-7) (measured were the films having moisture contents of 3%, 50%, 65%, 85% and 122% relative to the film weight respectively; and a moisture content of the film dried at 120° C. for 4 hours was set at 0%).
Figure 12:
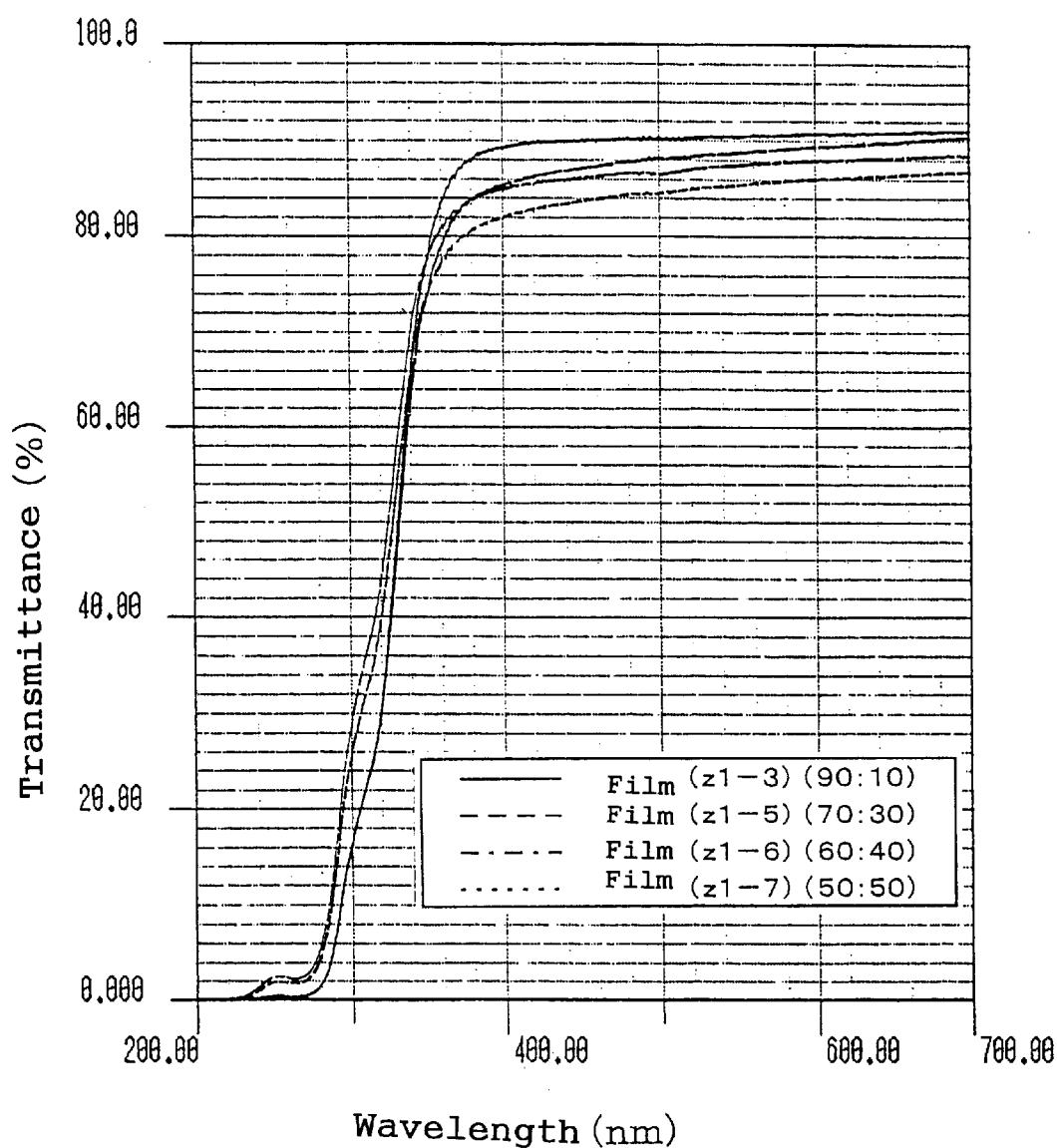
FIG. 12 is a diagram showing a wavelength dependency of light transmission factors of carboxyl group-modified PVA/calcium phosphate-composite films having different compounding rates (films obtained from the dispersed aqueous solutions z1-3, z1-5, z1-6 and z1-7).

An effect of a moisture content contained in the film was shown in FIG. 11. The composite film prepared from the dispersed aqueous solution h-7 was dipped in water and then air-dried to change the moisture content. Measured were the films having moisture contents of 3%, 50%, 65%, 85% and 122% based on the film weight. The film which was dried at 120° C. for 4 hours was set to a moisture content of 0%. It was found from FIG. 11 that the transparency was changed according to the moisture contents in the film, and this change was reversible. This phenomenon showed that the change amplitude was large particularly in the UV ray area and that they could be used for UV-shielding cosmetics.

Carboxyl Group-modified PVA Base Composite

Wavelength dependency of a light transmittance of the composite films produced from the fine particle-dispersed aqueous solutions (z1-1 to z13-1) having excellent stability by the method according to Film Preparation Example 1 showed a similar pattern, and any of the films had a transmittance exceeding 50% at 700 nm and exhibited high transparency. The films used for measurement had an average film thickness falling in a range of 90 to 150 $\mu$m. The films prepared from the dispersed aqueous solutions z1-3 (90:10 composite) and z1-5 (70:30 composite) in Film Preparation Example 1 had film thicknesses of about 120 $\mu$m and 140 $\mu$m respectively, and the films prepared from the dispersed aqueous solutions z1-6 (60:40 composite) and z1-7 (50:50 composite) in the same manner had a film thickness of about 90 $\mu$m.

Coating Test on Paper

In the following coating examples and coating comparative examples, medium grade paper (basis weight capacity: 58 g/m$^2$) was used as base paper for coating. The surface strength was measured for RI pick (in ten marks relative evaluation, the higher the marks, the higher the surface strength) by means of an RI-3 type (manufactures by Akira Mfg. Co., Ltd.), and the Z axis strength was measured by means of an internal bond tester (Kumagai Riki Kogyo Co., Ltd.).

Coating Examples 1 to 5

Base paper for coating was dipped for one second in the fine particle-dispersed aqueous solutions (q-1 to q-5) obtained in Coating Examples 34 to 38 and squeezed between two rolls, and then the amount of the solution absorbed was weighed to determine the coating amount. A concentration of the coating solution was controlled in advance so that the coating amounts were 1.0 and 1.8 g/m$^2$ in terms of the total of the non-volatile contents of the (metha)acrylamide polymer and calcium phosphate (the dispersed aqueous solution concentration: 2.0 to 3.5 wt %). A pH of the coating solution was controlled to 7.8 to 8.2. The paper was dried on a drum dryer having a surface temperature set to 110° C. for 90 seconds immediately after coating to determine a paper strength after humidity control in an air-conditioned chamber (20° C., 65% RH) for 24 hours. The results thereof are shown in Table 6.

Coating Comparative Example 1

The same operation as in Coating Examples 1 to 5 was carried out to prepare a coated paper, except that the coating solution was changed to an aqueous solution of a (meth) acrylamide base polymer (Hopelon 3150B, manufactured by Mitsui Chemicals, Inc.) alone, and the paper strength was measured. The results thereof are shown in Table 6

Figure 6:
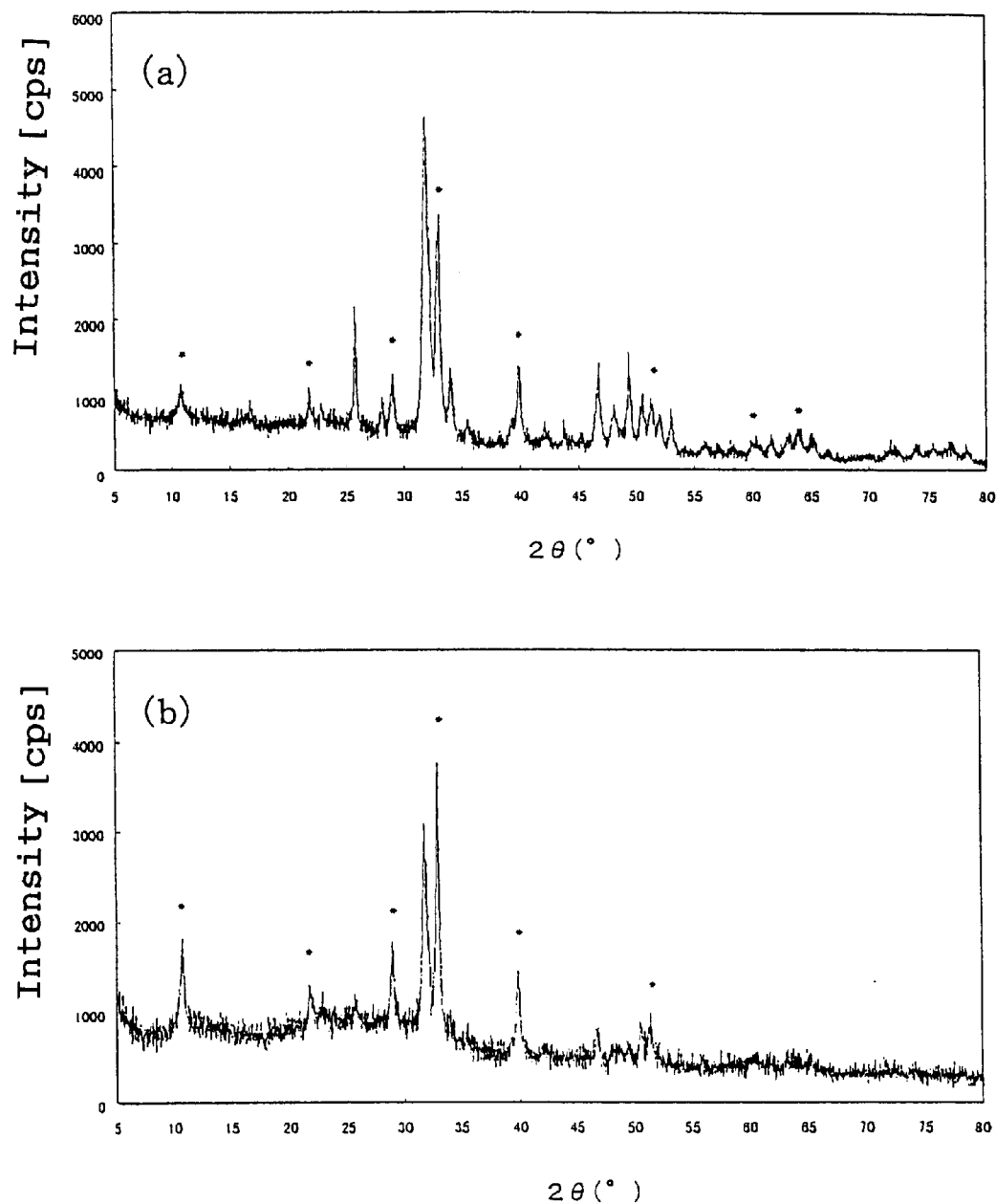
FIG. 6(*a*) is a diagram showing XRD spectra of a sample prepared by turning the PAM base-dispersed aqueous solution (h-5) prepared in Compounding Example 12 into powder by freeze drying.

It is apparent from the results shown in FIG. 6 that a paper strength-improving performance of the dispersed aqueous solutions is very excellent as compared with that of the conventional (meth)acrylamide base polymer. In particular, in the dispersed solution having a (meth)acrylamide polymer/calcium phosphate ratio of 95/5, the Z axis strength-improvement rate over the base paper for coating, which is a blank, is elevated by 20 to 35% based on that of Coating Comparative Example 1, and the very good result is given as compared with the case where the polymer alone is used. These results mean that compounding the polymer with dispersing calcium fine particles makes it possible to further raise a limit in a paper strength which can be reached by the polymer alone.

Coating Test for Ink Jet (IJ)

In the following coating examples and coating comparative examples, wood free paper (OK-Prince, basis weight: 104.7 g/m$^2$, manufactured by Oji Paper Co., Ltd.) was used as base paper for coating.

IJ Coating Example 1

The (meth)acrylamide base polymer/calcium phosphate fine particle-dispersed aqueous solution (h-4) obtained in Compounding Example 11 was adjusted to 10% and then coated on base paper for coating by means of a wire bar so that a coating amount became 5.0 g/m$^2$. After coating, it was dried at 120° C. for 90 seconds to obtain an ink jet recording sheet.

IJ Coating Comparative Example 1

Mixed in a ratio of 1:1 were a 10% dispersed solution obtained by stirring 10 parts of fine powder hydroxyapatite (HCA-3000, manufactured by Mitsui Chemicals, Inc.) and 90 parts of water at 3000 rpm for 3 minutes by means of a homogenizer (manufactured by Nihonseiki Kaisha, Ltd.) and 10% aqueous solution of polymer A, which was prepared form the polymer A aqueous solution obtained in Polymer Production Example 1, to prepare a coating solution. The resulting coating solution was coated on base paper for coating by means of a wire bar so that a coating amount became 5.0 g/m$^2$ and then dried at 120° C. for 90 seconds to obtain an ink jet recording sheet.

IJ Coating Comparative Example 2

Mixed in a ratio of 1:1 were a 10% dispersed solution obtained by stirring 10 parts of fine powder silica (Mizukasil P-78A, manufactured by Mizusawa Industrial Chemicals, Ltd.) and 90 parts of water at 3000 rpm for 3 minutes by means of a homogenizer and a 10% aqueous solution of polyvinyl alcohol (PVA-117S, manufactured by Kuraray Co., Ltd.) to prepare a coating solution. The resulting coating solution was coated on base paper for coating by means of a wire bar so that a coating amount became 5.0 g/m$^2$ and then dried at 120° C. for 90 seconds to obtain an ink jet recording sheet.

IJ Coating Comparative Example 3

The same operation as in IJ Coating Comparative Example 2 was carried out to obtain an ink jet recording sheet, except that polyvinyl alcohol was changed to polyvinylpyrrolidone (K-90, manufactured by ISP Co., Ltd.).

IJ Coating Comparative Example 4

The same operation as in IJ Coating Comparative Example 2 was carried out to obtain an ink jet recording sheet, except that fine powder silica was changed to fine powder alumina (Kataloid AP-3, manufactured by Catalysts & Chemicals Ind. Co. Ltd.).

IJ Coating Comparative Example 5

The same operation as in IJ Coating Comparative Example 2 was carried out to obtain an ink jet recording sheet, except that changed were polyvinyl alcohol to polyvinylpyrrolidone (K-90, manufactured by ISP Co., Ltd.) and fine powder silica to fine powder alumina (Kataloid AP-3, manufactured by Catalysts & Chemicals Ind. Co. Ltd.).

A printing aptitude and yellowing resistance of the ink jet recording sheets prepared by the method described above were tested in the following manners.

In the printing aptitude printing was carried out by means of an ink jet printer (PM-2000C, manufactured by Seiko Epson Corporation) to evaluate a print density and a dot form (roundness).

Solid printings of black, cyan, magenta and yellow were measured by means of a Macbeth densitometer (RD-918) to evaluate the print densities according to the following four grades criteria:

◎: print density is pretty high and excellent
○: print density is high
Δ: average
×: print density is low The prints were magnified under a magnifying glass and visually observed to evaluate the dot forms (roundness) according to the following four grades criteria:

◎: roundness is high and excellent
○: roundness is good
Δ: slight feathering is caused
×: no roundness The evaluation results are shown in Table 7.

The yellowing resistance was evaluated in the following manner.

An adhesive tape (cellophane tape: manufactured by Nichiban Co., Ltd.) was adhered on the ink jet recording sheet prepared and left standing at 20° C. for 4 weeks or at 40° C. for 2 weeks. The L, a and b values were measured by means of a spectrocolorimeter (Color Guide: manufactured by Byk-Gardner Co., Ltd.) to calculate the whole color difference $\Delta E$ ($\Delta E = \{(\Delta L)^2 + (\Delta a)^2 + (\Delta b)^2\}^{1/2}$), and the yellowing resistance was evaluated according to the following four grades criteria:

◎: the value of $\Delta E$ is small, and yellowing is scarcely caused
○, Δ, ×: yellowing is accelerated, and yellowing grows larger in this order As shown in Table 7, it can be found that the sheet coated thereon with the (meth)acrylamide base polymer/calcium phosphate fine particle-dispersed aqueous solutions do not turn yellow by adhering the adhesive tape and is excellent in yellowing resistance. Further, it can be found that the printing aptitude is excellent in a total balance and therefore an excellent ink jet recording chemical is provided.

Industrial Applicability

The water-soluble or water-dispersible high molecular compound containing a carboxyl group/inorganic fine particle-dispersed aqueous solution of the present invention has high paper-strengthening ability, and a layer coated with the above dispersed aqueous solution is excellent in yellowing resistance. Thus, the dispersed aqueous solution is useful as a paper-making chemical and an ink jet recording chemical. Further, a film and powder obtained from the above dispersed aqueous solution can be used as medical materials and cosmetic raw materials.

TABLE 1

Production examples of (meth)acrylamide base polymers

| | | | | Charge amount for Polymerization | | | | | | |
|---|---|---|---|---|---|---|---|---|---|---|
| Polymer Production Example | Polymer | Copoly- merizable monomer | Copoly- merization rate (mol %) | Acryl- amide (g) | Copoly- merizable monomer (g) | APS[8] (g) | SPM[9] (g) | 40% NaOH (g) | 35% HCl (g) | Distilled water (g) |
| 1 | A | — | — | 30.00 | — | 3.00 | 0.15 | — | — | 266.85 |
| 2 | B | AA[1] | 5.0 | 28.48 | 1.90 | 3.00 | 0.15 | 0.84 | — | 265.63 |
| 3 | C | AMPS[2] | 5.0 | 26.01 | 3.99 | 3.00 | 0.15 | 1.54 | — | 265.31 |
| 4 | D | JP[3] | 5.0 | 25.41 | 5.53 | 3.00 | 0.60 | 2.63 | — | 262.83 |
| 5 | E | DM[4] | 5.0 | 26.87 | 3.13 | 3.00 | 0.15 | — | 2.07 | 264.78 |

| | | | | Charge amount for Polymerization | | | | | | |
|---|---|---|---|---|---|---|---|---|---|---|
| Polymer Production Example | Polymer | Copoly- merizable monomer | Copoly- merization rate (mol %) | DMA[10] (g) | Copoly- merizable monomer (g) | APS (g) | SPM (g) | 40% NaOH (g) | 35% HCl (g) | Distilled water (g) |
| 6 | F | — | — | 30.00 | — | 3.00 | 0.15 | — | — | 266.85 |
| 7 | G | AA | 2.5 | 49.09 | 1.14 | 5.00 | 0.25 | 0.51 | — | 444.01 |
| 8 | H① | AA | 5.0 | 48.16 | 2.30 | 5.00 | 0.25 | 1.02 | — | 443.27 |
| 9 | H② | AA | 5.0 | 192.63 | 9.21 | 20.00 | 1.00 | 4.09 | — | 1773.07 |
| 10 | H③ | AA | 5.0 | 192.63 | 9.21 | 20.00 | 1.00 | 4.09 | — | 1773.07 |
| 11 | I | AA | 7.5 | 47.22 | 3.48 | 5.00 | 0.25 | 1.54 | — | 442.51 |
| 12 | J① | AA | 10.0 | 46.26 | 4.67 | 5.00 | 0.25 | 2.07 | — | 441.75 |
| 13 | J② | AA | 10.0 | 185.05 | 18.68 | 20.00 | 1.00 | 8.30 | — | 1767.00 |
| 14 | K | AA | 20.0 | 42.31 | 9.61 | 5.00 | 0.50 | 3.84 | — | 438.74 |
| 15 | L | AA | 25.0 | 20.12 | 6.10 | 2.50 | 0.38 | 2.44 | — | 218.74 |
| 16 | M① | AA | 30.0 | 19.06 | 7.42 | 2.50 | 0.19 | 3.30 | — | 217.50 |

TABLE 1-continued

Production examples of (meth)acrylamide base polymers

| 17 | M[2] | AA | 30.0 | 38.12 | 14.85 | 5.00 | 0.75 | 5.93 | — | 435.35 |
| 18 | N | IA[5] | 1.0 | 24.67 | 0.33 | 2.50 | 0.13 | 0.25 | — | 222.12 |
| 19 | O | MA[6] | 1.0 | 24.71 | 0.29 | 2.50 | 0.13 | 0.25 | — | 222.12 |
| 20 | P | FA[7] | 1.0 | 24.71 | 0.29 | 2.50 | 0.13 | 0.25 | — | 222.12 |

| Polymer Production Example | Polymer physical properties | | |
|---|---|---|---|
| | Viscosity mPa · s | Weight average molecular Weight | Solid Content (wt %) |
| 1 | 114.4 | 337,000 | 11.12 |
| 2 | 83.0 | 271,600 | 11.20 |
| 3 | 244.5 | 600,900 | 11.27 |
| 4 | 28.5 | 70,500 | 11.58 |
| 5 | 50.4 | 85,600 | 11.36 |
| 6 | 37.5 | 232,200 | 10.58 |
| 7 | 38.4 | 265,700 | 10.47 |
| 8 | 42.4 | 298,700 | 10.56 |
| 9 | 42.1 | 340,300 | 10.37 |
| 10 | 43.8 | 328,600 | 10.45 |
| 11 | 42.4 | 327,200 | 10.56 |
| 12 | 47.0 | 366,700 | 10.61 |
| 13 | 49.0 | 421,900 | 10.41 |
| 14 | 27.4 | 227,900 | 10.71 |
| 15 | 17.7 | 146,000 | 11.12 |
| 16 | 33.5 | 270,100 | 11.34 |
| 17 | 16.0 | 140,500 | 10.93 |
| 18 | 37.4 | 229,300 | 11.18 |
| 19 | 60.8 | 361,900 | 11.14 |
| 20 | 58.9 | 381,100 | 10.99 |

[1] Acrylic acid (80% product)
[2] 2-Acrylamide-2-methylpropanesulfonic acid
[3] Phosphoric acid mono(2-hydroxyethyl)methacrylate ester (83% product) (JAMP-514; manufactured by Johoku Chemical Co., Ltd.)
[4] N,N-dimethylaminoethyl methacrylate
[5] Itaconic acid
[6] Maleic acid
[7] Fumaric acid
[8] Ammonium persulfate (10% aqueous solution)
[9] Sodium hypophosphite monohydrate
[10] N,N-dimethylacrylamide

TABLE 2

Production examples of vinylpyrrolidone base polymers

| Polymer Production Example | Polymer | Copolymerizable monomer | Copolymerization rate (mol %) | Charge amount for Polymerization | | | | | | |
|---|---|---|---|---|---|---|---|---|---|---|
| | | | | NVP[6] (g) | Copolymerizable monomer (g) | V-501[7] (g) | SPM[8] (g) | 40% NaOH (g) | 35% HCl (g) | Distilled water (g) |
| 21 | R | IA[1] | 10.0 | 22.12 | 2.88 | 2.50 | 0.13 | 3.54 | — | 218.84 |
| 22 | S | MA[2] | 2.5 | 24.35 | 0.65 | 2.50 | 0.06 | 0.90 | — | 221.54 |
| 23 | T | MA | 5.0 | 23.70 | 1.30 | 2.50 | 0.13 | 1.80 | — | 220.58 |
| 24 | U | MA | 10.0 | 22.40 | 2.60 | 2.50 | 0.13 | 3.58 | — | 218.79 |

| Polymer Production Comparative Example | Polymer | Copolymerizable monomer | Copolymerization rate (mol %) | Charge amount for Polymerization | | | | | | |
|---|---|---|---|---|---|---|---|---|---|---|
| | | | | NVP (g) | Copolymerizable monomer (g) | V-50[9] (g) | SPM (g) | 40% NaOH (g) | 35% HCl (g) | Distilled water (g) |
| 1 | V | — | — | 30.00 | — | 1.50 | — | — | — | 268.50 |
| 2 | W | AMPS[3] | 5.0 | 27.31 | 2.68 | 1.50 | — | 1.03 | — | 267.47 |
| 3 | X | JP[4] | 5.0 | 26.89 | 3.74 | 3.00 | — | 1.78 | — | 264.58 |
| 4 | Y | DM[5] | 5.0 | 27.92 | 2.08 | 1.50 | — | — | 1.38 | 267.12 |

| Polymer | Polymer physical properties | | |
|---|---|---|---|
| | Viscosity mPa · s | Weight average molecular Weight | Solid Content (wt %) |

TABLE 2-continued

Production examples of vinylpyrrolidone base polymers

| Production Example | | | |
|---|---|---|---|
| 21 | 54.5 | 251,000 | 11.28 |
| 22 | 159.8 | 339,700 | 11.29 |
| 23 | 100.0 | 318,000 | 11.29 |
| 24 | 93.7 | 356,900 | 11.55 |
| Polymer Production Comparative Example | | | |
| 1 | 36.0 | 149,800 | 10.57 |
| 2 | 83.9 | 200,600 | 10.18 |
| 3 | 46.8 | 66,300 | 9.92 |
| 4 | 114.2 | 232,200 | 10.16 |

[1] Itaconic acid
[2] Maleic acid
[3] 2-Acrylamide-2-methylpropanesulfonic acid
[4] Phosphoric acid mono(2-hydroxyethyl)methacrylate ester (83% product) (JAMP-514; manufactured by Johoku Chemical Co., Ltd.)
[5] N,N-dimethylaminoethyl methacrylate
[6] N-vinyl-2-pyrrolidone
[7] 4,4'-Azobis(2-cycanovaleric acid) (V-501: manufactured by Wako Pure Chemical Industries, Ltd.) (10% aqueous solution)
[8] Sodium hypophosphite monohydrate
[9] 2,2'-Azobis(2-amidinopropane) dihydrochloride (V-50: manufactured by Wako Pure Chemical Industries, Ltd.) (10% aqueous solution)

TABLE 3

Compounding reaction-1 of acrylamide or vinylpyrrolidone base polymers with calcium phosphate

| | Compounding ratio | | | Charge amount (g) | | | |
|---|---|---|---|---|---|---|---|
| Compounding Example | Dispersed solution | Polymer | polymer:calcium phosphate (weight ratio) | Polymer (1) | Diluted phosphoric acid[1] (2) | Ca(OH)$_2$[2] (3) | Distilled water[3] |
| 1 | a-1 | A | 50:50 | 56.21 | 33.01 | 4.61 | 156.17 |
| 2 | b-1 | B | 50:50 | 55.81 | 33.01 | 4.61 | 156.58 |
| 3 | c-1 | C | 50:50 | 55.46 | 33.01 | 4.61 | 156.92 |
| 4 | d-1 | D | 50:50 | 53.97 | 33.01 | 4.61 | 158.41 |
| 5 | e-1 | E | 50:50 | 55.02 | 33.01 | 4.61 | 157.36 |
| 6 | f-1 | F | 50:50 | 59.07 | 33.01 | 4.61 | 153.31 |
| 7 | g-1 | G | 50:50 | 59.69 | 33.01 | 4.61 | 152.69 |
| 8 | h-1 | H(1) | 50:50 | 59.19 | 33.01 | 4.61 | 153.19 |
| 9 | h-2 | H(1) | 50:50 | 59.19 | 33.01 | 4.61 | 153.19 |
| 10 | h-3 | H(1) | 50:50 | 118.38 | 66.02 | 9.22 | 56.38 |
| 11 | h-4 | H(2) | 50:50 | 120.54 | 66.02 | 9.22 | 54.22 |
| 12 | h-5 | H(2) | 50:50 | 60.27 | 33.01 | 4.61 | 152.11 |
| 13 | h-6 | H(2) | 50:50 | 96.43 | 52.82 | 7.38 | 243.37 |
| 14 | h-7 | H(2) | 50:50 | 96.43 | 52.82 | 7.38 | 243.37 |
| 15 | h-8 | H(2) | 50:50 | 96.43 | 52.82 | 7.38 | 243.37 |
| 16 | h-9 | H(2) | 50:50 | 96.43 | 52.82 | 7.38 | 243.37 |
| 17 | h-10 | H(3) | 95:5 | 113.64 | 3.30 | 0.46 | 132.60 |
| 18 | h-11 | H(3) | 90:10 | 107.66 | 6.60 | 0.92 | 134.82 |
| 19 | h-12 | H(3) | 80:20 | 95.69 | 13.20 | 1.84 | 139.27 |
| 20 | h-13 | H(3) | 70:30 | 83.78 | 19.81 | 2.77 | 143.69 |
| 21 | h-14 | H(1) | 70:30 | 82.86 | 19.81 | 2.77 | 144.56 |
| 22 | h-15 | H(3) | 60:40 | 71.77 | 26.41 | 3.69 | 148.13 |
| 23 | h-16 | H(1) | 30:70 | 35.51 | 46.21 | 6.45 | 161.83 |
| 24 | i-1 | I | 50:50 | 59.19 | 33.01 | 4.61 | 153.19 |
| 25 | j-1 | J(1) | 50:50 | 58.91 | 33.01 | 4.61 | 153.47 |
| 26 | j-2 | J(2) | 50:50 | 60.04 | 33.01 | 4.61 | 152.34 |
| 27 | k-1 | K | 50:50 | 58.36 | 34.87 | 4.61 | 152.16 |
| 28 | l-1 | L | 50:50 | 56.21 | 34.87 | 4.61 | 153.31 |
| 29 | m-1 | M(2) | 50:50 | 60.04 | 33.01 | 4.61 | 152.34 |
| 30 | m-2 | M(1) | 30:70 | 33.07 | 51.35 | 6.45 | 159.13 |
| 31 | n-1 | N | 50:50 | 55.90 | 34.87 | 4.61 | 154.62 |
| 32 | o-1 | O | 50:50 | 56.10 | 34.87 | 4.61 | 154.42 |
| 33 | p-1 | P | 50:50 | 56.87 | 34.87 | 4.61 | 153.65 |

| Compounding Example | Feed solution Combination | Solution amount (g) | Adding/ aging (min) | Reaction method[4] | Stirring speed (rpm) | Reaction temperature (° C.) | Reaction solution pH | Standing dispersibility[5] | Centrifugal dispersibility[6] |
|---|---|---|---|---|---|---|---|---|---|

TABLE 3-continued

Compounding reaction-1 of acrylamide or vinylpyrrolidone base polymers with calcium phosphate

| | | | | | | | | | |
|---|---|---|---|---|---|---|---|---|---|
| 1  | ①+② | 100.0 | 120/60  | I  | 200 | 40 | 8.75  | 1 | 1 |
| 2  | ①+② | 100.0 | 120/60  | I  | 200 | 40 | #     | 1 | 1 |
| 3  | ①+② | 100.0 | 120/180 | I  | 200 | 40 | #     | 1 | 1 |
| 4  | ①+② | 100.0 | 120/60  | I  | 200 | 40 | #     | 1 | 1 |
| 5  | ①+② | 100.0 | 120/90  | I  | 200 | 40 | #     | 1 | 1 |
| 6  | ①+② | 100.0 | 120/60  | I  | 200 | 40 | #     | 1 | 1 |
| 7  | ①+② | 100.0 | 120/60  | I  | 200 | 40 | 9.87  | 1 | 1 |
| 8  | ①+② | 100.0 | 120/90  | I  | 200 | 40 | #     | 1 | 1 |
| 9  | ②   | 100.0 | 120/120 | II | 200 | 40 | #     | 1 | 1 |
| 10 | ②   | 100.0 | 120/180 | II | 200 | 40 | #     | 1 | 1 |
| 11 | ②   | 100.0 | 120/180 | II | 200 | 40 | 9.83  | 1 | 1 |
| 12 | ①+② | 100.0 | 120/60  | I  | 200 | 40 | 9.48  | 1 | 1 |
| 13 | ②   | 160.0 | 120/120 | II | 200 | 20 | 10.91 | 1 | 1 |
| 14 | ②   | 160.0 | 120/120 | II | 200 | 40 | 9.54  | 1 | 1 |
| 15 | ②   | 160.0 | 120/120 | II | 200 | 60 | 9.96  | 1 | 1 |
| 16 | ②   | 160.0 | 120/120 | II | 200 | 80 | 10.39 | 1 | 1 |
| 17 | ②   | 100.0 | 120/120 | II | 200 | 40 | 9.08  | 1 | 1 |
| 18 | ②   | 100.0 | 120/120 | II | 200 | 40 | 9.52  | 1 | 1 |
| 19 | ②   | 100.0 | 120/120 | II | 200 | 40 | 10.05 | 1 | 1 |
| 20 | ②   | 100.0 | 120/120 | II | 200 | 40 | 10.48 | 1 | 1 |
| 21 | ①+② | 100.0 | 120/90  | I  | 200 | 40 | #     | 1 | 1 |
| 22 | ②   | 100.0 | 120/120 | II | 200 | 40 | 10.66 | 1 | 1 |
| 23 | ①+② | 100.0 | 120/90  | I  | 200 | 40 | #     | 1 | 1 |
| 24 | ①+② | 100.0 | 120/60  | I  | 200 | 40 | 9.04  | 1 | 1 |
| 25 | ①+② | 100.0 | 120/90  | I  | 200 | 40 | #     | 1 | 1 |
| 26 | ①+② | 100.0 | 120/60  | I  | 200 | 40 | 8.68  | 1 | 1 |
| 27 | ②   | 100.0 | 120/120 | II | 300 | 40 | 10.35 | 1 | 1 |
| 28 | ②   | 100.0 | 120/120 | II | 300 | 40 | 10.52 | 1 | 1 |
| 29 | ②   | 100.0 | 120/120 | II | 300 | 40 | 10.35 | 1 | 1 |
| 30 | ②   | 100.0 | 120/120 | II | 200 | 40 | 6.52  | 1 | 1 |
| 31 | ②   | 100.0 | 120/120 | II | 300 | 40 | #     | 1 | 1 |
| 32 | ②   | 100.0 | 120/120 | II | 300 | 40 | #     | 1 | 1 |
| 33 | ②   | 100.0 | 120/120 | II | 300 | 40 | #     | 1 | 1 |

Those marked with # have no measured data.
[1] Aqueous solution prepared by diluting reagent phosphoric acid (85%) to 11.1%, and the mark * shows 10.5%.
[2] High purity reagent (3N) manufactured by Kanto Chemical Co., Inc.
[3] Total weight distributed to a flask and a feed according to an amount of a feed solution
[4] I: Polymer + phosphoric acid were dropwise added to a calcium hydroxide suspension, II: phosphoric acid was dropwise added to a calcium hydroxide + polymer suspension
[5] The compounded dispersed solution was left standing for a day after production to visually observe the state thereof, and the state was evaluated according to five grades criteria, in which it was shown by 1 that precipitates were scarcely observed and it was shown by 5 that the dispersed solution was completely separated and settled.
[6] The dispersed solution was subjected to centrifugal treatment at 2,000 rpm for 10 minutes to visually observe the state thereof, and the state was evaluated according to five grades criteria, in which it was shown by 1 that precipitates were scarcely observed and it was shown by 5 that the dispersed solution was completely separated and settled.

TABLE 4

Compounding reaction-2 of acrylamide or vinylpyrrolidone base polymers with calcium phosphate

| | | | Compounding ratio | Charge amount (g) | | | |
|---|---|---|---|---|---|---|---|
| | Dispersed Solution | Polymer | polymer:calcium phosphate (weight ratio) | Polymer ① | Diluted phosphoric acid[1] ② | Ca(OH)$_2$[2] ③ | Distilled water[3] |
| Compounding Example | | | | | | | |
| 34 | q-1 | Q[7] | 95:05 | 140.80 | 5.94   | 0.83 | 302.43 |
| 35 | q-2 | Q    | 90:10 | 133.40 | 11.88  | 1.66 | 303.06 |
| 36 | q-3 | Q    | 80:20 | 118.60 | 23.77  | 3.32 | 304.31 |
| 37 | g-4 | Q    | 70:30 | 103.80 | 35.65  | 4.98 | 305.57 |
| 38 | q-5 | Q    | 60:40 | 88.90  | 47.53  | 6.64 | 306.93 |
| 39 | r-1 | R    | 50:50 | 55.41  | *34.87 | 4.61 | 155.11 |
| 40 | s-1 | S    | 50:50 | 55.36  | *34.87 | 4.61 | 155.16 |
| 41 | t-1 | T    | 50:50 | 55.36  | *34.87 | 4.61 | 155.16 |
| 42 | u-1 | U    | 50:50 | 54.11  | *34.87 | 4.61 | 156.41 |
| Compounding Comparative Example | | | | | | | |
| 1 | Blank | —  | 0:100  | —     | 33.01 | 4.61 | 262.38 |
| 2 | v-1   | V  | 50:50  | 59.13 | 33.01 | 4.61 | 153.25 |
| 3 | w-1   | W  | 50:50  | 61.39 | 33.01 | 4.61 | 150.99 |

TABLE 4-continued

Compounding reaction-2 of acrylamide or vinylpyrrolidone base polymers with calcium phosphate

| | | | | | | | | |
|---|---|---|---|---|---|---|---|---|
| 4 | x-1 | X | 50:50 | 63.00 | 33.01 | | 4.61 | 149.38 |
| 5 | y-1 | Y | 50:50 | 51.52 | 33.01 | | 4.61 | 160.86 |

| Compounding Example | Feed solution Combination | Solution amount (g) | Adding/ aging (min) | Reaction method[4] | Stirring speed (rpm) | Reaction temperature (°C.) | Standing solution pH | Standing dispersibility[5] | Centrifugal dispersibility[6] |
|---|---|---|---|---|---|---|---|---|---|
| 34 | ② | 180.0 | 120/120 | II | 200 | 40 | 9.00 | 1 | 1 |
| 35 | ② | 180.0 | 120/120 | II | 200 | 40 | 8.98 | 1 | 1 |
| 36 | ② | 180.0 | 120/120 | II | 200 | 40 | 9.07 | 1 | 1 |
| 37 | ② | 180.0 | 120/120 | II | 200 | 40 | 9.10 | 1 | 1 |
| 38 | ② | 180.0 | 120/120 | II | 200 | 40 | 9.22 | 1 | 1 |
| 39 | ② | 100.0 | 120/120 | II | 300 | 40 | 8.62 | 1 | 1 |
| 40 | ② | 100.0 | 120/120 | II | 300 | 40 | 8.13 | 1 | 1 |
| 41 | ② | 100.0 | 120/120 | II | 300 | 40 | 9.80 | 1 | 1 |
| 42 | ② | 100.0 | 120/120 | II | 300 | 40 | 11.57 | 1 | 1 |

| Compounding Comparative Example | Feed solution Combination | Solution amount (g) | Adding/ ripening (min) | Reaction method[4] | Stirring speed (rpm) | Reaction temperature (°C.) | Standing solution pH | Standing dispersibility[5] | Centrifugal dispersibility[6] |
|---|---|---|---|---|---|---|---|---|---|
| 1 | ② | 100.0 | 120/60 | — | 200 | 40 | # | 5 | 5 |
| 2 | ① + ② | 100.0 | 120/60 | I | 200 | 40 | # | 5 | 5 |
| 3 | ① + ② | 100.0 | 120/90 | I | 200 | 40 | # | 5 | 5 |
| 4 | ① + ② | 100.0 | 120/90 | I | 200 | 40 | # | 5 | 5 |
| 5 | ① + ② | 100.0 | 120/90 | I | 200 | 40 | # | 5 | 5 |

Those marked with # have no measured data.
[1] Aqueous solution prepared by diluting reagent phosphoric acid (85%) to 11.1%, the mark * shows 10.5%
[2] High purity reagent (3N) manufactured by Kanto Chemical Co., Inc.
[3] Total weight distributed to a flask and a feed according to an amount of a feed solution
[4] I: Polymer + phosphoric acid were dropwise added to a calcium hydroxide suspension, II: phosphoric acid was dropwise added to a calcium hydroxide + polymer suspension
[5] The compounded dispersed solution was left standing for a day after production to visually observe the state thereof, and the state was evaluated according to five grades criteria, in which it was shown by 1 that precipitates were scarcely observed and it was shown by 5 that the dispersed solution was completely separated and settled.
[6] The dispersed solution was subjected to centrifugal treatment at 2,000 rpm for 10 minutes to visually observe the state thereof, and the state was evaluated according to five grades criteria, in which it was shown by 1 that precipitates were scarcely observed and it was shown by 5 that the dispersed solution was completely separated and settled.
[7] Carboxyl group-containing polyacrylamide (Hopelon -3150B: manufactured by Mitsui Chemicals Inc.)

TABLE 5

Compounding reaction of carboxyl group-modified polyvinyl alcohol with calcium phosphate

| Compounding Example | Dispersed solution | Polymer[1] | Compounding ratio polymer: calcium phosphate (weight ratio) | Polymer ① | Diluted phosphoric acid[2] ② | Ca(OH)$_2$[3] ③ | NaOH (10 wt %) | Distilled water[4] | Combination | Solution amount (g) |
|---|---|---|---|---|---|---|---|---|---|---|
| 43 | Z1-1 | Z1 | 95:05 | 11.88 | 3.50 | 0.46 | 1.62 | 232.54 | ② | 100.0 |
| 44 | Z1-2 | Z1 | 95:05 | 11.88 | 3.50 | 0.46 | 0.13 | 234.03 | ② | 100.0 |
| 45 | Z1-3 | Z1 | 90:10 | 11.25 | 6.99 | 0.92 | 0.09 | 230.75 | ② | 100.0 |
| 46 | Z1-4 | Z1 | 80:20 | 10.00 | 13.99 | 1.84 | 0.12 | 224.05 | ② | 100.0 |
| 47 | Z1-5 | Z1 | 70:30 | 8.75 | 20.98 | 2.77 | 0.14 | 217.36 | ② | 100.0 |
| 48 | Z1-6 | Z1 | 60:40 | 7.50 | 27.98 | 3.69 | 0.10 | 210.73 | ② | 100.0 |
| 49 | Z1-7 | Z1 | 50:50 | 6.25 | 34.97 | 4.61 | 0.14 | 204.03 | ② | 100.0 |
| 50 | Z1-8 | Z1 | 50:50 | 6.25 | 34.97 | 4.61 | 0.06 | 204.11 | ② | 100.0 |
| 51 | Z1-9 | Z1 | 50:50 | 25.00 | 138.95 | 18.44 | 0.42 | 817.19 | ② | 400.0 |
| 52 | Z2-1 | Z2 | 50:50 | 6.25 | 34.97 | 4.61 | 0.03 | 204.14 | ② | 100.0 |
| 53 | Z3-1 | Z3 | 95:05 | 11.88 | 3.50 | 0.46 | 1.08 | 233.08 | ② | 100.0 |
| 54 | Z3-2 | Z3' | 50:50 | 6.25 | 34.97 | 4.61 | 1.42 | 202.75 | ② | 100.0 |
| 55 | Z4-1 | Z4 | 95:05 | 11.88 | 3.50 | 0.46 | 5.39 | 228.77 | ② | 100.0 |
| 56 | Z4-2 | Z4 | 50:50 | 6.25 | 34.97 | 4.61 | 0.04 | 204.13 | ② | 100.0 |
| 57 | Z5-1 | Z5 | 95:05 | 11.88 | 3.50 | 0.46 | 2.16 | 232.00 | ② | 100.0 |
| 58 | Z5-2 | Z5 | 50:50 | 6.25 | 34.97 | 4.61 | 0.02 | 204.15 | ② | 100.0 |
| 59 | Z6-1 | Z6 | 50:50 | 6.25 | 34.97 | 4.61 | 0.09 | 204.08 | ② | 100.0 |
| 60 | Z7-1 | Z7 | 50:50 | 6.25 | 34.97 | 4.61 | 0.06 | 204.11 | ② | 100.0 |
| 61 | Z8-1 | Z8 | 50:50 | 6.25 | 34.97 | 4.61 | 0.06 | 204.11 | ② | 100.0 |
| 62 | Z9-2 | Z9 | 50:50 | 6.25 | 34.97 | 4.61 | 0.04 | 204.13 | ② | 100.0 |
| 63 | Z10-1 | Z10 | 50:50 | 6.25 | 34.97 | 4.61 | 0.09 | 204.08 | ② | 100.0 |

TABLE 5-continued

Compounding reaction of carboxyl group-modified polyvinyl alcohol with calcium phosphate

| 64 | Z11-1 | Z11 | 50:50 | 6.25 | 34.97 | 4.61 | 0.08 | 204.09 | ② | 100.0 |
| 65 | Z12-1 | Z12 | 50:50 | 6.25 | 34.97 | 4.61 | 0.08 | 204.09 | ② | 100.0 |
| 66 | Z13-1 | Z13 | 50:50 | 6.25 | 34.97 | 4.61 | 0.05 | 204.12 | ② | 100.0 |

[1] The abbreviations of the carboxyl group-modified PVA's correspond to the followings (PVA which was dissolved in advance in a concentration of about 10 wt % was used, and the charge amount in the above table is shown in terms of a solid content)
Z1: KM-118, Z2: KM-618, Z3: KL-118 (Z3' was subjected in advance to hydrolysis treatment with NaOH), Z4: KM-5112 and Z5: SK-5102 (all manufactured by Kuraray Co., Ltd.), Z6: UFA170 and Z7: UFA170M and Z8: UPA170 (all manufactured by Unitika Ltd.), Z9: T-330H, Z10: T-330, Z11: T-350, Z12: T-230 and Z13: T-215 (all manufactured by The Nippon Synthetic Chemical, Industry Co., Ltd.) others: Z14: 103C, Z15: 205C, Z16: CM-318 and Z17: 205S (Z14' and Z16' were subjected in advance to hydrolysis treatment with NaOH) (all manufactured by Kuraray Co., Ltd.)
[2] Aqueous solution prepared by diluting reagent phosphoric acid (85%) to 10.5%, and the mark * shows an aqueous solution diluted to 11.1%
[3] High purity reagent (3N) manufactured by Kanto Chemical Co., Inc.
[4] Total weight distributed to a flask and a feed according to an amount of a feed solution
[5] I: Polymer + phosphoric acid were dropwise added to a calcium hydroxide suspension, II: phosphoric acid was dropwise added to a calcium hydroxide + polymer suspension
[6] The compounded dispersed solution was left standing for a day after production to visually observe the state thereof, and the state was evaluated according to five grades criteria, in which it was shown by 1 that precipitates were scarcely observed and it was shown by 5 that the dispersed solution was completely separated and settled.
*2: Trace amount of precipitates is observed; 1 and 2 are encompassed in the scope of the stable dispersed solutions of the present invention
[7] The dispersed solution was subjected to centrifugal treatment at 2,000 rpm for 10 minutes to visually observe the state thereof, and the state was evaluated according to five grades criteria, in which it was shown by 1 that precipitates were scarcely observed and it was shown by 5 that the dispersed solution was completely separated and settled.

| Compounding Example | Adding/ aging (min) | Reaction Method[5] | Stirring speed (rpm) | Reaction temperature (°C.) | Reaction solution pH | Standing dispersibility[6] | Centrifugal dispersibility[7] | Viscosity mPa·s | Solid concentration (wt %) |
|---|---|---|---|---|---|---|---|---|---|
| 43 | 120/120 | II | 200 | 40 | 6.55 | 1 | 1 | # | 5.2 |
| 44 | 120/120 | II | 200 | 40 | 5.62 | 1 | 1 | 40.6 | 5.1 |
| 45 | 120/120 | II | 200 | 40 | 5.59 | 1 | 1 | 35.0 | 5.1 |
| 46 | 120/120 | II | 200 | 40 | 6.08 | 1 | 1 | 28.3 | 5.1 |
| 47 | 120/120 | II | 200 | 40 | 6.64 | 1 | 1 | 24.8 | 5.1 |
| 48 | 120/120 | II | 200 | 40 | 6.98 | 1 | 1 | 24.6 | 5.1 |
| 49 | 120/120 | II | 200 | 40 | 7.28 | 1 | 1 | 28.0 | 5.1 |
| 50 | 120/120 | II | 200 | 40 | 7.60 | 1 | 1 | 28.4 | 4.9 |
| 51 | 120/120 | II | 300 | 40 | 7.83 | 1 | 1 | 32.1 | 5.1 |
| 52 | 120/120 | II | 200 | 40 | 6.24 | 1 | 1 | 16.4 | 4.9 |
| 53 | 120/120 | II | 200 | 40 | 5.83 | 1 | 1 | # | 5.2 |
| 54 | 120/120 | II | 200 | 40 | 8.08 | 1 | 1 | # | 5.1 |
| 55 | 120/120 | II | 200 | 40 | 9.54 | 1 | 1 | # | 5.4 |
| 56 | 120/120 | II | 200 | 40 | 7.69 | 1 | 1 | 41.8 | 4.9 |
| 57 | 120/120 | II | 200 | 40 | 7.91 | 1 | 1 | # | 5.2 |
| 58 | 120/120 | II | 200 | 40 | 7.97 | 1 | 1 | 5.4 | 4.9 |
| 59 | 120/120 | II | 300 | 40 | 7.03 | 1 | 1 | # | 5.1 |
| 60 | 120/120 | II | 300 | 40 | 5.80 | 1 | 1 | # | 5.0 |
| 61 | 120/120 | II | 300 | 40 | 5.26 | 2 | 1 | # | 5.0 |
| 62 | 120/120 | II | 300 | 40 | 7.73 | 1 | 1 | # | 5.1 |
| 63 | 120/120 | II | 300 | 40 | 6.49 | 1 | 1 | # | 5.1 |
| 64 | 120/120 | II | 300 | 40 | 5.74 | 1 | 1 | # | 5.1 |
| 65 | 120/120 | II | 300 | 40 | 6.17 | 2 | 1 | # | 5.1 |
| 66 | 120/120 | II | 300 | 40 | 7.98 | 1 | 1 | # | 5.1 |

Those marked with # have no measured data.

| Compounding Comparative Example | Dispersed solution | Polymer[1] | Compounding ratio polymer: calcium phosphate (weight ratio) | Polymer ① | Diluted phosphoric acid[2] ② | Ca(OH)₂[3] ③ | NaOH (10 wt %) | Distilled water[4] | Combination | Solution amount (g) |
|---|---|---|---|---|---|---|---|---|---|---|
| 6 | Z14-1 | Z14 | 50:50 | 6.25 | 34.97 | 4.61 | 0.05 | 204.12 | ② | 100.0 |
| 7 | Z14-2 | Z14' | 50:50 | 6.25 | 34.97 | 4.61 | 0.57 | 203.60 | ② | 100.0 |
| 8 | Z15-1 | Z15 | 50:50 | 6.25 | 34.97 | 4.61 | 0.05 | 204.12 | ② | 100.0 |
| 9 | Z16-1 | Z16 | 50:50 | 6.25 | 34.97 | 4.61 | 0.05 | 204.12 | ② | 100.0 |
| 10 | Z16-2 | Z16' | 50:50 | 6.25 | 34.97 | 4.61 | 1.99 | 202.18 | ② | 100.0 |
| 11 | Z17-1 | Z17 | 50:50 | 6.25 | *33.01 | 4.61 | — | 206.13 | ① + ② | 100.0 |

| Compounding Comparative Example | Adding/ aging (min) | Reaction Method[5] | Stirring speed (rpm) | Reaction temperature (°C.) | Reaction solution pH | Standing dispersibility[6] | Centrifugal dispersibility[7] | Viscosity mPa·s | Solid matter concentration (wt %) |
|---|---|---|---|---|---|---|---|---|---|
| 6 | 120/120 | II | 200 | 40 | 7.61 | 4 | 5 | # | 5.0 |
| 7 | 120/120 | II | 200 | 40 | 8.05 | 4 | 5 | # | 5.2 |
| 8 | 120/120 | II | 200 | 40 | 5.43 | 4 | 5 | # | 4.9 |
| 9 | 120/120 | II | 200 | 40 | 5.62 | 3 | 5 | # | 4.9 |

TABLE 5-continued

Compounding reaction of carboxyl group-modified polyvinyl alcohol with calcium phosphate

| 10 | 120/120 | II | 200 | 40 | 5.93 | 3 | 5 | # | 5.1 |
| 11 | 120/120 | I  | 200 | 40 | #    | 5 | 5 | # | #   |

TABLE 6

Strength measurement of coated paper

| | Composition ratio (weight ratio) of compounded dispersed solution (meth)acrylamide base polymer/ calcium phosphate | Coating amount g/m² | RI pick (10 marks evalution) | Z axis strength mJ |
|---|---|---|---|---|
| Coating Example 1 | 95/5 | 1.0 | 6.8 | 241.5 |
|  |  | 1.8 | 7.2 | 355.6 |
| Coating Example 2 | 90/10 | 1.0 | 6.7 | 237.1 |
|  |  | 1.8 | 7.2 | 342.0 |
| Coating Example 3 | 80/20 | 1.0 | 6.8 | 248.4 |
|  |  | 1.8 | 7.3 | 336.1 |
| Coating Example 4 | 70/30 | 1.0 | 6.3 | 242.9 |
|  |  | 1.8 | 7.2 | 354.2 |
| Coating Example 5 | 60/40 | 1.0 | 6.2 | 240.5 |
|  |  | 1.8 | 7.2 | 325.0 |
| Coating Comparative Example 1 | 100/0 | 1.0 | 5.8 | 211.0 |
|  |  | 1.8 | 6.2 | 316.5 |
| Base paper for coating | — | 0.0 | 3.0 | 123.4 |

TABLE 7

Print test of ink jet-coated paper

| | Print density | | | | Dot shape | Yellowing resistance | |
|---|---|---|---|---|---|---|---|
| | Black | Cyan | Magenta | Yellow | (roundness) | 20° C./4 weeks | 40° C./2 weeks |
| Coating Example 1 | ○ | ○ | ○ | ○ | ⊙ | ⊙ | ⊙ |
| Coating Comparative Example 1 | ○ | ○ | ○ | ○ | × | × | Δ |
| Coating Comparative Example 2 | ⊙ | ○ | Δ | ○ | × | × | × |
| Coating Comparative Example 3 | × | Δ | ○ | ○ | × | ⊙ | ⊙ |
| Coating Comparative Example 4 | ⊙ | ⊙ | ⊙ | ⊙ | × | × | × |
| Coating Comparative Example 5 | ○ | ○ | ○ | ○ | × | × | × |
| Base paper for coating | × | × | × | × | × | ○ | ○ |

What is claimed is:

1. An organic polymer/inorganic fine particle-dispersed aqueous solution having excellent dispersion stability comprising a water-soluble or water-dispersible synthetic high molecular compound (A) having a carboxyl group and a water-slightly soluble inorganic fine particle (B) having a particle diameter of 500 nm or less in a proportion of (A):(B)=10:90 to 99.99:0.01 (weight ratio), wherein (B) is a fine particle of a compound of a second, group element in the periodic table synthesized in the presence of (A).

2. The organic polymer/inorganic fine particle-dispersed aqueous solution having excellent dispersion stability as described in claim 1, wherein the water-slightly soluble inorganic fine particle (B) having a particle diameter of 500 nm or less is synthesized by reacting (a) a compound of second group element in the periodic table with (b) at least one compound selected from organic acids, inorganic acids and salts thereof in the presence of the water-soluble or water-dispersible synthetic high molecular compound (A) having a carboxyl group.

3. The organic polymer/inorganic fine particle-dispersed aqueous solution having excellent dispersion stability as described in claim 2, wherein (b) the organic acid or inorganic acid is at least one acid selected from oxo-acids and hydrohalogenic acids.

4. The organic polymer/inorganic fine particle dispersed aqueous solution having excellent dispersion stability as described in claim 2, wherein (a) the compound of a second group element in the periodic table is a calcium compound.

5. The organic polymer/inorganic fine particle dispersed aqueous solution having excellent dispersion stability as described in claim 2, wherein the water-soluble or water-dispersible synthetic high molecular compound (A) having a carboxyl group is a polymer of an ethylenically unsaturated compound.

6. The organic polymer/inorganic fine particle-dispersed aqueous solution having excellent dispersion stability as described in claim 5, wherein the polymer of the ethylenically unsaturated compound is any of a (meth)acrylamide base polymer, a carboxyl group-modified polyvinyl alcohol and a vinylpyrrolidone base polymer.

7. The organic polymer/inorganic fine particle dispersed aqueous solution having excellent dispersion stability as described in claim 5, wherein the polymer of the ethylenically unsaturated compound is any of:

(1) a (meth)acrylamide base polymer which is a polymer of 1 to 100% by weight of an ethylenically unsaturated carboxylic acid amide compound and 0 to 99% by weight of a copolymerizable, ethylenically unsaturated compound, (2) a carboxyl group-modified polyvinyl alcohol which is produced by saponifying a polymer of an ethylenically unsaturated carboxylic acid and vinyl acetate, and (3) a vinylpyrrolidone base polymer which Is a polymer of 1 to 99.9% by weight of N-vinyl-2-pyrrolidone and 0.1 to 99% by weight of a copolymerizable, ethylenically unsaturated compound.

8. The organic polymer/inorganic fine particle-dispersed aqueous solution having excellent dispersion stability as described in claim 2, wherein the water-slightly soluble inorganic fame particle (B) is calcium phosphate.

9. A production process for an organic polymer/inorganic fine particle-dispersed aqueous solution having excellent dispersion stability, characterized by producing a water-slightly soluble inorganic fine particle (B) having a particle diameter of 500 nm or less by reacting (a) a compound of a second group element in the periodic table with (b) at least one compound selected from organic acids, inorganic acids and salts thereof in the presence of a water-soluble or water-dispersible synthetic high molecular compound (A) having a carboxyl group.

10. An organic polymer/inorganic fine particle-composite having excellent transparency comprising a water-soluble or water-dispersible synthetic high molecular compound (A) having a carboxyl group and a water-slightly soluble inorganic fine particle (B) having a particle diameter of 500 nm or less obtained by reacting (a) a compound of a second group element in the periodic table with (b) at least one compound selected from organic acids, inorganic acids and salts thereof in the presence of (A) in a proportion of (A):(B)=10:90 to 99.99:0.01 (weight ratio).

11. An organic polymer/inorganic fine particle-composite having excellent transparency obtained from the organic polymer/inorganic, fine particle-dispersed aqueous solution having excellent dispersion stability as described in claim 1, comprising a water-soluble or water-dispersible synthetic high molecular compound (A) having a carboxyl group and a soluble inorganic fine particle (B) having a particle diameter of 500 nm or less in a proportion of (A):(B)=10:90 to 99.99:0.01 (weight ratio).

12. An organic polymer/inorganic fine particle-composite having excellent transparency obtained from the organic polymer/inorganic fine particle-dispersed aqueous solution having excellent dispersion stability as described in claim 2, comprising a water-soluble or water-dispersible synthetic high molecular compound (A) having a carboxyl group and a water-slightly soluble inorganic fine particle (B) having a particle diameter of 500 nm or less in a proportion of (A):(B)=10:90 to 99.99:0.01 (weight ratio).

13. An organic polymer/inorganic fine particle-composite having excellent transparency obtained from the organic polymer/inorganic fine particle-dispersed aqueous solution having excellent dispersion stability as described in claim 8, comprising a water-soluble or water-dispersible synthetic high molecular compound (A) having a carboxyl group and a water-slightly soluble inorganic fine particle (B) having a particle diameter of 500 nm or less in a proportion of (A):(B)=10:90 to 99.99:0.01 (weight ratio).

14. The organic polymer/inorganic fine particle-composite having excellent transparency as described in claim 10, wherein the composite is a film having excellent transparency.

15. The organic polymer/inorganic fine particle-composite having excellent transparency as described in claims 11, wherein the composite is a film having excellent transparency.

16. The organic polymer/inorganic fine particle-composite having excellent transparency as described in claim 12, wherein the composite is a film having excellent transparency.

17. The organic polymer/inorganic fine particle-composite having excellent transparency as described in claim 13, wherein the composite is a film having excellent transparency.

18. The organic polymer/inorganic fine particle-composite having excellent transparency as described in claim 10, wherein the water-soluble or water-dispersible synthetic high molecular compound (A) having a carboxyl group is any of a (meth)acrylamide base polymer, a carboxyl group-modified polyvinyl alcohol and a vinylpyrrolidone base polymer.

19. The organic polymer/inorganic fine particle-composite having excellent transparency as described in claim 10, wherein the water-slightly soluble inorganic fine particle (B) is calcium phosphate.

20. A paper-making chemical comprising a water-soluble or water-dispersible synthetic high molecular compound (A) having a carboxyl group and a water-slightly soluble inorganic fine particle (B) having a particle diameter of 500 nm or less obtained by reacting (a) a compound of a second group element in the periodic table with (b) at least one compound selected from organic acids, inorganic acids and salts thereof in a proportion of (A):(B) 10:90 to 99.99:0.01 (weight ratio).

21. A paper-making chemical obtained from the organic polymer/inorganic fine particle-dispersed aqueous solution having excellent dispersion stability as described in claim 1.

22. A paper-making chemical obtained from the organic polymer/inorganic fine particle-dispersed aqueous solution having excellent dispersion stability as described in claim 2.

23. A paper-making chemical obtained from the organic polymer/inorganic fine particle-dispersed aqueous solution having excellent dispersion stability as described in claim 8.

24. A chemical for an ink-jet recording sheet comprising a water-soluble or water-dispersible synthetic high molecular compound (A) having a carboxyl group and a water-scarcely soluble inorganic fine particle (B) having a particle diameter of 500 nm or less obtained by reacting (a) a compound of a second group element in the periodic table with (a) at least one compound selected from organic acids, inorganic acids and salts thereof in a proportion of (A):(B)= 10:90 to 99.99:0.01 (weight ratio).

25. A chemical for an ink-jet recording sheet obtained from the organic polymer/inorganic fine particle-dispersed aqueous solution having excellent dispersion stability as described in claim 1.

26. A chemical for an ink-jet recording sheet obtained from the organic polymer/inorganic fine particle-dispersed aqueous solution having excellent dispersion stability as described in claim 2.

27. A chemical for an ink-jet recording sheet obtained from the organic polymer/inorganic fine particle-dispersed aqueous solution having excellent dispersion stability as described in claim 8.

28. The chemical as described in claim 20, wherein the water-soluble or water-dispersible synthetic high molecular compound (A) having a carboxyl group is any of a (meth) acrylamide base polymer, a carboxyl group-modified polyvinyl alcohol and a vinylpyrrolidone base polymer.

29. The chemical as described in claim 24, wherein the water-soluble or water-dispersible synthetic high molecular compound (A) having a carboxyl group is any of a (meth) acrylamide base polymer, a carboxyl group-modified polyvinyl alcohol and a vinylpyrrolidone base polymer.

30. The chemical as described in claim 20, wherein the water-slightly soluble inorganic fine particle (B) is calcium phosphate.

31. The chemical as described in claim 24, wherein the water-slightly soluble inorganic fine particle (B) is calcium phosphate.

32. Paper obtained by using the chemical as described in claim 20.

33. Paper obtained by using the chemical as described in claim 21.

34. Paper obtained by using the chemical as described in claim 22.

35. Paper obtained by using the chemical as described in claim 23.

36. Paper obtained by using the chemical as described in claim 24.

37. Paper obtained by using the chemical as described in claim 25.

38. Paper obtained by using the chemical as described in claim 26.

39. Paper obtained by using the chemical as described in claim 27.

40. A cosmetic comprising the organic polymer/inorganic fine particle-dispersed aqueous solution having excellent dispersion stability as described in claim 1.

41. A cosmetic comprising the organic polymer/inorganic fine particle-dispersed aqueous solution having excellent dispersion stability as described in claim 2.

42. A cosmetic comprising the organic polymer/inorganic fine particle-dispersed aqueous solution having excellent dispersion stability as described in claim 8.

43. A cosmetic comprising the organic polymer/inorganic fine particle-composite having excellent transparency as described in claim 10.

44. A cosmetic comprising the organic polymer/inorganic fine particle-composite having excellent transparency as described in claim 11.

45. A cosmetic comprising the organic polymer/inorganic fine particle-composite having excellent transparency as described in claim 12.

46. A cosmetic comprising the organic polymer/inorganic fine particle-composite having excellent transparency as described in claim 13.

47. An organic polymer/inorganic fine particle-dispersed aqueous solution having excellent dispersion stability comprising a water-soluble or water-dispersible synthetic high molecular compound (A) having a carboxyl group and calcium phosphate (B) having a particle diameter of 500 run or less in a proportion of (A):(B) 10:90 to 99.99:0–01 (weight ratio).

48. An organic polymer/inorganic fine particle-composite having excellent transparency comprising a water-soluble or water-dispersible synthetic high molecular compound (A) having a carboxyl group and calcium phosphate (B) having a particle diameter of 500 nm or less in a proportion of (A):(B)=10:90 to 99.99:0.01 (weight ratio).

* * * * *